(12) United States Patent
Wagers et al.

(10) Patent No.: US 11,725,033 B2
(45) Date of Patent: Aug. 15, 2023

(54) GDF11 VARIANTS AND USES THEREOF

(71) Applicant: President and Fellows of Harvard College, Cambridge, MA (US)

(72) Inventors: Amy J. Wagers, Cambridge, MA (US); Jill Goldstein, Cambridge, MA (US); Ryan G. Walker, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 84 days.

(21) Appl. No.: 16/933,908

(22) Filed: Jul. 20, 2020

(65) Prior Publication Data

US 2021/0101951 A1 Apr. 8, 2021

Related U.S. Application Data

(63) Continuation of application No. PCT/US2019/014363, filed on Jan. 18, 2019.

(60) Provisional application No. 62/654,303, filed on Apr. 6, 2018, provisional application No. 62/619,683, filed on Jan. 19, 2018.

(51) Int. Cl.
*A61K 38/18* (2006.01)
*C07K 14/51* (2006.01)
*A61K 38/00* (2006.01)

(52) U.S. Cl.
CPC .............. *C07K 14/51* (2013.01); *A61K 38/00* (2013.01)

(58) Field of Classification Search
CPC .. A61K 38/00; A61K 38/179; A61K 38/1796; A61K 38/18; A61K 8/64; A61K 47/643; A61K 47/644; A61K 38/22; A61P 21/00; C07K 14/475; C07K 14/71; C07K 2319/00; C07K 14/51; C07K 2317/55; C07K 16/2863; C07K 19/00; C07K 2319/33; C07K 14/575; C07K 2333/71
See application file for complete search history.

(56) References Cited

U.S. PATENT DOCUMENTS

| | | | |
|---|---|---|---|
| 9,434,779 B2* | 9/2016 | Lee | ........................ C07K 14/51 |
| 10,092,627 B2* | 10/2018 | Wagers | .............. A61K 38/1875 |
| 2003/0104977 A1 | 6/2003 | Ripamonti et al. | |
| 2015/0045297 A1 | 2/2015 | Lee et al. | |
| 2016/0074477 A1 | 3/2016 | Wagers et al. | |
| 2016/0220640 A1* | 8/2016 | Rubin | ................ A61K 38/1875 |

FOREIGN PATENT DOCUMENTS

| | | |
|---|---|---|
| WO | WO-1999/024057 A2 | 5/1999 |
| WO | WO-2018/112362 A1 | 6/2018 |

OTHER PUBLICATIONS

GeneBank: AAH59367.1 Human Transferrin. Jul. 17, 2006. https://www.ncbi.nlm.nih.gov/protein/AAH59367 .1 (Year: 2006).*
International Search Report from PCT/US2019/014363, dated Apr. 8, 2019.

* cited by examiner

*Primary Examiner* — Aradhana Sasan
*Assistant Examiner* — Jia-Hai Lee
(74) *Attorney, Agent, or Firm* — Morse, Barnes-Brown & Pendleton, P.C.; Lisa M. Warren, Esq.

(57) ABSTRACT

Disclosed herein are GDF11 variant polypeptides. Also disclosed herein are methods for increasing GDF11 protein levels in a subject by administering a GDF11 variant polypeptide.

20 Claims, 31 Drawing Sheets

Specification includes a Sequence Listing.

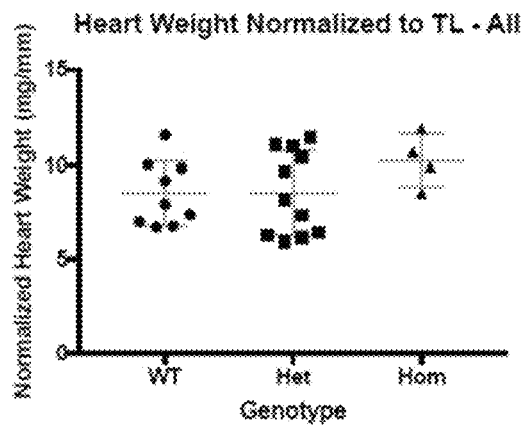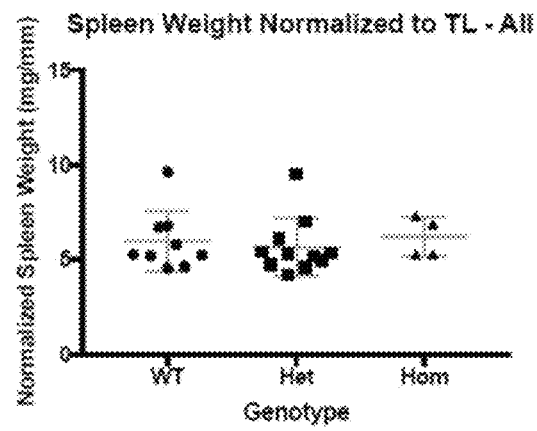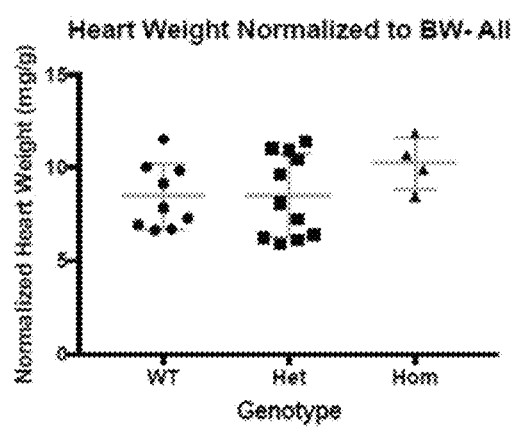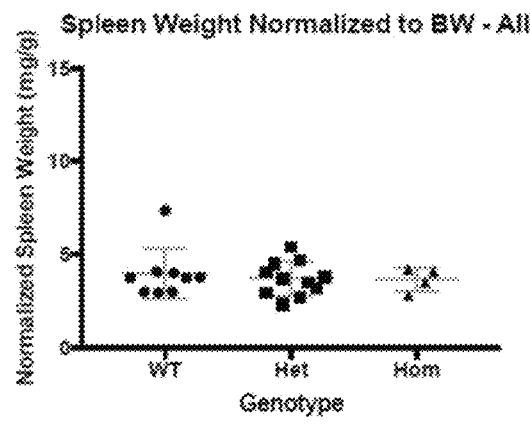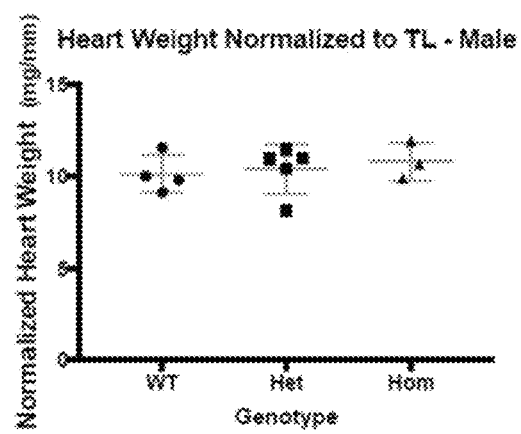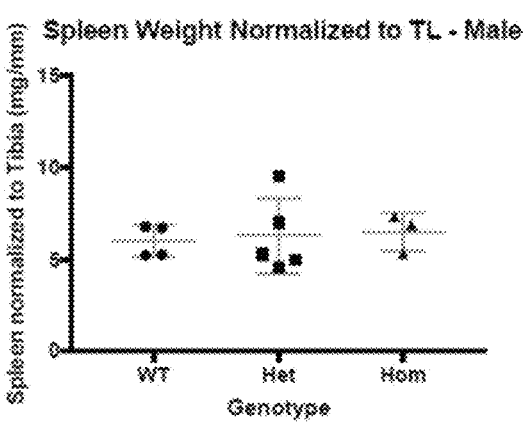
FIG. 10B
FIG. 10C

N Terminus -
MVLAAPLLLGFLLLALELRPRGEAAEGPAAAAAAAGVGGERSSRPAPSAPPEPDG
CPVCVWRQHSRELRLESIKSQILSKLRLKEAPNISREVVKQLLPKAPPLQQILDLHDFQG
DALQPEDFLEEDEYHATTETVISMAQETDPAVQTDGSPLCCHFHFSPKVMFTKVLKAQL
WVYLRPVPRPATVYLQILRLKPLTGEGTAGGGGGGRHIRIRSLKIELHSRGHWQSIDF
KQVLHSWFRQPQSNWGIEINAFDPSGTDLAVTSLGPGAEGLHPFMELRVLENTKRSRR
NLGLDCDEHSSESRCCRYPLTVDFEAFGWDWIIAPKRYKANYCSGQCEYMFMQKYPH
THLVQQANPRGSAGPCCTPTKMSPINMLYFNDKQQIIYGKIPGMVVDRCGCS [WE]
- C Terminus     (SEQ ID NO: 20)

AA Sequence Detected by LC/MS/MS

Indel 7 Variation

FIG. 13A

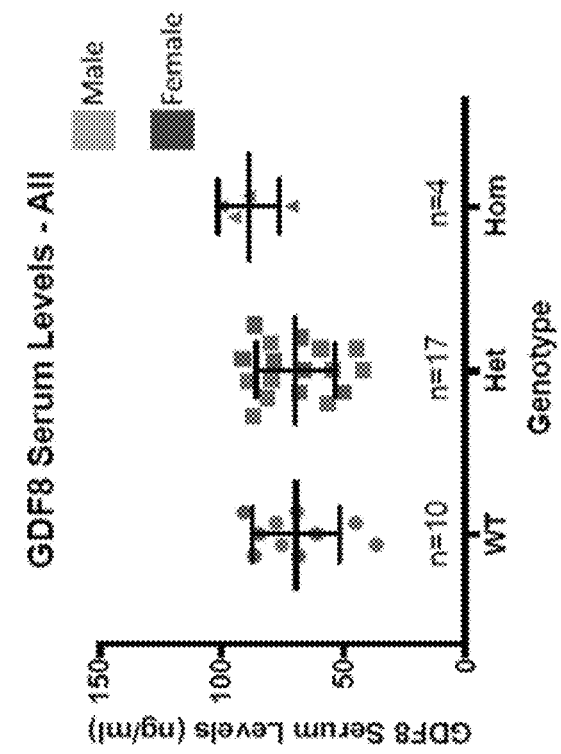
FIG. 13B
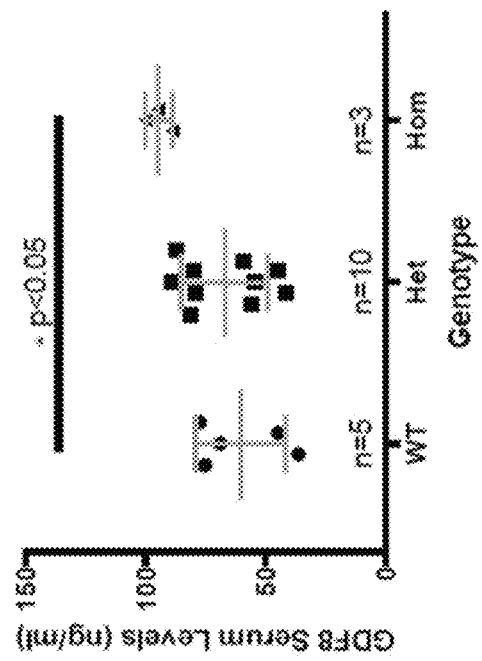
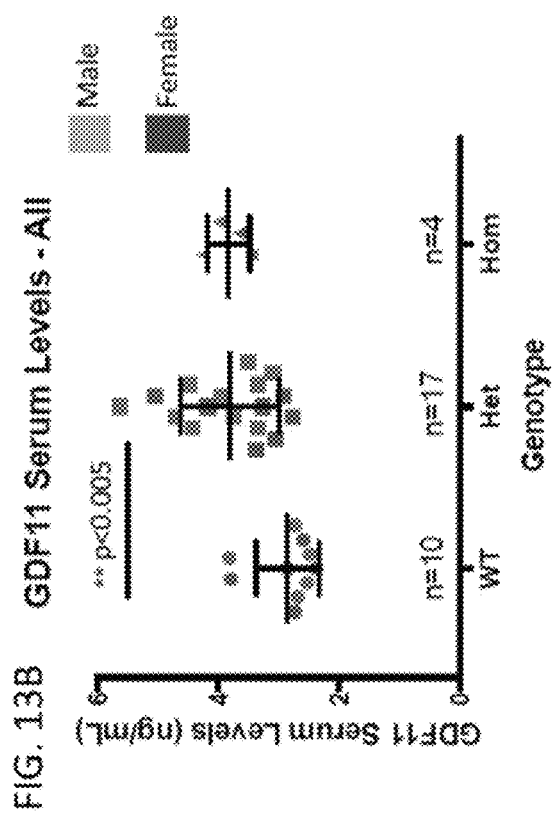
FIG. 13C
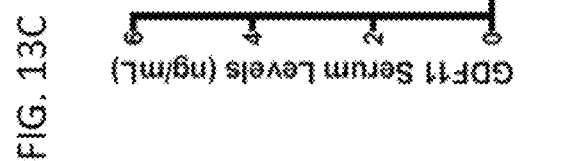

SEQUENCE LISTING

<160> NUMBER OF SEQ ID NOS: 20

<210> SEQ ID NO 1
<211> LENGTH: 407
<212> TYPE: PRT
<213> ORGANISM: Homo sapiens

<400> SEQUENCE: 1

```
Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
```

-continued

```
                165                 170                 175
Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
    290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
        355                 360                 365

Gly Pro Cys Cys Thr Pro Thr Lys Met Ser Pro Ile Asn Met Leu Tyr
    370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 2
<211> LENGTH: 383
<212> TYPE: PRT
<213> ORGANISM: Homo sapiens

<400> SEQUENCE: 2

Ala Glu Gly Pro Ala Ala Ala Ala Ala Ala Ala Ala Ala
1               5                   10                  15

Ala Gly Val Gly Gly Glu Arg Ser Ser Arg Pro Ala Pro Ser Val Ala
            20                  25                  30

Pro Glu Pro Asp Gly Cys Pro Val Cys Val Trp Arg Gln His Ser Arg
        35                  40                  45

Glu Leu Arg Leu Glu Ser Ile Lys Ser Gln Ile Leu Ser Lys Leu Arg
    50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
                85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
        115                 120                 125
```

```
Val Gln Thr Asp Gly Ser Pro Leu Cys Cys His Phe His Phe Ser Pro
    130                 135                 140
Lys Val Met Phe Thr Lys Val Leu Lys Ala Gln Leu Trp Val Tyr Leu
145                 150                 155                 160
Arg Pro Val Pro Arg Pro Ala Thr Val Tyr Leu Gln Ile Leu Arg Leu
                165                 170                 175
Lys Pro Leu Thr Gly Glu Gly Thr Ala Gly Gly Gly Gly Gly Gly Arg
            180                 185                 190
Arg His Ile Arg Ile Arg Ser Leu Lys Ile Glu Leu His Ser Arg Ser
        195                 200                 205
Gly His Trp Gln Ser Ile Asp Phe Lys Gln Val Leu His Ser Trp Phe
    210                 215                 220
Arg Gln Pro Gln Ser Asn Trp Gly Ile Glu Ile Asn Ala Phe Asp Pro
225                 230                 235                 240
Ser Gly Thr Asp Leu Ala Val Thr Ser Leu Gly Pro Gly Ala Glu Gly
                245                 250                 255
Leu His Pro Phe Met Glu Leu Arg Val Leu Glu Asn Thr Lys Arg Ser
            260                 265                 270
Arg Arg Asn Leu Gly Leu Asp Cys Asp Glu His Ser Ser Glu Ser Arg
        275                 280                 285
Cys Cys Arg Tyr Pro Leu Thr Val Asp Phe Glu Ala Phe Gly Trp Asp
    290                 295                 300
Trp Ile Ile Ala Pro Lys Arg Tyr Lys Ala Asn Tyr Cys Ser Gly Gln
305                 310                 315                 320
Cys Glu Tyr Met Phe Met Gln Lys Tyr Pro His Thr His Leu Val Gln
                325                 330                 335
Gln Ala Asn Pro Arg Gly Ser Ala Gly Pro Cys Cys Thr Pro Thr Lys
            340                 345                 350
Met Ser Pro Ile Asn Met Leu Tyr Phe Asn Asp Lys Gln Gln Ile Ile
        355                 360                 365
Tyr Gly Lys Ile Pro Gly Met Val Val Asp Arg Cys Gly Cys Ser
    370                 375                 380

<210> SEQ ID NO 3
<211> LENGTH: 109
<212> TYPE: PRT
<213> ORGANISM: Homo sapiens

<400> SEQUENCE: 3

Asn Leu Gly Leu Asp Cys Asp Glu His Ser Ser Glu Ser Arg Cys Cys
1               5                   10                  15
Arg Tyr Pro Leu Thr Val Asp Phe Glu Ala Phe Gly Trp Asp Trp Ile
                20                  25                  30
Ile Ala Pro Lys Arg Tyr Lys Ala Asn Tyr Cys Ser Gly Gln Cys Glu
            35                  40                  45
Tyr Met Phe Met Gln Lys Tyr Pro His Thr His Leu Val Gln Gln Ala
        50                  55                  60
Asn Pro Arg Gly Ser Ala Gly Pro Cys Cys Thr Pro Thr Lys Met Ser
65                  70                  75                  80
Pro Ile Asn Met Leu Tyr Phe Asn Asp Lys Gln Gln Ile Ile Tyr Gly
                85                  90                  95
Lys Ile Pro Gly Met Val Val Asp Arg Cys Gly Cys Ser
            100                 105

<210> SEQ ID NO 4
```

-continued

```
<211> LENGTH: 274
<212> TYPE: PRT
<213> ORGANISM: Homo sapiens

<400> SEQUENCE: 4

Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
            20                  25                  30

Pro Glu Pro Asp Gly Cys Pro Val Cys Val Trp Arg Gln His Ser Arg
        35                  40                  45

Glu Leu Arg Leu Glu Ser Ile Lys Ser Gln Ile Leu Ser Lys Leu Arg
    50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
                85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
        115                 120                 125

Val Gln Thr Asp Gly Ser Pro Leu Cys Cys His Phe His Phe Ser Pro
130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175

Lys Pro Leu Thr Gly Glu Gly Thr Ala Gly Gly Gly Gly Gly Gly Arg
            180                 185                 190

Arg His Ile Arg Ile Arg Ser Leu Lys Ile Glu Leu His Ser Arg Ser
        195                 200                 205

Gly His Trp Gln Ser Ile Asp Phe Lys Gln Val Leu His Ser Trp Phe
    210                 215                 220

Arg Gln Pro Gln Ser Asn Trp Gly Ile Glu Ile Asn Ala Phe Asp Pro
225                 230                 235                 240

Ser Gly Thr Asp Leu Ala Val Thr Ser Leu Gly Pro Gly Ala Glu Gly
                245                 250                 255

Leu His Pro Phe Met Glu Leu Arg Val Leu Glu Asn Thr Lys Arg Ser
            260                 265                 270

Arg Arg

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
catgcaaaag tatccacaca cc                                          22

<210> SEQ ID NO 6
<211> LENGTH: 20
<212> TYPE: DNA
<213> ORGANISM: Artificial Sequence
<220> FEATURE:
<223> OTHER INFORMATION: Primer
```

```
<400> SEQUENCE: 6
cctggactgc gatgaacact                                                  20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
cctactgagt tgtcagggga ac                                               22

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ctggaaggag agagggaaaa a                                                21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ctgcgcctag agagcatcaa g                                                21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ttggaagtcg tgcagatcca g                                                21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
acagagcaac tggggaatcg                                                  20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
agtgttcatc gcagtccagg                                                  20

<210> SEQ ID NO 13
<211> LENGTH: 24
```

```
<212> TYPE: DNA
<213> ORGANISM: Artificial Sequence
<220> FEATURE:
<223> OTHER INFORMATION: Primer

<400> SEQUENCE: 13
atcaagatca ttgctcctcc tgag                                              24

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ctgcttgctg atccacatct g                                                 21

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
tgggtgctca tgggagtaag acctgcagaa gcttggc                                37

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
cttctgcagg tcttactccc atgagcaccc acagcgg                                37

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
aatacgactc actataggg                                                    19

<210> SEQ ID NO 18
<211> LENGTH: 17
<212> TYPE: DNA
<213> ORGANISM: Artificial Sequence
<220> FEATURE:
<223> OTHER INFORMATION: Primer

<400> SEQUENCE: 18
caggaaacag ctatgac                                                      17

<210> SEQ ID NO 19
<211> LENGTH: 6792
<212> TYPE: DNA
<213> ORGANISM: Artificial Sequence
<220> FEATURE:
<223> OTHER INFORMATION: GDF11 variant

<400> SEQUENCE: 19
```

```
tccccgcccc ccagtcctcc cctccctgc agcatggtgc tcgcggcccc gctgctgctg    60
ggcttcctgc tcctcgccct ggagctgcgg ccccggggg aggcggccga gggccccgcg   120
gcggcggcgg cggcagcggc ggcggcggcc ggggtcgggg gggagcgctc gagccggccg   180
gccccgtccg ctccgccgga gccggacggc tgccccgtgt gcgtgtggcg gcagcacagc   240
cgcgagctgc gcctagagag catcaagtcg cagatcctga gcaaactgcg gctcaaggag   300
gcgcccaaca tcagccggga ggtagtgaag cagctgctgc ccaaggcgcc gccgctgcag   360
cagatcctgg atctgcacga cttccaaggc gacgcgctgc agcctgagga cttcttggaa   420
gaggacgagt accacgctac caccgagacg gtcataagca tggcccagga gagtaagtgg   480
gctgcggggt gcgcgcggtg cggtgcagtc cgggaaggac ccggaagccc tttctgcgaa   540
aacttgacgg attggggagc cgggccactc cacacaactt tttgagcgga gaagatgggc   600
agcggagttg agtgcacgcc ccgttctagg gtggggggt ggaggatggc gcgttggggg   660
agggggccca aaccaggcag gttgtgagct attgctttcc atcccttgtg agaaaaagat   720
tcaagttgaa gtagtcctag aaactggcac cctacgtga ctttctgga gcgttaggtg   780
gggagcttcc gtgacccgtg cagtctcagc tgggccgcag tgccatcttc ccactgctct   840
ggcaccagca tcaactcctt gcccggtgct ccggaaggcg cccaccggct ttcggaaaaa   900
ctaagtgttc ctctaaggcc atggcatagg acccaaaccc ggtgtacgtc tcagcaactc   960
agctgacacc tctcctttct gcacctgatc tcgcactggg tatcccctag gacctagaag  1020
agctgttcct tcctggtacc gaaagagctc aaataactca actccactgc gcttgccact  1080
taacgagtat catttggtta ctctcatctt agcgtgctca ctccctgtcc tacccacagc  1140
tggagccaaa gaagacccag ggagaaagaa ctagatgagg gggatgggag aacccaggca  1200
tccgagcccc tggccaaacg gaggatgaac actctgatag acaggagcgg ctttgaaatt  1260
ttatggcctg gaaaatccag gccaatacta ccgcccccac tgccttctct ccctagggtc  1320
aggtgactcc ctttccctc ccccactgac tgtagtcccc ccccccccca actccaggga  1380
accaggcttt ctctattccc tagtggtttg gcaagccccc cctcctttgg ttttatggct  1440
ctgaacagaa gggggggctg gtttattggc agatgggtca taaaaagctg ggggttgcgg  1500
gaaatcctag tggcccaccc ccatggtaga ggtacaggaa cccaggtgtg catttggaag  1560
gttgagagcc tggcacttgc cacccagttt ctgcagaatt caactccaac ttggttagga  1620
ttgtaaagaa aactcagagt caggaaactc tctctctctc tctctctctc tctctctctc  1680
tctctctctc tctctctctc tctctctctc tctcgtgtgt atgtgtatgt gtatgtgtgt  1740
gagtgtgtgt gtgtgtgtgt gtgtgtgtgt gtgtgcacag agatctgatc ttgggttctc  1800
aggctcccctt gttcttattg cttctacttt tggaaaccag ggtcagtctt tgattgacta  1860
agggcaggga tagggaaaag attctagaaa acagttgtag ggaaataatg aatgacaaaa  1920
ttttctggaa gatgcaggat atatagaaa aagatactct gctctgtgtg atgtaaagtg  1980
tgtatttcca gggtgagtga cccagctgca ggcttcccat tgccttcact atccctagcc  2040
tcctgtaacc agaaggcttg agtccagaat taactctggt agtggagagc agcaggaagt  2100
gaagggactc tgaatgcaca aattgggcag tagccattaa gcctggggt gggattgtac  2160
cagtagatga agttgggtct caccctgact tccattttag tgccactcca ggacttaggt  2220
aacccaggaa ctgggtttca aaccaggtat tgtacttccc ctttaagagt ctagctgcga  2280
ccttaagaga gggaggggga gtagagggga gggagggag agaggagagg ggggaaaagg  2340
aaaagagac ttttatagtc taatccccag ggacccgctt taataagaga cttgtgctct  2400
```

| | |
|---|---|
| gctaatcggg ggaggtgttt gtcagcagag atggcctctg ctcccctccc cctgcctccc | 2460 |
| ctcccccagc caaccccgga ccccagcccc cacctttcct aggctgttcg gcctgcccta | 2520 |
| gttccctcta ccctctcact ctcccacccc agccttcatc cctgggaacc cagcccctg | 2580 |
| ctcttctagg agccaagccc tgcccctcag tttgtctctc ctgtgcacgc taagaggccc | 2640 |
| ctgccctctc gcccaacctc ctgcccctgg gccatccagc ctgagttggg agagggtgtg | 2700 |
| tggtggggtg gaggctgtag gcagagaggg ggttgggcct ttgctgaaaa tagtgcagtg | 2760 |
| acctctctcc cccaccagca ccgcctccta aacctgacct gctgcctgcc accaaccaaa | 2820 |
| tcaatccaac acagatgtgg cccccttcccc tccccaccag agctccatag ctttacctgc | 2880 |
| ttctttgttc cttcttctgc acctttccat ctcttcttta ccccacgagg gtcccacctt | 2940 |
| tgccctctta ccttacccac tccagtccag tctacccagt gtttccattt cccaaacatt | 3000 |
| tgctcccatt actgtgatct acttgttccg ttcctctgct ggtcttggtc taacctgtct | 3060 |
| tcattctgtc tcttcattct tatcttatca tcttcaacct cttcctttcc ttacatcttg | 3120 |
| tcccctagaa acatgactgc agatacacag atgtatatgt ggattccctg gggcagcagt | 3180 |
| agaggaaccc ttgtccgaag gaagcagact taagaaggat atcccatgac cctgtctcag | 3240 |
| ccttaagtgg gatgtttagt ttataaaatg aacatttatt gggaaactat tattatttt | 3300 |
| catgttattt aatgcacaga attatttgta tgtccctcag aagtatagtg gctaaggtta | 3360 |
| agtaccaggc aacaacccag gcacatggtt aaacctttca ttgttgccag aagagtctgg | 3420 |
| gaagaacctg ccattcaaca tgtattcact gcttgacatg atgggagcca cagagaaact | 3480 |
| acaatggtga taaaatattc tcaggacatc aaccctcaca gagatgagta tctaatgaca | 3540 |
| aaaaaacaga taattcagct ggacctggtg gtaccagcat gtaatcccga ctactcagga | 3600 |
| gcctgaagca ggaatttatg aagtccaaag ccttcctgaa gtacagagta caaggccagc | 3660 |
| cttgggcaac cctgtctcaa aattaggaga aagagaatga agctcagggg tggggttctt | 3720 |
| gcctagcagg tgtgaggccc aaggtttgct ccccagtaac acgcacatga gtatgtgcat | 3780 |
| acacgcgctc acacgcacag ctgtgctgca atcagatgca gtgtgcatct aggcttactg | 3840 |
| tcacatccta atctctgcat ttccattcct catccgtatt ctaccttaca tgagtaagtg | 3900 |
| tcagaacact gggatcttgg atgctgcggg aggacatggt gtgtcctgtt ctgagtagtc | 3960 |
| agtacatact ttgttcctcg tcacactcag aggagtcctc ttcctggggt gatggagagc | 4020 |
| gttctccatg gcatggttat gcagatggta atacttgggt gtgacgacag ggacctggac | 4080 |
| ttcaccatta cttacacggc tctggaacaa cctcattcca gattcttcct atctagaaa | 4140 |
| tgaacaattt agggcatctc taacccactt aaagaggtca ggaaaagctg gcatagtgg | 4200 |
| tacatgctgt aatctcaaca cctgggaaga tgagacagga gaactgctat gagctgagac | 4260 |
| tagcatgggc tatataggga cagtcagaga cacttaacaa acccatgtct caaaacaaag | 4320 |
| gctgagaaga gcttaaggaa agcaaatgga cacactgaga accttcctgg agactcctta | 4380 |
| ggatcttgaa ccatggaaag tggctaaaat gtaaagttgg gacgttaact ttgtaaagtt | 4440 |
| agaggcactg cattaagcaa acaaaggag gtcaagggag gagagatggc tgcttatagt | 4500 |
| tgacgcaatg tgttgaatat ggtttctgat actctgggca agaaggacac tctgaacttt | 4560 |
| cccttcctca gaagctgagt gtctccgctg gcagtgagga agcagcagag gacgcagaat | 4620 |
| ggggagtcag aatcacagga aatgcttggt agctccattc tgaagggcgt gctactggga | 4680 |
| atcaggagcc tggatctgct ctgacttact ttataaaccc atctctcagg accctgggtt | 4740 |

```
atttcctctg atgcctcctt tgcttttca ggggagtggg ctgccaggct ccacctgctc    4800
attagatgaa ccgggtaagg tagcttgagg acagcaggtg cagcaaagag cattagagac    4860
cagctgagaa gcactggggc agggaaggcc tcagatggag gtagactcca cagctatctt    4920
agcagaggga tcctttgtgc taggagaaat gttataggg atagtataga tcagtaaggc      4980
ctaacagact catcatccta gtgatgagac aattttaggt accagagaca taatagccaa    5040
caatacaggc acagaagggt aaagaggaat tggaaagcag gctgagaaga atctgctaaa    5100
gccaccgggg ctgctgaacc cctccctcca cagataccct tttctgatgt tgtgccccct    5160
tctctcttat cagcggaccc tgcagtgcag acagatggca gccctctctg ctgtcatttc    5220
cacttcagcc ccaaggtgat gttcaccaag gtactgaagg cccaactgtg ggtgtacctt    5280
cggcctgtgc cccgcccagc cacagtctac ctgcagatct tacgactgaa acccctaact    5340
ggggaaggga ccgcaggggg aggggtgga ggccggcgtc acatccgtat ccgttcacta      5400
aagattgagc tacactcacg ttccggccac tggcagagca tcgacttcaa gcaagtgcta    5460
cacagctggt ttcgccagcc acagagcaac tggggaatcg agatcaacgc ctttgatccc    5520
agcggcacag acctggctgt cacctccctg ggccaggag ctgaggggct ggtgagcagg      5580
gggcctgaag tggtggtgga ggatatgtat aacctgtccc caagagatgg gagttagaaa    5640
aagtagatca ggaatgtggt ggttggggcc aggaactaat ttcagaggag gtggggtagc    5700
aactatcact tttcagggat ttaagccaga tgacagctga aaactaaaac tggatttggg      5760
gtgaaggtat cagttagtgg gagatccgtg ggaacacaaa gctgacccct tgggcgtggtg    5820 ttatctaatc ctcgcagtag ggaggccaga caggagggcc aggagctcta gaccgttacc    5880
tttgctacat agcaaatctg aggtcaacct gagcgacatg agagcccatc tcaaaacaaa    5940
acagaacctg gcccttgaca aggcgctggg ccaagaaccc gatgaggtca cattgccaga    6000
aaaggaagaa ttagggaaag tgagcaggag agacgtctag atgtcaagag aagtgctcac    6060
aatgtctggg tgggagccgt aaacaagcca agaggttatg gtttctggtc tgatgctcct    6120
gttgagatca ggaaatgttc aggaaatccc ctgttgagat gtaggaaagt aagaggtaag    6180
agacattgtt gagggtcatg tcacatctct ttccctctc cctgaccctc agcatccttt      6240
catggagctt cgagtcctag agaacacgaa aaggtcccgg cggaacctag gcctggactg    6300
cgatgaacac tcgagtgagt cccgctgctg ccgatatcct ctcacagtgg actttgaggc    6360
ttttggctgg gactggatca tcgcacctaa gcgctacaag gccaactact gctccggcca    6420
gtgcgaatac atgttcatgc aaaagtatcc acacacccac ttggtgcaac aggccaaccc    6480
aagaggctct gctgggccct gctgcacccc taccaagatg tccccaatca acatgctcta    6540
cttcaatgac aagcagcaga ttatctacgg caagatccct ggcatggtgg tggatcgatg    6600
tggctgctcc tgggagtaag cagagagccc tgccccaagc ctgttttcc acagcaaggt      6660 gagaggcttg gtatagtttg ggggagttcc cctgacaact cagtaggagt aagtcagagt    6720
ccattcttag cttttccct ctctccttcc agtagcagcc ggaagtggac cgaggatggg      6780
gcaaagtaag ga                                                                      6792
```

<210> SEQ ID NO 20
<211> LENGTH: 407
<212> TYPE: PRT
<213> ORGANISM: Artificial Sequence
<220> FEATURE:
<223> OTHER INFORMATION: GDF11 variant

<400> SEQUENCE: 20

```
Met Val Leu Ala Ala Pro Leu Leu Gly Phe Leu Leu Ala Leu
1               5               10              15

Glu Leu Arg Pro Arg Gly Glu Ala Ala Glu Gly Pro Ala Ala Ala
            20              25              30

Ala Ala Ala Ala Ala Ala Gly Val Gly Glu Arg Ser Ser Arg
        35              40              45

Pro Ala Pro Ser Ala Pro Pro Glu Pro Asp Gly Cys Pro Val Cys Val
    50              55              60

Trp Arg Gln His Ser Arg Glu Leu Arg Leu Glu Ser Ile Lys Ser Gln
65              70              75              80

Ile Leu Ser Lys Leu Arg Leu Lys Glu Ala Pro Asn Ile Ser Arg Glu
            85              90              95

Val Val Lys Gln Leu Leu Pro Lys Ala Pro Pro Leu Gln Gln Ile Leu
            100             105             110

Asp Leu His Asp Phe Gln Gly Asp Ala Leu Gln Pro Glu Asp Phe Leu
        115             120             125

Glu Glu Asp Glu Tyr His Ala Thr Thr Glu Thr Val Ile Ser Met Ala
    130             135             140

Gln Glu Thr Asp Pro Ala Val Gln Thr Asp Gly Ser Pro Leu Cys Cys
145             150             155             160

His Phe His Phe Ser Pro Lys Val Met Phe Thr Lys Val Leu Lys Ala
                165             170             175

Gln Leu Trp Val Tyr Leu Arg Pro Val Pro Arg Pro Ala Thr Val Tyr
            180             185             190

Leu Gln Ile Leu Arg Leu Lys Pro Leu Thr Gly Glu Gly Thr Ala Gly
            195             200             205

Gly Gly Gly Gly Gly Arg Arg His Ile Arg Ile Arg Ser Leu Lys Ile
210             215             220

Glu Leu His Ser Arg Ser Gly His Trp Gln Ser Ile Asp Phe Lys Gln
225             230             235             240

Val Leu His Ser Trp Phe Arg Gln Pro Gln Ser Asn Trp Gly Ile Glu
                245             250             255

Ile Asn Ala Phe Asp Pro Ser Gly Thr Asp Leu Ala Val Thr Ser Leu
            260             265             270

Gly Pro Gly Ala Glu Gly Leu His Pro Phe Met Glu Leu Arg Val Leu
    275             280             285

Glu Asn Thr Lys Arg Ser Arg Arg Asn Leu Gly Leu Asp Cys Asp Glu
    290             295             300

His Ser Ser Glu Ser Arg Cys Cys Arg Tyr Pro Leu Thr Val Asp Phe
305             310             315             320

Glu Ala Phe Gly Trp Asp Trp Ile Ile Ala Pro Lys Arg Tyr Lys Ala
                325             330             335

Asn Tyr Cys Ser Gly Gln Cys Glu Tyr Met Phe Met Gln Lys Tyr Pro
            340             345             350

His Thr His Leu Val Gln Gln Ala Asn Pro Arg Gly Ser Ala Gly Pro
            355             360             365

Cys Cys Thr Pro Thr Lys Met Ser Pro Ile Asn Met Leu Tyr Phe Asn
    370             375             380

Asp Lys Gln Gln Ile Ile Tyr Gly Lys Ile Pro Gly Met Val Val Asp
385             390             395             400

Arg Cys Gly Cys Ser Trp Glu
                405
```

GDF11 VARIANTS AND USES THEREOF

CROSS-REFERENCE TO RELATED APPLICATIONS

This application is a continuation of PCT Application No. PCT/US2019/014363, filed on Jan. 18, 2019, which claims the benefit of U.S. Provisional Application No. 62/619,683, filed on Jan. 19, 2018, and U.S. Provisional Application No. 62/654,303, filed on Apr. 6, 2018. The entire teachings of the above applications are incorporated herein by reference.

GOVERNMENT SUPPORT

This invention was made with government support under AG048917 and AG050395 awarded by the National Institutes of Health. The government has certain rights in the invention.

BACKGROUND OF THE INVENTION

Age-dependent dysfunction in adult stem cells is attributable to both cell-intrinsic and -extrinsic inputs. Critical mechanisms underlying the functional decline of aged stem cells remain elusive. Accordingly, there exists a need to identify factors that are able to promote or reverse age-associated changes in tissues as diverse as the skeletal muscle, liver and CNS (Wagers and Conboy, Cell 122: 659 (2005); Ruckh et al., Cell Stem Cell 10:96 (2005)).

SUMMARY OF THE INVENTION

In some aspects, the invention is directed to a GDF11 variant having at least one GDF11 activity. In certain aspects the GDF11 variant has GDF11 activity that is equivalent to or greater than the corresponding activity of native GDF11. In some embodiments the GDF11 variant exhibits protein stability that is equivalent to or greater than the stability of native GDF11. In some embodiments the variant is produced by the modification of the coding sequence of the native protein to result in modification of the C-terminus of the polypeptide. In some embodiments the variant comprises the addition, deletion, or substitution of one or more amino acids compared to the native polypeptide sequence. In some embodiments the variant comprises the inclusion of one, two, or three additional amino acids as compared to the native polypeptide; in some embodiments the variant comprises the addition of one, two, at least two, or three amino acids at the C-terminus. In some embodiments the variant comprises the addition of two amino acids at the C-terminus, and in some embodiments the variant comprises the addition of tryptophan and glutamic acid (e.g., tryptophan followed by glutamic acid) at the C-terminus region. GDF11 variants encompassed by the invention include both variant polypeptides and the nucleotide sequences encoding them.

In some aspects, the disclosure provides pharmaceutical compositions comprising a GDF11 variant described herein, e.g., wherein the GDF11 variant comprises inclusion of at least two amino acids at the C-terminus region, and a pharmaceutically acceptable carrier.

In some aspects, the disclosure provides methods for increasing levels of circulating GDF11 protein in a subject. The methods comprise administering to the subject a GDF11 variant polypeptide, thereby increasing the levels of circulating GDF11 protein in the subject.

In other aspects, the disclosure provides methods for increasing angiogenesis in a subject in need thereof. The methods comprise administering to the subject a GDF11 variant polypeptide, thereby increasing angiogenesis in the subject. In some embodiments, increasing angiogenesis comprises increasing cerebrovascular architecture, increasing capillary density, increasing cerebral blood flow, and increasing cerebral vessel sprouting branch points.

In some aspects, the disclosure provides methods for increasing neurogenesis in a subject in need thereof. The methods comprise administering to the subject a GDF11 variant polypeptide, thereby increasing neurogenesis in the subject. In some embodiments, increasing neurogenesis is associated with increased neural cell proliferation, increased neural cell differentiation, increased number or proliferation rate of neural stem cells, increased number or proliferation rate of neural progenitor cells, increased number or proliferation rate of neural precursor cells, increased expression of at least one synaptic plasticity gene, at least one neuroprotective gene, or at least one neuronal specification gene, or increased number of new neurons.

In some embodiments of any aspect described herein, the administration of GDF11 variant polypeptide to the subject increases functional GDF11 protein (i.e., a GDF11 protein having at least one function of the native or wild type protein) in the subject. The level of GDF11 protein may be increased in at least one of the subject's systemic circulation, cerebral vasculature, cerebral tissue, cerebrospinal fluid, lateral ventricles, neurovasculature, and subventricular zone neurovascular niche. In some embodiments, the level of GDF11 protein is increased by at least 100%, at least 90%, at least 80%, at least 70% or at least 50%. In some embodiments, the level of GDF11 protein is increased to at least 75% of a healthy reference level.

In some aspects, the disclosure provides methods for treating or preventing a neurovascular disorder or neurodegenerative disorder in a subject. The methods comprise administering to the subject a GDF11 variant polypeptide which increases the level of GDF11 protein in the subject, thereby treating or preventing the neurovascular or neurodegenerative disorder in the subject.

In other aspects, the disclosure provides methods of rejuvenating skeletal muscle stem cells in a subject in need thereof. The methods comprise administering to the subject a GDF11 variant polypeptide.

In some embodiments, the GDF11 variant polypeptide increases the levels of circulating GDF11 protein in the subject. In some embodiments, the GDF11 variant causes the subject's skeletal muscle stem cells to increase in frequency or number, increase the sizes of regenerating myofibers, increase the efficiency of myogenic colony formation, increase the percentage of intact nuclei, and decrease the percentage of severely damaged deoxyribonucleic acid (DNA), thereby rejuvenating the skeletal muscle stem cells in the subject.

In other aspects, the invention is directed to methods of increasing strength or exercise endurance capacity in a subject in need thereof. The methods comprise administering to the subject a GDF11 variant polypeptide in the subject, thereby increasing the strength or exercise endurance capacity.

In some embodiments, in any aspect described herein, the subject has been diagnosed with a skeletal muscle condition due to aging. In some embodiments, the level of GDF11 protein is increased in the systemic circulation of the subject. In some embodiments, the level of GDF11 protein is increased in the skeletal muscle tissue of the subject.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, available on the World Wide Web at ncbi.nlm nih.gov/omim/ and in Online Mendelian Inheritance in Animals (OMIA), a database of genes, inherited disorders and traits in animal species (other than human and mouse), at omia.angis.org.au/contact.shtml.

All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5A provides a schematic of the unprocessed GDF11 protein, with arrows pointing to proteolytic sites where cleavage must occur. Yellow arrows represent cleavage by tolloid-like metalloproteinase, green arrows by signal peptidase, and red arrows by a furin protease. FIG. 5B provides a schematic that shows how GDF11 is processed into its inactive latent complex and then active ligand form. Ordered proteolytic processing is needed to create the mature dimer. FIG. 5C provides an image showing the structure of myostatin, with the two distinct interfaces that bind to receptors. FIG. 5D provides a schematic of the GDF11/myostatin signaling cascade, highlighting both the canonical SMAD pathways and non-canonical pathways. (From Walker et al., 2016, Orig. FIGS. 1 and 2. Pg. 1128).

FIG. 7A show GDF11 Indel 13 genotyping. The gel used to genotype mice belonging to the Indel 13 line is shown. DNA from each band was separately excised from this gel (each band identified by an arrow) and was used to identify the nature of the mutation. The accompanying schematic (FIG. 7B) shows the process that led to the successful sequencing of the deletion. The bands that contained the DNA that was excised, purified, transformed, and sequenced are outlined in red. FIG. 7B provides a schematic showing the Indel 13 deletion and the predicted protein sequence.

FIG. 8A provides an image of GDF11 Indel 4A/4B Embryos—E18.5 for 4A and E17.5 for 4B—that phenocopy the characteristic GDF11 knockout phenotype: mice homozygous for the deletion are born with visibly truncated tails. FIG. 8B provides representative images of GDF11 Indel 4A/4B Embryos that have been stained with Alcian Blue (Cartilage) and Alizarin Red (Bone). Full-body images are shown for GDF11 Indel 4A, with arrows pointing to the homeotic transformations. A focus on the thoracic vertebrae for Indel 4B shows the distinct number of vertebrae for homozygous, heterozygous, and wild type mice. FIG. 8C provides a schematic of the wild-type mouse skeleton and charts for the Indel 4A/4B deletions that compare each genotype's skeletal phenotype to the skeletal phenotype of GDF11 knockout mice produced by McPherron et al. (1999). FIG. 8D shows a comparison of total vertebrae number for the different GDF11 Indel 4A/4B genotypes that shows the truncated skeleton of the homozygous mice. Due to damage to the tail of one specimen, the full vertebrae number for one WT animal could not be determined and the data point is missing.

FIG. 9A provides a schematic of primer combinations used and a table of expected values. FIG. 9B shows genotyping done with the four primer combinations, with bands that match the expected values and confirm that mice homozygous for the Indel 7 mutation are viable and living.

FIGS. 10A-10C demonstrate GDF11 Indel 7 body and organ weight analysis. FIG. 10A shows body weight was taken at time of organ harvest for mice that were between 5-6 months of age. Plots show the body weight measurements of the cohort, split by genotype. The blue symbols represent the male mice and the red symbols represent the female mice. A clear differentiation between the male and females can be seen but an ANOVA one-way analysis across genotypes did not reveal any significant differences. FIG. 10B shows plots showing the heart weight of the cohort normalized to both body weight (BW) and tibia length (TL). An additional analysis using only male mice, which normalized to tibia length was done to exclude the possibility that a mixed sex cohort led to any confounding factors. FIG. 10C shows plots showing the spleen weight of the cohort normalized to both body weight (BW) and tibia length (TL). An additional analysis using only male mice, which normalized to tibia length, was also completed. Analysis showed there were no significant differences between the genotypes.

FIG. 11A shows weight of the TA/EDL muscle was recorded for a cohort of 24 GDF11 Indel 7 mice, aged 5-7 months, and normalized to the tibia length. An ANOVA one-way test showed no significant difference between the genotypes, even when limiting the analysis to only males. FIG. 11B shows the comparison of the average of three triplicate pulls on a Columbus Grip Strength meter. An ANOVA one-way test, showed no significant difference between the genotypes. FIG. 11C shows the grip strength assay is shown here normalized to mouse weight. An ANOVA one-way test showed no significant differences, even when limiting the analysis to males.

FIG. 12A provides representative images of muscle fiber cross-sections. Two images are presented for each genotype. Scale bar shown is for 200 µm. FIG. 12B provides plot showing the average CSA of muscle fibers of each genotype. There are no significant differences among the different genotypes. FIG. 12C provides a histogram showing the relative frequency of fiber sizes. Fibers were pooled into bins of 500 µm$^2$.

FIGS. 13A-13C demonstrate quantification of circulating GDF11 and GDF8 in the cohort. FIG. 13A shows GDF11 Indel 7 protein sequence with the mutation highlighted in red and the regions used for LC/MS/MS detection highlighted in blue. The mutation does not affect the specificity or measurement of the assay. FIG. 13B shows GDF11 and GDF8 serum levels shown for a cohort of GDF11 Indel 7 mice, with a significant increase of GDF11 in the serum of Het mice. FIG. 13C shows GDF11 and GDF8 serum levels shown for a cohort of male mice, with a similar increase of GDF11 in the serum of Het male mice. There is also a difference between GDF8 serum levels in WT and Hom mice.

FIG. 14A shows 9 spleen samples, 3 of each genotype, were used to analyze the fold change in GDF11 and mRNA expression across the different genotypes in the Indel 7 cohort. Two different primer sets were used for GDF11, one that spanned Exon 1-2 and one that spanned Exon 2-3. The fold change of each individual mouse was compared with the average of the WT values. The resulting numbers were averaged according to genotype. The results of both primer sets showed a significant increase of mRNA expression in heterozygous mice and similar levels for WT and homozygous mice. FIG. 14B shows 9 kidney samples were also used for RT qPCR and showed a significant difference between WT and heterozygous samples and heterozygous and homozygous samples.

FIG. 15A provides a western blot showing lysed Thermo Fischer EXPI293™ cells 4 days after transfection with the template containing GDF11_WE_Stop. Both transfected cells show a GDF11 band, identified with the red arrows on the picture of the blot, confirming the cells were properly transfected and are producing the mutant GDF11 Indel 7 protein. Control cells that were not transfected (N-T) showed no GDF11 band. FIG. 15B shows a comparison of non-reduced and reduced western blots with the mutant Indel 7 protein shows that the monomer was already present in the non-reduced band, something not seen with the mature GDF11 protein, indicating the amino acid addition leads to a destabilization of the protein and prevents proper dimer formation. The dimer still forms, however the disulfide linkage either does not form or is destabilized, leading to the monomer to be present. A red arrow points to the presence of the monomer in non-reduced western blot. FIG. 15C shows a gel stained with coomassie stain. GDF11 is WT GDF11 from Peprotech (2 ug loaded). GDF11WE is the mutant Indel 7 protein. C4 load is the loaded sample that put onto the C4 reverse phase column for final purification (demonstrates that monomer was already present). FIG. 15D shows CagA luciferase assay showing differential binding curves between the WT GDF11 protein and the mutant Indel 7 protein. The $EC_{50}$ values are shown in the table, with the WT GDF11 having $pEC_{50}$ value of 9.035 and the mutant protein having a $pEC_{50}$ value of 8.441. The following formula was used to find the $pEC_{50}$ values: $pEC_{50} = -Log(EC_{50})$.

Figure 18:
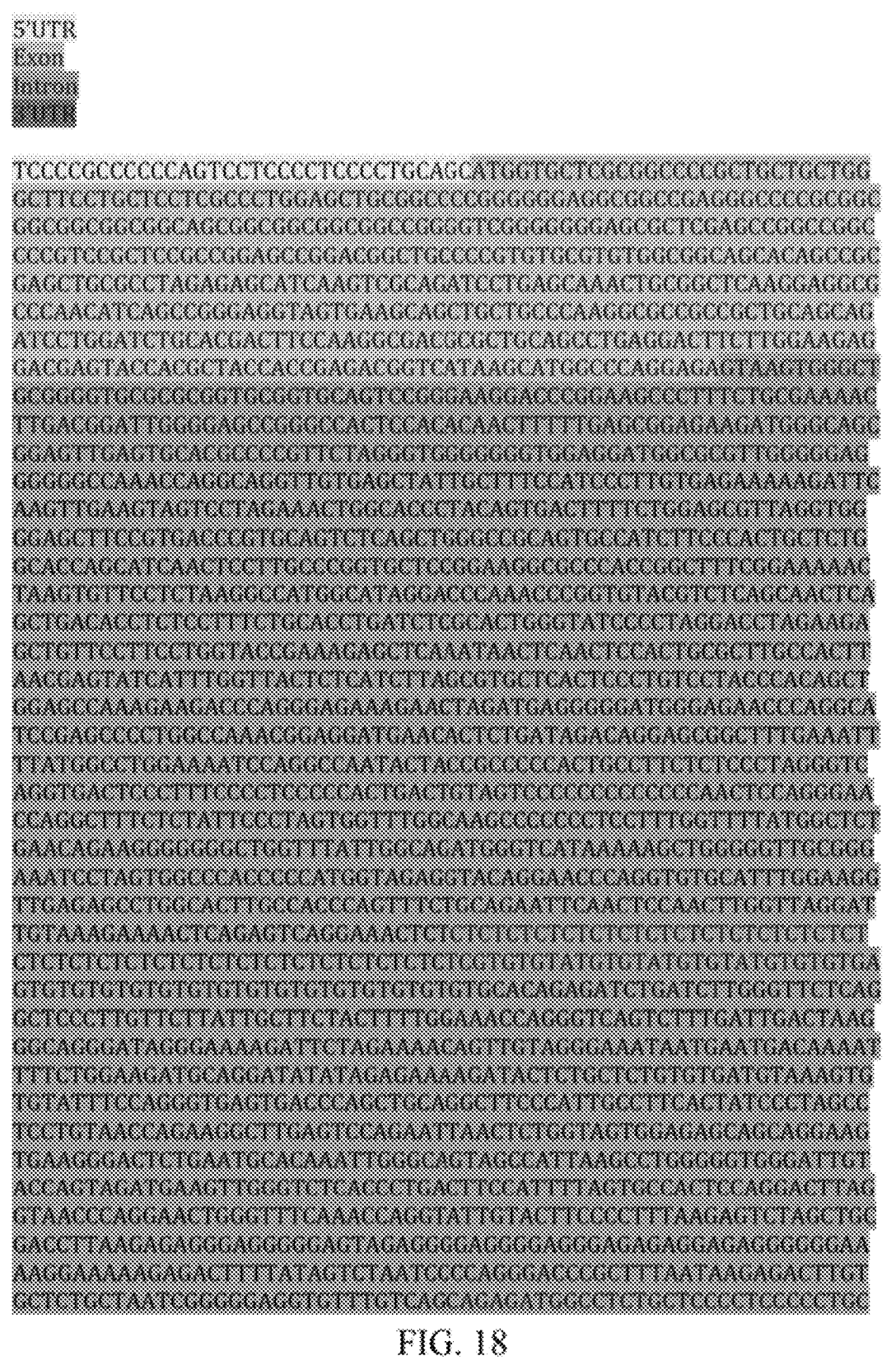
Figure 18:
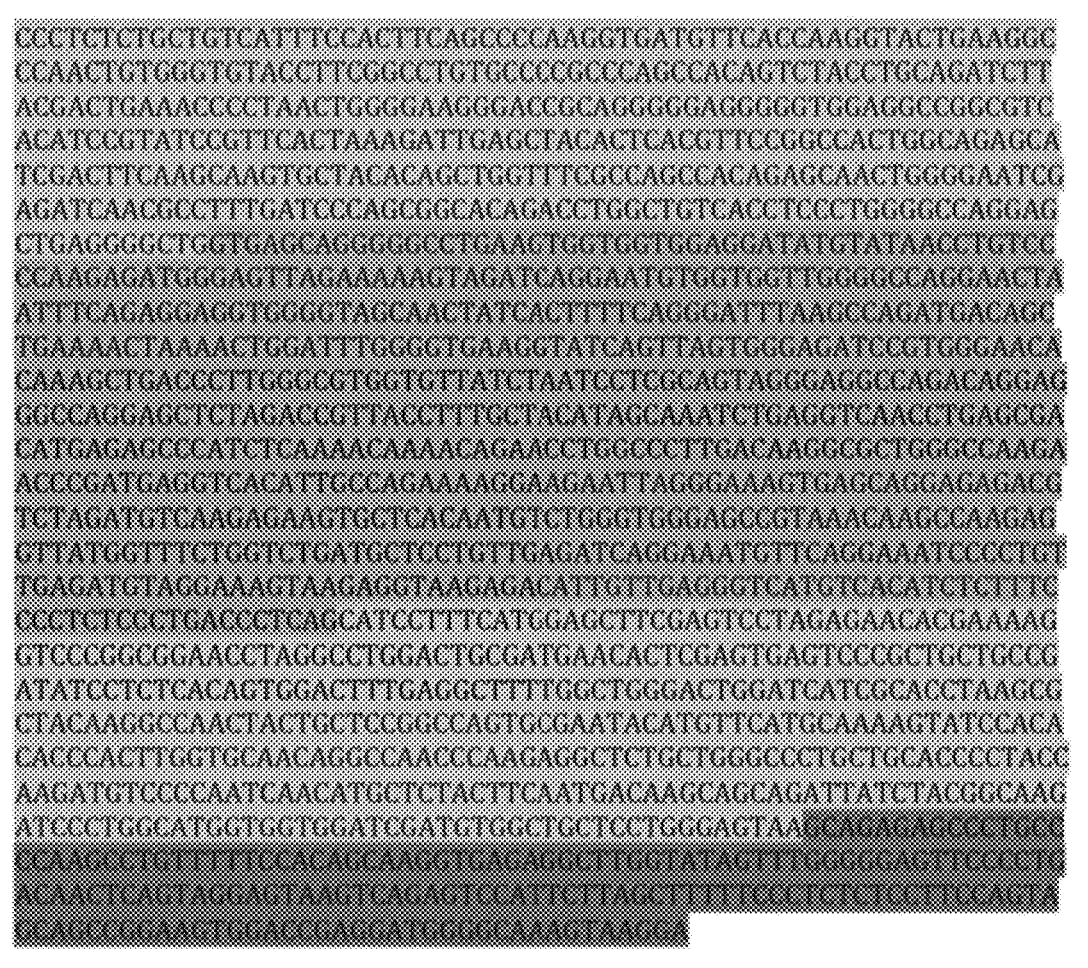

FIG. 18 provides the DNA sequence of the GDF11 Indel 7 variant (GDF11-WE variant) (SEQ ID NO: 19).

DETAILED DESCRIPTION OF THE INVENTION

Figure 1:
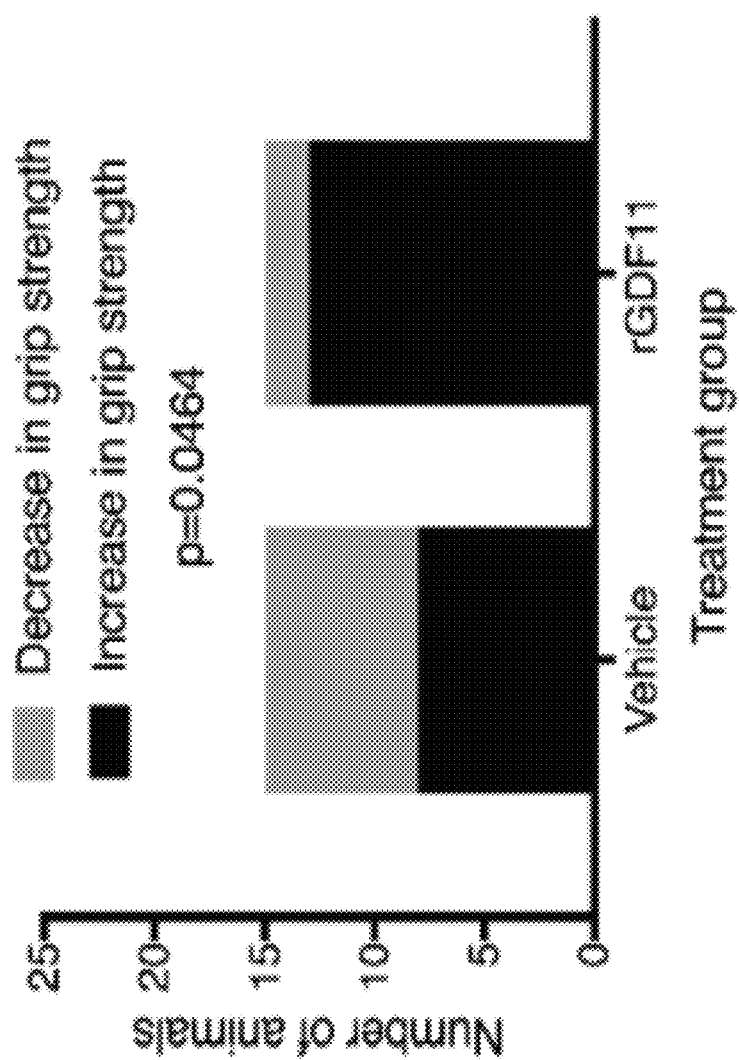
FIG. 1 shows rGDF11 supplementation protects aged rats from progressive muscle weakening. Daily injections of rGDF11 (0.1 mg/kg) or vehicle were administered into aged Sprague-Dawley rats for 28 days. Grip strength was measured at baseline and at the conclusion of the study. 47% of vehicle-treated rats showed a decrease in grip strength compared to baseline during the course of the study, while 87% of rGDF11-treated rats showed an increase (p=0.0464 by Chi Square test).

Described herein are novel candidate therapeutics (e.g., GDF11 variants) and methods utilizing, and compositions comprising, such therapeutics. The methods and compositions described herein are useful for rejuvenating the neurovascular niche (e.g., neural stem cells and/or progenitor cells), reversing decline (e.g., age-related decline) in neurogenesis and/or angiogenesis, increasing neurogenesis, increasing angiogenesis, treating or preventing neurodegenerative disorders, treating or preventing neurovascular disorders, for example, neurodegenerative disorders or neurovascular disorders associated with decreased neurogenesis and angiogenesis, respectively, due to aging. The methods and compositions described herein are also useful for increasing neuronal activity, inducing vascular remodeling, increasing neuroplasticity, increasing cognitive functioning, increasing olfactory sensitivity/behavior, or increasing neuronal stem cell and/or stem cell progenitor numbers and/or proliferation rate. The methods and compositions described herein generally relate to increasing the level of GDF11 (e.g., GDF11 polypeptide) in a subject to treat, prevent, or reverse the neurodegenerative and neurovascular disorders, conditions, and symptoms described herein. In particular embodiments the compositions and methods described herein have effect in the subventricular zone of the brain, while in other embodiments they have effect in one or more non-neurogenic regions of the brain.

The methods and compositions described herein are also useful for rejuvenating skeletal muscle stem cells, promoting skeletal muscle regeneration, improving exercise endurance, and regenerating skeletal muscle degeneration associated with an age-related disorder of skeletal muscle. The methods and compositions described herein generally relate to increasing the level of GDF11 polypeptide in a subject to treat, prevent, or reverse the skeletal muscle conditions described herein.

For convenience, certain terms employed herein are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention. Unless otherwise defined, all technical and scientific terms used herein have the meaning commonly understood by one of skill in the art.

As used herein, "neurodegenerative disorder" refers to a disease condition involving neuronal loss mediated or characterized at least partially by at least one of deterioration of neural stem cells and/or progenitor cells, a decreased capacity for neurogenesis, or a reduction in circulating GDF11 polypeptide in a subject. Non-limiting examples of neurodegenerative disorders include polyglutamine expansion disorders (e.g., HD, dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, Alzheimer disease, amyotrophic lateral sclerosis (ALS), ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, Guillain-Barré syndrome, ischemia stroke, Krabbe disease, kuru, Lewy body dementia, multiple sclerosis, multiple system atrophy, non-Huntingtonian type of Chorea, Parkinson's disease, Pelizaeus-Merzbacher disease, Pick's disease, primary lateral sclerosis, progressive supranuclear palsy, Refsum's disease, Sandhoff disease, Schilder's disease, spinal cord injury, spinal muscular atrophy (SMA), SteeleRichardson-Olszewski disease, and Tabes dorsalis.

In certain contexts, neurodegenerative disorders encompass neurological injuries or damages to the CNS or the PNS associated with physical injury (e.g., head trauma, mild to severe traumatic brain injury (TBI), spinal cord injury, diffuse axonal injury, craniocerebral trauma, cranial nerve injuries, cerebral contusion, intracerebral haemorrhage and acute brain swelling), ischemia (e.g., resulting from spinal cord infarction or ischemia, ischemic infarction, stroke, cardiac insufficiency or arrest, atherosclerotic thrombosis, ruptured aneurysm, embolism or haemorrhage), certain medical procedures or exposure to biological or chemic toxins or poisons (e.g., surgery, coronary artery bypass graft (CABG), electroconvulsive therapy, radiation therapy, chemotherapy, anti-neoplastic drugs, immunosuppressive agents, psychoactive, sedative or hypnotic drugs, alcohol, bacterial or industrial toxins, plant poisons, and venomous bites and stings), tumors (e.g., CNS metastasis, intraaxial tumors, primary CNS lymphomas, germ cell tumors, infiltrating and localized gliomas, fibrillary astrocytomas, oligodendrogliomas, ependymomas, pleomorphic xanthoastrocytomas, pilocytic astrocytomas, extraaxial brain tumors, meningiomas, schwannomas, neurofibromas, pituitary tumors, and mesenchymal tumors of the skull, spine and dura matter), infections (e.g., bacterial, viral, fungal, parasitic or other origin is selected from the group consisting of pyrogenic infections, meningitis, tuberculosis, syphilis, encephalomyelitis and leptomeningitis), metabolic or nutritional disorders (e.g., glycogen storage diseases, acid lipase diseases, Wernicke's or Marchiafava-Bignami's disease, Lesch-Nyhan syndrome, Farber's disease, gangliosidoses, vitamin B12 and folic acid deficiency), cognition or mood disorders (e.g., learning or memory disorder, bipolar disorders and depression), and various medical conditions associated with neural damage or destruction (e.g., asphyxia, prematurity in infants, perinatal distress, gaseous intoxication for instance from carbon monoxide or ammonia, coma, hypoglycaemia, dementia, epilepsy and hypertensive crises).

As used herein, "neurovascular disorder" refers to any disease or condition that results in cerebrospinal ischemia, infarction, and hemorrhage mediated or characterized at least partially by a decreased capacity for angiogenesis or a reduction in circulating GDF11 polypeptide in a subject. Neurovascular disorders encompass any abnormality of the blood vessels within or supplying the brain and spine. This includes narrowing of arteries, which reduces blood flow to the brain and increases the risk of stroke (particularly "ischemic" stroke), and weakening of arteries, which may create brain aneurysms and increases the risk of intracranial bleeding (or "hemorrhagic" stroke.) Non-limiting examples of neurovascular disorders include brain atherothrombosis, brain aneurysms, brain arteriovenous malformations, brain embolism, brain ischemia, for example caused by atherothrombosis, embolism, or hemodynamic abnormalities, cardiac arrest, carotid stenosis, cerebrovascular spasm, headache, intracranial hemorrhage, ischemic stroke, seizure, spinal vascular malformations, reflex neurovascular dystrophy (RND), neurovascular compression disorders such as hemifacial spasms, tinnitus, trigeminal neuralgia, glossopharyngeal neuralgia, stroke, transient ischemic attacks, and vasculitis.

As used herein, "skeletal muscle condition" refers to a condition in skeletal muscle mediated or characterized by a reduction in circulating GDF11 polypeptide in a subject. Non-limiting examples of skeletal muscle conditions include atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness As used herein, "frailty" is a syndrome characterized by meeting at least one of the following five attributes: unintentional weight loss, muscle weakness, slow walking speed, exhaustion, and low physical activity.

As used herein, "cachexia" means a state often associated with cancer or other serious diseases or conditions, (e.g., chronic obstructive pulmonary disease, chronic kidney disease), that is characterized by progressive weight loss, muscle atrophy and fatigue, due to the deletion of adipose tissue and skeletal muscle.

As used herein, "post-surgical muscle weakness" refers to a reduction in the strength of one or more muscles following surgical procedure. Weakness may be generalized (i.e., total body weakness) or localized to a specific area, side of the body, limb, or muscle.

As used herein, "post-traumatic muscle weakness" refers to a reduction in the strength of one or more muscles following a traumatic episode (e.g., bodily injury). Weakness may be generalized (e.g., total body weakness) or localized to a specific area, side of the body, limb, or muscle.

As used herein, "neuromuscular disease" means any disease or condition that affects any part of the nerve and muscle. Neuromuscular disease encompasses critical illness polyneuropathy, prolonged neuromuscular blockade, acute myopathy as well as acute inflammatory demyelinating polyradiculoneuropathy, amyotrophic lateral sclerosis (ALS), autonomic neuropathy, Charcot-Marie-Tooth disease and other hereditary motor and sensory neuropathies, chronic inflammatory demyelinating polyradiculoneuropathy, dermatomyositis/polymyositis, diabetic neuropathy, dystrophinopathies, endocrine myopathies, focal muscular atrophies, hemifacial spasm, hereditary neuropathies of the Charcot-Marie-Tooth disease type, inclusion body myositis, Kennedy disease, Lambert-Eaton myasthenic syndrome, muscular dystrophy (e.g., limb-girdle, Duchenne, Becker, myotonic, facioscapulohumeral, etc.), metabolic myopathies, metabolic neuropathy, multifocal motor neuropathy with conduction blocks, myasthenia gravis, neuropathy of Friedreich Ataxia, neuropathy of leprosy, nutritional neuropathy, periodic paralyses, primary lateral sclerosis, restrictive lung disease, sarcoidosis and neuropathy, Schwartz-Jampel Syndrome, spinal muscular atrophy (SMA), stiff person syndrome, thyroid disease, traumatic peripheral nerve lesions, vasculitic neuropathy, among others.

As used herein, "sarcopenia" means a loss of skeletal muscle mass, quality, and strength. Often sarcopenia is associated with aging, but may also occur in association with HIV infection and a variety of chronic conditions. Sarcopenia may lead to frailty, for example, in the elderly. Sacropenia also encompasses a condition or symptom associated with sacropenia including, but not limited to loss of skeletal muscle mass, muscle weakness, fatigue, disability, and morbidity.

The terms "decrease," "reduce," "reduced," "reduction," "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased," "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or more as compared to a reference level.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

The term "biological sample" as used herein denotes a sample taken or isolated from a biological organism, e.g., cerebral tissue, cerebrospinal fluid, blood sample, cell lysate, a homogenate of a tissue sample from a subject, or a fluid sample from a subject. Exemplary biological samples include, but are not limited to, brain biopsies, cerebrospinal fluid, or blood and/or serum samples. In some embodiments, the sample is from a resection, biopsy, or core needle biopsy. In addition, fine needle aspirate samples can be used. Samples can include paraffin-embedded and frozen tissue. The term "biological sample" also includes untreated or pretreated (or pre-processed) biological samples. In some embodiments, the biological sample is an untreated biological sample. The sample can be obtained by removing a sample of cells from a subject, but can also be accomplished by using previously isolated cells (e.g. isolated at a prior time point and isolated by the same or another person).

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein. Preferably, the subject is a mammal. The mammal can be a human, non-human primate, mouse, rat, dog, cat, horse, or cow, but are not limited to these examples. In addition, the methods described herein can be used to treat domesticated animals and/or pets. A subject can be male or female. A subject can be one who has been previously diagnosed with or identified as suffering from or having a condition in need of treatment or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition. A "subject in need" of treatment for a particular condition can be a subject having that condition, diagnosed as having that condition, or at increased risk of developing that condition relative to a given reference population.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The term "statistically significant" or "significantly" refers to statistical significance and generally means a "p" value greater than 0.05 (calculated by the relevant statistical test). Those skilled in the art will readily appreciate that the relevant statistical test for any particular experiment depends on the type of data being analyzed. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Cun-ent Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001) and Davis et al., Basic Methods in Molecular Biology, Elsevier Science Publishing, Inc., New York, USA (1995) which are both incorporated by reference herein in their entireties.

As used herein, "GDF11" refers to "Growth and Differentiation Factor 11" (NCBI Gene ID No: 10220), a member of the Transforming Growth Factor-beta superfamily of growth factors. GDF11 is known to bind TGFβ3 superfamily type I receptors including ALK4, ALK5, and ALK7. For signaling in mammalian development, GDF11 predominantly uses ALK4 and ALK5. In some embodiments, GDF11 signaling can also occur via the ACVR2B receptor. GDF11 is also closely related to GDF8 (also known as myostatin). GDF11 can also be referred to as bone morphogenic protein 11, i.e. BMP11. As used herein, "GDF11" can include the human precursor polypeptide (SEQ ID NO: 1, NCBI Ref Seq: NP_005802); the human pro-peptide (SEQ ID NO: 2); the human N-terminal polypeptide (SEQ ID NO: 4), and the human mature (SEQ ID NO: 3) forms of GDF11 as well as homologs from other species, including but not limited to bovine, dog, cat, chicken, murine, rat, porcine, bovine, turkey, horse, fish, baboon and other primates.

For human GDF11, the pro-peptide plus signal sequence (e.g. the precursor polypeptide, e.g., SEQ ID NO: 1) is 407 amino acids long. Cleavage of the 24 amino acid signal peptide generates a pro-peptide (e.g., SEQ ID NO: 2) of 383 amino acids and cleavage of the pro-peptide results in a mature GDF11 polypeptide (e.g., SEQ ID NO: 3) of 109 amino acids that corresponds to the C-terminal 109 amino acids of the pro-peptide. The mature polypeptide forms a disulfide-linked homodimer. Cleavage of the pro-peptide also generates the N-terminal polypeptide (e.g., SEQ ID NO: 4) comprising amino acids 25-298 of SEQ ID NO: 1. The N-terminal GDF11 polypeptide can antagonize the activity of, e.g., the polypeptides of SEQ ID NOs: 2 and 3, at least in vitro by forming a complex with other forms of GDF11 polypeptides and can thus be used to modulate the activity of GDF11 compositions as described herein.

As used herein, the terms "proteins" and "polypeptides" are used interchangeably to designate a series of amino acid residues connected to the other by peptide bonds between the alpha-amino and carboxy groups of adjacent residues. The terms "protein", and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when refining to a gene product and fragments thereof.

Thus, exemplary polypeptides or proteins include gene products, naturally occurring proteins, homologs, orthologs, paralogs, fragments and other equivalents, variants, fragments, and analogs of the foregoing.

As used herein, "pro-peptide" used in reference to GDF11 refers to a GDF11 polypeptide in which the signal domain (e.g. amino acids 1-24 of SEQ ID NO: 1) has been cleaved off during formation of the mature and/or active forms of GDF11. As used herein, "precursor peptide" used in reference to a GDF11 polypeptide comprising the signal domain, e.g., a polypeptide comprising the amino acid sequence of SEQ ID NO: 1.

Described herein are novel engineered proteins (e.g., GDF11 variants). A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wild type GDF11, e.g. 110%, 125%, 150%, 175%, 200%, 500%, 1000% or more.

One method of identifying amino acid residues which can be substituted is to align, for example, human GDF11 to a GDF11 homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. Similarly, alignment with a related polypeptide from the same species, e.g. GDF8, which does not show the same activity, can also provide guidance with respect to regions or structures required for GDF11 activity.

The GDF11 variant amino acid or DNA sequence can be at least 90%, at least 95%, at least 96%, at least 97%, at least 98%, at least 99%, identical to a native or reference sequence, e.g. SEQ ID NO: 4, SEQ ID NO: 3, SEQ ID NO: 1, or SEQ ID NO: 2 or a nucleic acid encoding one of those amino acid sequences. The degree of homology (percent identity) between a native and a variant sequence can be determined, for example, by comparing the two sequences using freely available computer programs commonly employed for this purpose on the World Wide Web. The variant amino acid or DNA sequence can be at least 90%, at least 91%, at least 92%, at least 93%, at least 94%, at least 95%, at least 96%, at least 97%, at least 98%, at least 99%, similar to the sequence from which it is derived (referred to herein as an "original" sequence). The degree of similarity (percent similarity) between an original and a variant sequence can be determined, for example, by using a similarity matrix. Similarity matrices are well known in the art and a number of tools for comparing two sequences using similarity matrices are freely available online, e.g. BLASTp (available on the world wide web at blast.ncbi.nlm.nih.gov), with default parameters set.

When preparing a GDF11 variant having a substitution modification, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. GDF11 variants comprising conservative amino acid substitutions can be tested in any one of the assays described herein to confirm that a desired apoptotic activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In some embodiments, the GDF11 variant administered to a subject comprises one or more amino acid additions, substitutions or modifications, particularly in the C-terminus region. In some embodiments, the substitutions and/or modifications can prevent or reduce proteolytic degradation and/or prolong half-life of the polypeptide in the subject. In some embodiments, a GDF11 native polypeptide is modified to produce a GDF11 variant by conjugating or fusing it to other polypeptide or polypeptide domains such as, by way of non-limiting example, transferrin (W006096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a GDF11 variant as described herein comprises at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta (aminoalkyl)-phenylacetic acid, thioamide, tetrazole, boronic ester, olefinic group, and derivatives thereof.

In some embodiments, a GDF11 variant as described herein comprises naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a GDF11 variant as described herein can comprise alternative amino acids. Non-limiting examples of alternative amino acids include, D-anlino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, parabenzoylphenylalanine, para-amino phenylalanine, p-fluorophenylalanine, phenylglycine, propargylglycine, sarcosine, and tert-butylglycine), diaminobutyric acid, 7-hydroxytetrahydroisoquinoline carboxylic acid, naphthylalanine, biphenylalanine, cyclohexylalanine, aminoisobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1cyclopentanecarboxylic acid, 1-amino-1-cyclohexanecarboxylic acid, amino-benzoic acid, aminonaphthoic acid, gamma-aminobutyric acid, difluorophenylalanine, nipecotic acid, alpha-anlino butyric acid, thienyl-alanine, t-butylglycine, trifluorovaline; hexafluoroleucine; fluorinated analogs; azidemodified amino acids; alkyne-modified amino acids; cyano-modified amino acids; and derivatives thereof.

In some aspects, a GDF11 variant comprises the addition of one or more amino acids to a native GDF11 polypeptide sequence. In some embodiments a variant allele of the invention modifies the coding sequence for the native protein to result in inclusion of, e.g., one, two, or three amino acids at the C-terminus. The one or more amino acids added to the sequence may be naturally occurring amino acids and/or alternative amino acids. One example of such GDF11 variant is described in the examples; the GDF11var allele modifies the coding sequence of the native protein to result in inclusion of 2 additional amino acids (tryptophan and glutamic acid) at the C-terminus of the GDF11 polypeptide sequence. In some embodiments, the GDF11 variant comprises the amino acid sequence of SEQ ID NO: 19. In other embodiments of the invention, amino acid substitutions, e.g., conservative amino acid substitutions, can be made for either or both of the tryptophan and glutamic acid added at the GDF11 C-terminus.

In some embodiments, a native GDF11 polypeptide can be modified to produce a GDF11 variant, e.g. by addition of a moiety to one or more of the amino acids comprising the peptide. In some embodiments, a GDF11 variant as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, a GDF11 variant as described herein comprises one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C terminus, introduction of C-terminal alcohol, aldehyde, ester, and thioester moieties. The half-life of a GDF11 variant can be increased by the addition of moieties, e.g. PEG or albumin.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

In certain embodiments, a GDF11 variant described herein is one in which GDF11 protein function is preserved. In some aspects, the GDF11 variant of the invention exhibits increased stability as compared to the native GDF11 protein. The GDF11 variant, when administered to a subject, may increases levels of GDF11 protein (e.g., circulating levels of GDF11 protein) in the subject.

A GDF11 variant has a coding sequence modified from that of the native GDF11 protein. In some embodiments, the variant of GDF11 is a conservatively modified variant. In some aspects, the GDF11 variant has a coding sequence with at least one modification at the ligand's C-terminus. In other aspects, the GDF11 variant has a coding sequence with at least one modification at the ligand's N-terminus. In still other aspects, the GDF11 variant has a coding sequence with at least one modification at the ligand's C-terminus and at least one modification at the ligand's N-terminus. Modifications to the coding sequence may include additions, deletions, and/or substitutions of amino acids.

In some aspects, a GDF11 variant allele encodes a polypeptide that may comprise one or more additional amino acids to a native GDF11 sequence. In some aspects, the GDF11 variant allele encodes a polypeptide comprising at least one, at least two, at least three, at least four, at least five, or at least six additional amino acids. In certain aspects, additional amino acids are located at the ligand's C-terminus, the ligand's N-terminus, or both the ligand's C- and N-terminus. In some embodiments, the GDF11 variant comprises the addition of at least one, at least two, at least three, at least four, at least five, or at least six amino acids at the C-terminus of a GDF11 native sequence. In some embodiments, the GDF11 variant comprises the addition of at least one, at least two, at least three, at least four, at least five, or at least six amino acids at the N-terminus of a GDF11 native sequence. The one or more amino acids added to the GDF11 native sequence may be naturally occurring amino acids and/or alternative amino acids.

A GDF11 variant allele may comprise at least one additional amino acid to the native GDF11 sequence at the ligand's C-terminus. Alternatively, a GDF11 variant allele may comprise at least one additional amino acid to the native GDF11 sequence at the ligand's N-terminus. In some aspects, the at least one additional amino acid is a naturally occurring amino acid. The naturally occurring amino acid may be selected from the group consisting of Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some aspects, the at least one additional amino acid is tryptophan. In other aspects, the at least one additional amino acid is glutamic acid. In still other aspects, the GDF11 variant allele comprises at least two additional amino acids to the native GDF11 sequence at the ligand's C-terminus. The at least two additional amino acids may comprise glutamic acid and tryptophan. In certain embodiments, a GDF11 variant allele comprises the addition of tryptophan and glutamic acid to the native GDF11 sequence at the ligand's C-terminus.

In some embodiments, the level of GDF11 in a subject is increased by administering a GDF11 variant, as described herein. The administered GDF11 variant may increase the level or activity of native GDF11 in the subject. In other embodiments, the level of GDF11 in a subject is increased by administering a composition comprising a GDF11 variant and a pharmaceutically acceptable carrier. The composition may further comprise one or more other agents that increase GDF11 levels. For example, the composition may comprise a GDF11 variant, pharmaceutically acceptable carrier, and one or more of a GDF11 agonist, a GDF11 agonist antibody that increases expression of GDF11 in the subject, a GDF11 polypeptide, or a nucleic acid encoding a GDF11 polypeptide.

In some embodiments, the level of GDF8 in a subject is increased by administering a GDF11 variant, as described herein. The administered GDF11 variant may increase the level or activity of native GDF8 in the subject. In other embodiments, the level of GDF8 in a subject is increased by administering a composition comprising a GDF11 variant and a pharmaceutically acceptable carrier. The composition may further comprise one or more other agents that increase GDF8 levels. For example, the composition may comprise a GDF11 variant, pharmaceutically acceptable carrier, and one or more of a GDF8 agonist, a GDF8 agonist antibody that increases expression of GDF8 in the subject, a GDF8 polypeptide, or a nucleic acid encoding a GDF8 polypeptide.

In some embodiments, a GDF11 variant as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biophamzaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11,:345-365; Gaignault et al. (1996) "Designing Prodrugs and Bioprecursors I. Carrier Prodrugs," *Pract. Med. Chern.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivel)' Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs-principle and applicability to improve the therapeutic effects of drugs", *Arch. Pharm. Chemi* 86(1): 1-39 (1979); Bundgaard H. "Improved drug delivery by the prodrug approach", *Controlled Drug Delively* 17: 179-96 (1987); Bundgaard H. "Prodrugs as a means to improve the delivery of peptide drugs", Arfv. *Drug Delivel)' Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxybenzyl) Methylphosphonate with Carboxyesterase," *Chern. Soc., Chern. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biophamz. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Deliva}' Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), which are incorporated by reference herein in their entireties.

In some embodiments, a GDF11 variant as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chern. Soc. 85:2149 (1964); Bodanszky, M., Principles of Peptide Synthesis, Springer-Verlag, New York, N.Y. (1984); Kirnrnerlin, T. and Seebach, D. J. Pept. Res. 65:229-260 (2005); Nilsson et al., Annu. Rev. Biophys. Biornol. Struct. (2005) 34:91-118; W. C. Chan and P. D. White (Eds.) Frnoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, 2nd Ed, Oxford University Press, Cary, N.C. (2002); and P. Lloyd-Williams, F. Albericio, and E. Giralt, Chemical Approaches to the synthesis of pep tides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a GDF11 variant as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double stranded DNA. Alternatively, it can be a single-stranded nucleic acid not derived from any double stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA. The nucleic acid molecule can be naturally occurring, as in genomic DNA, or it may be synthetic, i.e., prepared based upon human action, or may be a combination of the two. The nucleic acid molecule can also have certain modification such as 2'-deoxy, 2'-deoxy-2'fluoro, 2'-0-methyl, 2'-0-methoxyethyl (2'-0-MOE), 2'-0-aminopropyl (2'-0-AP), 2'-0-dimethylaminoethyl (2'-0-DMAOE), 2'-0-dimethylaminopropyl (2'-0-DMAP), 2'-0-dimethylaminoethyloxyethyl (2'-0-DMAEOE), or 2'-0-N-methylacetamido (2'-0-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some aspects, a composition comprises a GDF11 variant. In other aspects, a pharmaceutical composition or kit for use in increasing GDF11 levels in a subject comprises a GDF11 variant.

The preparation of a pharmacological composition that contains active ingredients dissolved or dispersed therein is well understood in the art and generally need not be limited based on formulation. Typically such compositions are prepared as injectable either as liquid solutions or suspensions, however, solid forms suitable for solution, or suspension, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents, and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline.

Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, a GDF11 variant as described herein can be administered by controlled- or delayed-release means. Controlled release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled-release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like.

Advantageously, controlled-release formulations can be used to control a drug's onset of action, duration of action, plasma levels within the therapeutic window, and peak blood levels. In particular, controlled or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B 1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the technology described herein relates to a syringe comprising a therapeutically effective amount of a composition e.g. a pharmaceutical preparation comprising a GDF11 variant as described herein.

As used herein, the phrase "therapeutically effective amount", "effective amount" or "effective dose" refers to an amount that provides a therapeutic or aesthetic benefit in the treatment, prevention, or management of a disorder or disease, e.g., an amount that provides a statistically significant decrease in at least one symptom, sign, or marker of the disorder or disease.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In some aspects, the technology described herein relates to a method comprising administering a GDF11 variant to a subject. In some embodiments, the subject is in need of treatment for a disorder or disease that exhibits reduced GDF11 levels. In some embodiments, the method is a method of treating a subject.

As used herein, "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state as compared to that expected in the absence of treatment.

As used herein, the term "administering," refers to the placement of the composition comprising a GDF11 variant as disclosed herein into a subject by a method or route which results in delivery to a site of action. The pharmaceutical composition comprising a GDF11 variant can be administered by any appropriate route which results in an effective treatment in the subject.

Data described herein indicate that systemic administration via the vascular system can be effective. Thus administration via the intravenous route is specifically contemplated. However, with appropriate formulation, other routes are contemplated, including, for example, intranasally, intraarterially; intra-coronary arterially; orally, by inhalation, intraperitoneally, intramuscularly, subcutaneously, intracavity, or by other means known by those skilled in the art. The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The dosage ranges for the agent depends upon the potency, and are amounts large enough to produce the desired effect. The dosage should not be so large as to cause unacceptable adverse side effects.

Generally, the dosage will vary with the age, condition, and sex of the patient and can be determined by one of skill in the art. The dosage can also be adjusted by the individual physician in the event of any complication. Typically, the dosage can range from 0.001 mg/kg body weight to 0.5 mg/kg body weight. In one embodiment, the dose range is from 5 μg/kg body weight to 30 μg/kg body weight.

Administration of the doses recited above can be repeated. In some embodiments, the doses are given once a day, or multiple times a day, for example, but not limited to, three times a day. In some embodiments, the doses recited above are administered daily for weeks or months. The duration of treatment depends upon the subject's clinical progress and responsiveness to therapy. Without wishing to be bound by theory, where the GDF11 polypeptide apparently diminishes with age in affected individuals, it is expected that long-term therapy would be required to establish and maintain the benefit of GDF11-based treatment.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent administration. Alternatively, continuous intravenous infusion sufficient to maintain concentrations in the blood in the ranges specified for in vivo therapies are contemplated. In some embodiments, the dosage range is sufficient to maintain concentrations in the blood in the range found in the blood of a population of normal, healthy human subjects under the age of 50. In some embodiments, the dosage range is sufficient to maintain concentrations in the blood in the range found in normal, healthy human subjects under the age of 40. In some embodiments, the dosage range is sufficient to maintain concentrations in the blood in the range found in normal, healthy human subjects under the age of 30. In some embodiments, the dosage range is sufficient to maintain concentrations in the blood in the range found in normal, healthy human subjects under the age of 25. In some embodiments, the dosage range is sufficient to maintain concentrations in the blood in the range found in normal, healthy human subjects under the age of 21.

A therapeutically effective amount is an amount of an agent that is sufficient to produce a statistically significant, measurable change in a disorder. Such effective amounts can be gauged in clinical trials as well as animal studies. Efficacy of an agent can be determined by assessing physical indicators. In experimental systems, assays for efficacy are well known in the art. In addition, efficacy of an agent can be measured by an increase in GDF11 polypeptides or fragments thereof in a subject being treated with an agent comprising a GDF11 variant.

The efficacy of a given treatment for a disorder or disease can be determined by the skilled clinician. However, a treatment is considered "effective treatment," as the term is used herein, if any one or all of the signs or symptoms of a disorder are altered in a beneficial manner, other clinically accepted symptoms are improved or ameliorated, e.g., by at least 10% following treatment with an agent or composition as described herein. Efficacy can also be measured by a failure of an individual to worsen as assessed by hospitalization or need for medical interventions (i.e., progression of the disease is halted). Methods of measuring these indicators are known to those of skill in the art and/or described herein.

In some embodiments, the methods further comprise administering the pharmaceutical composition described herein along with one or more additional agents, biologics, drugs, or treatments beneficial to a subject suffering from a disorder or disease.

The above other therapeutic agents, when employed in combination with the chemical entities described herein, may be used, for example, in those amounts indicated in the Physicians' Desk Reference (PDR) or as otherwise determined by one of ordinary skill in the art.

Described herein are methods comprising administering to a subject an agent or composition (e.g., a GDF11 variant) which increases the level of GDF11 polypeptide in the subject. Additional aspects of the invention include the use of a GDF11 variant in any method in which increasing the level of GDF11 polypeptide is desirable, including those methods described in US Publication No. 2016/0220640; US Publication No. 2016/0074477; US Publication No. 2016/0287667; Sinha et al., Science 2014 344(6184):649-652; Katsimpardi et al., Science 2014 344(6184):630-634; Loffredo et al., Cell 2013 153:828-839; which are incorporated by reference herein in their entirety.

Methods and Compositions for Increasing Neurogenesis and Angiogenesis

Described herein are methods comprising administering to a subject an agent or composition which increases the level of GDF11 polypeptide in the subject, wherein the agent or composition comprises a GDF11 variant. In some embodiments, the subject is one who is in need of rejuvenated neural stem cells and/or progenitor cells. As used herein "rejuvenated neural stem cells and/or progenitor cells" and "rejuvenating neural stem and/or progenitor cells" refer to a restoration of the neural stem cells and/or progenitor cells either partially or wholly to the quality and/or quantity of neural stem cells and/or progenitor cells typically found within a youthful healthy subject of the same species. In some embodiments, the number of neural stem cells and/or progenitor cells are restored completely to the number of neural stem cells and/or progenitor cells of a youthful healthy subject of the same species. In some embodiments, the number of neural stem cells and/or progenitor cells in the subject are restored to within 95%, to within 90%, to within 85%, to within 80%, to within 75%, to within 70%, to within 65%, to within 60%, to within 55%, or to within 50% of the number of neural stem cells and/or progenitor cells of a youthful subject. In some contexts, "rejuvenated neural stem cells and/or progenitor cells" and "rejuvenating neural stem cells and/or progenitor cells" refers to an increase in the number or frequency of the neural stem cells and/or progenitor cells" in the subject compared to a number or frequency of the neural stem and/or progenitor cells before administration of an agent or composition which increased the level of GDF11 polypeptide in the subject. In some embodiments, the number or frequency of neural stem cells and/or progenitor cells are increased by at least 10% in the subject. In some embodiments, the number or frequency of neural stem cells and/or progenitor cells are increased by at least 15% in the subject. In some embodiments, the number or frequency of neural stem cells and/or progenitor cells are increased by at least 20% in the subject. In some embodiments, the number or frequency of neural stem cells and/or progenitor cells are increased by at least 25% in the subject. In some embodiments, the number or frequency of neural stem cells and/or progenitor cells are increased by at least 30% in the subject. In some embodiments, the number or frequency of neural stem cells and/or progenitor cells are increased by at least 35% in the subject. In some embodiments, the number or frequency of neural stem cells and/or progenitor cells are increased by at least 40% in the subject. In some embodiments, the number or frequency of neural stem cells and/or progenitor cells are increased by at least 45% in the subject. In some embodiments, the number or frequency of neural stem cells and/or progenitor cells are increased by at least 50% in the subject. In some embodiments, the number or frequency of neural stem cells and/or progenitor cells are increased by at least 60%, at least 65%, at least 70%, at least 75%, at least 80%, or at least 90% in the subject. In some embodiments, the number or frequency of neural stem cells and/or progenitor cells are increased by at least 100% in the subject. In some embodiments, the number or frequency of neural stem cells and/or progenitor cells are increased by at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 3 fold, at least 4 fold, at least 5 fold, at least 10 fold or more in the subject.

In some embodiments, the subject is one who is in need of increased neurogenesis. In some embodiments, the subject is one who has, or has been diagnosed as having a neurodegenerative disorder. In some embodiments, the subject is one who has, or has been diagnosed as having a neurodegenerative disorder characterized by decreased neurogenesis. In some embodiments, the subject is one who has, or has been diagnosed as having a neurodegenerative disorder characterized at least partially by a decreased capacity for neurogenesis due to aging. In some embodiments, the subject is one who is at risk of developing a neurodegenerative disorder due to aging. In some embodiments, the subject is one who has, or has been diagnosed as having, or is at risk of developing, dementia. In some embodiments, the subject is one who has, or has been diagnosed as having, or is at risk of developing, Alzheimer's disease. In some embodiments, the subject is one who has, or has been diagnosed as having, or is at risk of developing, mild cognitive impairment. In some embodiments, the subject is one who has, or has been diagnosed as having, or is at risk of developing, depression. In some embodiments, the subject is one who has, or has been diagnosed as having, or is at risk of developing, a learning disorder. In some embodiments, the subject is one who has, or has been diagnosed as having, or is at risk of developing, a memory disorder.

In some embodiments, the subject is one who is in need of increased angiogenesis. In some embodiments, the subject is one who has, or has been diagnosed as having a neurovascular disorder. In some embodiments, the subject is one who has, or has been diagnosed as having a neurovascular disorder characterized by decreased angiogenesis. In some embodiments, the subject is one who has, or has been diagnosed as having a neurovascular disorder characterized at least partially by a decreased capacity for angiogenesis due to aging. In some embodiments, the subject is one who is at risk of developing a neurovascular disorder due to aging. In some embodiments, the subject is one who has, or has been diagnosed as having, or is at risk of developing, stroke. In some embodiments, the subject is one who has, or has been diagnosed as having, or is at risk of developing, ischemia.

In some embodiments, the subject is an elderly subject. In some embodiments, an elderly subject is over the age of 50, 55, 60, 65, 70, 75, 80, 85, 90, or 100 years.

In some embodiments, the agent or composition which increases the level of GDF11 polypeptide is administered to a subject who has or has been diagnosed with a neurodegenerative disorder described herein. A health care professional may diagnose a subject as having a neurodegenerative disorder by the assessment of one or more symptoms of a neurodegenerative disorder in the subject. Non-limiting symptoms of a neurodegenerative disorder in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite. A health care professional may also base a diagnosis, in part, on the subject's family history of a neurodegenerative disorder. A health care professional may diagnose a subject as having a neurodegenerative disorder upon presentation of a subject to a health care facility (e.g., a clinic or a hospital). In some instances, a health care professional may diagnose a subject as having a neurodegenerative disorder while the subject is admitted in an assisted care facility. Typically, a physician diagnoses a neurodegenerative disorder in a subject after the presentation of one or more symptoms.

In some embodiments, the agent or composition which increases the level of GDF11 polypeptide is administered to a subject who has or has been diagnosed with a neurological injury or damage to the CNS or the PNS associated with physical injury, ischemia, certain medical procedures or exposure to biological or chemical toxins or poisons, tumors, infections, metabolic or nutritional disorders, cognition or mood disorders, and various medical conditions associated with neural damage or destruction described herein.

In some embodiments, the agent or composition which increases the level of GDF11 polypeptide is administered to a subject who has or has been diagnosed with a neurovascular disorder described herein. A health care professional may diagnose a subject as having a neurovascular disorder by the assessment of one or more symptoms of a neurovascular disorder in the subject. Non-limiting symptoms of a neurovascular disorder in a subject include hypertension, platelet aggregation, altered cerebrovascular architecture (e.g., narrowing, stiffness, deformation), sudden blood pressure shifts, facial weakness, visual impairment, loss of coordination, or balance, a sudden headache, and mental confusion with unintelligible speech.

In some embodiments, the agent or composition which increases the level of GDF11 polypeptide is administered to a subject who is at risk of developing a neurovascular disorder described herein. A subject who is at risk of developing a neurovascular disorder includes individuals who are elderly, have a history of diabetes, smoking, or ischemic heart disease, for example.

In some embodiments, the level of GDF11 polypeptide is the level of GDF11 in the systemic circulation of a subject. In some embodiments, the level of GDF11 polypeptide is the level of GDF11 in the cerebral vasculature of a subject. In some embodiments, the level of GDF11 polypeptide is the level of GDF11 in the neurovasculature of a subject. In some embodiments, the level of GDF11 polypeptide is the level of GDF11 in the cerebral tissue of a subject. In some embodiments, the level of GDF11 polypeptide is the level of GDF11 in the cerebrospinal fluid of a subject. In some embodiments, the level of GDF11 polypeptide is the level of GDF11 in the lateral ventricles of a subject. In some embodiments, the level of GDF11 polypeptide is the level of GDF11 in the subventricular zone neurovascular niche of a subject.

The level of GDF11 in a subject can be determined by obtaining a biological sample from the subject and determining the level of GDF11 in the biological sample. Methods for determining the level of a polypeptide in a subject or a sample obtained from a subject are well known in the art and include, but are not limited to, ELISA, radioimmunoassay, immunohistochemistry, methods involving a labeled antibody specific for GDF11, dot blot analysis, functional bioassays, Northern blot, in-situ hybridization, and RT-PCR, aptamer-based proteomic technology (e.g., SOMAscan™ commercially available from SomaLogic, Inc.) among others. Antibodies specific for GDF11 are commercially available, e.g. Cat. No. ab71347 from Abcam: Cambridge, Mass. In some embodiments, the antibodies are antibodies which do not cross-react with GDF8. In some embodiments, the antibodies are selective GDF11 monoclonal antibodies. In some embodiments, the level of GDF11 polypeptide is determined by measuring the level of an mRNA encoding a GDF11 polypeptide. In some embodiments, the level of GDF11 can be measured as described in Souza et al., Molecular Endocrinology 2008 22:2689-2702; which is incorporated by reference herein in its entirety.

As animals age, neural stem cell and/or progenitor cells deteriorate (e.g., decrease in number or function) and animals exhibit diminished capacity for neurogenesis and decreased neuroplasticity, which is often accompanied with cognitive decline associated with one or more neurodegenerative disorders (e.g., dementia). Without wishing to be bound by theory, it is believed that deterioration of neural stem and/or progenitor cells and characteristic attendant reduced neurogenesis results in part from decreased levels of circulating GDF11 polypeptide. Accordingly, in one aspect, the present invention provides a method of rejuvenating neural stem cells and/or progenitor cells in a subject in need thereof, comprising administering to the subject an agent or composition which increases the level of GDF11 polypeptide in the subject. In some embodiments, the agent or composition causes the subject's neural stem cells and/or progenitor cells to undergo at least one of an increase in frequency or number, proliferation, differentiation, and an increase in neurogenesis.

In another aspect, the present invention provides a method for increasing neurogenesis in a subject in need thereof, comprising administering to the subject an agent or composition which increases the level of GDF11 polypeptide in the subject, thereby increasing neurogenesis in the subject. In some embodiments, increasing neurogenesis is associated with increased neural cell proliferation, increased neural cell differentiation, increased number or frequency of neural stem cells, increased number of neural progenitor cells, increased number of neural precursor cells, and increased expression of at least one synaptic plasticity gene, at least one neuroprotective gene, or at least one neuronal specification gene selected from the group consisting of neuronal PAS domain protein 4 (Npas4) (NCBI Gene ID: 266743), dual specificity phosphatase 1 (Dusp1) (NCBI Gene ID: 1843), heat shock 70 kDa protein 8 (Hspa8) (NCBI Gene ID: 3312), BTG family, member 2 (Btg2) (NCBI Gene ID: 7832), activity-regulated cytoskeleton-associated protein (Arc) (NCBI Gene ID: 23237), nuclear receptor subfamily 4, group A, member 1 (Nr4a1) (NCBI Gene ID: 3164), cysteine-rich, angiogenic inducer, 61 (Cyr61) (NCBI Gene ID: 3491), FBJ murine osteosarcoma viral oncogene homolog (Fos) (NCBI Gene ID: 2353), jun B proto-oncogene (Junb) (NCBI Gene ID: 3726), Kruppel-like factor 10 (Klf10) (NCBI Gene ID: 7071), nuclear receptor subfamily 4, group A, member 2 (Nr4a2) (NCBI Gene ID: 4929), claudin 1 (Cldn1) (NCBI Gene ID: 9076), early growth response 2 (Egr2) (NCBI Gene ID: 1959), crystalline, mu (Crym) (NCBI Gene ID: 1428), early growth response 1 (Egr1) (NCBI Gene ID: 1958), and polio-like kinase 2 (Plk2) (NCBI Gene ID: 10769), and increasing the number of new neurons. In some embodiments, neurogenesis is increased in the subventricular zone of the lateral ventricles. In some embodiments, neurogenesis is increased in the olfactory bulb. In some embodiments, increased neurogenesis results in improved olfactory behavior.

In another aspect, the present invention provides a method for increasing angiogenesis in a subject in need thereof, comprising administering to the subject an agent or composition which increases the level of GDF11 polypeptide in the subject, thereby increasing angiogenesis in the subject. In some embodiments, increasing angiogenesis comprises increasing cerebrovascular architecture, increasing capillary density, increasing cerebral blood flow, and increasing cerebral vessel sprouting branch points.

In some embodiments the level of GDF11 in the subject is increased by at least 20% over the level of GDF11 in the subject prior to treatment, e.g. 20% or more, 30% or more, 40% or more, 50% or more, 100% or more, 150% or more, 200% or more, 250% or more, 300% or more, or 350% or more. In some embodiments the level of GDF11 in the subject is increased by at least 100% over the level of GDF11 in the subject prior to treatment. In some embodiments the level of GDF11 in the subject is increased by at least 200% over the level of GDF11 in the subject prior to treatment. In some embodiments the level of GDF11 in the subject is increased by about 250% over the level of GDF11 in the subject prior to treatment. In some embodiments, the level of GDF11 in the subject is increased to at least 50% of a healthy reference level, e.g. 50% or more, 60% or more, 70% or more, 80% or more, 90% or more, or 100% or more of a healthy reference level. In some embodiments, the level of GDF11 in the subject is increased to at least 60% of a healthy reference level. In some embodiments, the level of GDF11 in the subject is increased to at least 75% of a healthy reference level. In some embodiments, the level of GDF11 in the subject is increased to at least 90% of a healthy reference level. A healthy reference level can be the average level of GDF11 in a population of human subjects (e.g., young individuals) not exhibiting any signs or symptoms of neural stem cell and/or progenitor cell deterioration, diminished capacity for neurogenesis, or related conditions.

As used herein, "neural stem cell and/or progenitor cell deterioration" refers to a decrease in cell number or frequency of neural stem cells and/or progenitor cells.

In some embodiments, a healthy reference level can be the average level of GDF11 in a population of human subjects not exhibiting any signs or symptoms of neural stem cell and/or progenitor deterioration, diminished capacity for neurogenesis or related conditions and who are under the age of 70. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 65. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 60. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 55. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 50. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 45. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 40. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 35. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 30. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 25. In some embodiments, a healthy reference level can be the average level of GDF11 in a population of human subjects not exhibiting any signs or symptoms of neural stem cell and/or progenitor deterioration, diminished capacity for neurogenesis, or related conditions and who are under the age of 20.

In some embodiments, the methods described herein can comprise selecting a subject with a level of GDF11 which is lower than a healthy reference level and administering a treatment as described herein.

In some embodiments, the level of GDF11 in a subject is increased in order to treat a neurodegenerative disorder (e.g., Alzheimer's disease, dementia, mild cognitive decline, etc.) or neurological injury or damage to the CNS or the PNS associated with physical injury, ischemia, certain medical procedures or exposure to biological or chemic toxins or poisons, tumors, infections, metabolic or nutritional disorders, cognition or mood disorders, and various medical conditions associated with neural damage or destruction described herein. In some embodiments, the level of GDF11 in a subject is increased in order to treat a neurodegenerative disorder associated with decreased neurogenesis. In some embodiments, the level of GDF11 in a subject is increased in order to treat a neurodegenerative disorder by increasing neurogenesis in a subject. In some embodiments, the level of GDF11 in a subject is increased in order to prevent a neurodegenerative disorder or neurological injury or damage to the CNS or the PNS associated with physical injury, ischemia, certain medical procedures or exposure to biological or chemic toxins or poisons, tumors, infections, metabolic or nutritional disorders, cognition or mood disorders, and various medical conditions associated with neural damage or destruction described herein.

In some embodiments, the level of GDF11 in a subject is increased in order to treat a neurovascular disorder (e.g., stroke). In some embodiments, the level of GDF11 in a subject is increased in order to treat a neurovascular disorder associated with decreased angiogenesis. In some embodiments, the level of GDF11 in a subject is increased in order to treat a neurovascular disorder by increasing angiogenesis in a subject. In some embodiments, the level of GDF11 in a subject is increased in order to prevent a neurovascular disorder (e.g., stroke).

Neurodegenerative or neurovascular disorders related to low or decreased GDF11 polypeptide tend to develop with the decrease in GDF11 levels that occur with increasing age. Thus, it is expected that such conditions can be prevented or, at a minimum, delayed, by maintaining GDF11 polypeptide levels at or near the level found in normal, healthy young adults, e.g., by administering a GDF11 polypeptide or a nucleic acid encoding a GDF11 polypeptide with advancing age, but prior to the onset of a neurodegenerative or neurovascular disorder.

In another aspect, the present invention provides a method for treating or preventing a disorder associated with diminished capacity for neurogenesis in a subject, comprising administering to the subject an effective amount of an agent or composition which increases the level of GDF11 polypeptide in the subject, thereby increasing neurogenesis in the subject, wherein increasing neurogenesis in the subject treats or prevents the disorder associated with diminished capacity for neurogenesis in the subject.

In another aspect, the present invention provides a method for treating or preventing a neurodegenerative disorder in a subject, comprising administering to the subject an effective amount of an agent or composition which increases the level of GDF11 polypeptide in the subject, thereby treating the neurodegenerative disorder in the subject.

In another aspect, the present invention provides a method for treating or preventing a neurodegenerative disorder by increasing neurogenesis in a subject, comprising administering to the subject an effective amount of an agent or composition which increases the level of GDF11 polypeptide in the subject, thereby increasing neurogenesis in the subject, wherein increasing neurogenesis in the subject treats or prevents the neurodegenerative disorder in the subject. In some embodiments of this and other aspects disclosed herein, increasing neurogenesis is associated with increasing neural cell proliferation, increasing neural cell differentiation, increasing the number of neural stem cells, increasing the number of neural progenitor cells, increasing the number of neural precursor cells, increasing expression of at least one synaptic plasticity gene, at least one neuroprotective gene, or at least one neuronal specification gene selected from the group consisting of neuronal PAS domain protein 4 (Npas4) (NCBI Gene ID: 266743), dual specificity phosphatase 1 (Dusp1) (NCBI Gene ID: 1843), heat shock 70 kDa protein 8 (Hspa8) (NCBI Gene ID: 3312), BTG family, member 2 (Btg2) (NCBI Gene ID: 7832), activity-regulated cytoskeleton-associated protein (Arc) (NCBI Gene ID: 23237), nuclear receptor subfamily 4, group A, member 1 (Nr4a1) (NCBI Gene ID: 3164), cysteine-rich, angiogenic inducer, 61 (Cyr61) (NCBI Gene ID: 3491), FBJ murine osteosarcoma viral oncogene homolog (Fos) (NCBI Gene ID: 2353), jun B proto-oncogene (Junb) (NCBI Gene ID: 3726), Kruppel-like factor 10 (Klf10) (NCBI Gene ID: 7071), nuclear receptor subfamily 4, group A, member 2 (Nr4a2) (NCBI Gene ID: 4929), claudin 1 (Cldn1) (NCBI Gene ID: 9076), early growth response 2 (Egr2) (NCBI Gene ID: 1959), crystalline, mu (Crym) (NCBI Gene ID: 1428), early growth response 1 (Egr1) (NCBI Gene ID: 1958), and polio-like kinase 2 (Plk2) (NCBI Gene ID: 10769), and increasing the number of new neurons In some embodiments, neurogenesis is increased in the subventricular zone of the lateral ventricles. In some embodiments, neurogenesis is increased in the olfactory bulb. In some embodiments, increased neurogenesis results in improved olfactory behavior.

In some embodiments, the neurodegenerative disorder is one of polyglutamine expansion disorders (e.g., HD, dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, Alzheimer disease, amyotrophic lateral sclerosis (ALS), ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, Guillain-Barré syndrome, ischemia stroke, Krabbe disease, kuru, Lewy body dementia, multiple sclerosis, multiple system atrophy, non-Huntingtonian type of Chorea, Parkinson's disease, Pelizaeus-Merzbacher disease, Pick's disease, primary lateral sclerosis, progressive supranuclear palsy, Refsum's disease, Sandhoff disease, Schilder's disease, spinal cord injury, spinal muscular atrophy (SMA), SteeleRichardson-Olszewski disease, and Tabes dorsalis.

In some embodiments, the neurodegenerative disorder comprises a neurological injury or damage to the CNS or the PNS associated with physical injury, ischemia, certain medical procedures or exposure to biological or chemic toxins or poisons, tumors, infections, metabolic or nutritional disorders, cognition or mood disorders, and various medical conditions associated with neural damage or destruction described herein.

In another aspect, the present invention provides a method for treating or preventing a neurovascular disorder, comprising administering to the subject an agent or composition which increases the level of GDF11 polypeptide in the subject, thereby treating or preventing the neurovascular disorder in the subject.

In another aspect, the present invention provides a method for treating or preventing a neurovascular disorder by increasing angiogenesis in a subject, comprising administering to the subject an agent or composition which increases the level of GDF11 polypeptide in the subject, thereby increasing angiogenesis in the subject, wherein increasing angiogenesis in the subject treats or prevents the neurovascular disorder in the subject. In some embodiments of this and other aspects disclosed herein, increasing angiogenesis comprises increasing cerebrovascular architecture, increasing capillary density, increasing cerebral blood flow, and increasing cerebral vessel sprouting branch points.

In some embodiments, the neurovascular disorder is selected from the group consisting of brain atherothrombosis, brain aneurysms, brain arteriovenous malformations, brain embolism, brain ischemia, for example caused by atherothrombosis, embolism, or hemodynamic abnormalities, cardiac arrest, carotid stenosis, cerebrovascular spasm, headache, intracranial hemorrhage, ischemic stroke, seizure, spinal vascular malformations, reflex neurovascular dystrophy (RND), neurovascular compression disorders such as hemifacial spasms, tinnitus, trigeminal neuralgia, glossopharyngeal neuralgia, stroke, transient ischemic attacks, and vasculitis.

Aspects of the technology described herein relate to agents and which increase levels of GDF11 polypeptide (e.g., compositions comprising a GDF11 variant as described herein). In some embodiments, the composition is a pharmaceutical composition. As used herein, the term "pharmaceutical composition" refers to the active agent in combination with a pharmaceutically acceptable carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some aspects, a composition described herein comprising a GDF11 variant can be used for rejuvenating neural stem cells and/or progenitor cells in a subject in need thereof, wherein increased levels of GDF11 protein in the subject rejuvenate neural stem cells and/or progenitor cells in the subject.

In some embodiments, the composition causes the subject's neural stem cells to increase in frequency or number, thereby rejuvenating the neural stem cells and/or progenitor cells in the subject.

In some aspects, a composition described herein comprising a GDF11 variant can be used for increasing neurogenesis in a subject in need thereof, wherein increased levels of GDF11 protein in the subject increases neurogenesis in the subject. In some embodiments of this and other aspects disclosed herein, increasing neurogenesis is associated with neural cell proliferation, increasing neural cell differentiation, increasing the number of neural stem cells, increasing the number of neural progenitor cells, increasing the number of neural precursor cells, increasing expression of at least one synaptic plasticity gene, at least one neuroprotective gene, or at least one neuronal specification gene selected from the group consisting of neuronal PAS domain protein 4 (Npas4) (NCBI Gene ID: 266743), dual specificity phosphatase 1 (Dusp1) (NCBI Gene ID: 1843), heat shock 70 kDa protein 8 (Hspa8) (NCBI Gene ID: 3312), BTG family, member 2 (Btg2) (NCBI Gene ID: 7832), activity-regulated cytoskeleton-associated protein (Arc) (NCBI Gene ID: 23237), nuclear receptor subfamily 4, group A, member 1 (Nr4a1) (NCBI Gene ID: 3164), cysteine-rich, angiogenic inducer, 61 (Cyr61) (NCBI Gene ID: 3491), FBJ murine osteosarcoma viral oncogene homolog (Fos) (NCBI Gene ID: 2353), jun B proto-oncogene (Junb) (NCBI Gene ID: 3726), Kruppel-like factor 10 (Klf10) (NCBI Gene ID: 7071), nuclear receptor subfamily 4, group A, member 2 (Nr4a2) (NCBI Gene ID: 4929), claudin 1 (Cldn1) (NCBI Gene ID: 9076), early growth response 2 (Egr2) (NCBI Gene ID: 1959), crystalline, mu (Crym) (NCBI Gene ID: 1428), early growth response 1 (Egr1) (NCBI Gene ID: 1958), and polio-like kinase 2 (Plk2) (NCBI Gene ID: 10769), and increasing the number of new neurons.

In some aspects, a composition described herein comprising a GDF11 variant can be used for treating or preventing a neurodegenerative disorder in a subject in need thereof, wherein increased levels of GDF11 protein treat or prevent the neurodegenerative disorder.

In some aspects, a composition described herein comprising a GDF11 variant can be used for treating or preventing a neurodegenerative disorder by increasing neurogenesis in a subject, wherein increased levels of GDF11 protein increase neurogenesis in the subject, thereby treating or preventing the neurodegenerative disorder.

In some embodiments of this and other aspects described herein, the subject has been diagnosed with a neurodegenerative disorder due to aging.

In some aspects, a composition described herein comprising a GDF11 variant can be used for increasing angiogenesis in a subject in need thereof, wherein increased levels of GDF11 protein in the subject increase angiogenesis in the subject. In some embodiments, increasing angiogenesis comprises increasing cerebrovascular architecture, increasing capillary density, increasing cerebral blood flow, and increasing cerebral vessel sprouting branch points.

In some aspects, a composition described herein comprising a GDF11 variant can be used for treating or preventing a neurovascular disorder in a subject in need thereof, wherein increased levels of GDF11 protein in the subject treat or prevent the neurovascular disorder in the subject.

In some aspects, a composition described herein comprising a GDF11 variant can be used for treating or preventing a neurovascular disorder by increasing angiogenesis in a subject, wherein increased levels of GDF11 protein in the subject increase angiogenesis in the subject, thereby treating or preventing the neurovascular disorder in the subject.

Methods and Compositions for Rejuvenating Skeletal Muscle Stem Cells

Described herein are methods comprising administering to a subject an agent or composition which increases the level of GDF11 polypeptide in the subject, wherein the agent or composition comprises a GDF11 variant. In some embodiments, the subject is one who has, or has been diagnosed as having a skeletal muscle condition due to aging. As used herein, a "skeletal muscle condition" due to aging refers to a skeletal muscle condition described herein which is attributable to a subject's age. In some embodiments, the subject is one who is at risk of developing a skeletal muscle condition due to aging. In some embodiments, the subject is an elderly subject. In some embodiments, an elderly subject is over the age of 50, 55, 60, 65, 70, 75, 80, 85, 90, or 100 years.

In some embodiments, the composition which increases the level of GDF11 polypeptide is administered to a subject who has or has been diagnosed with a neuromuscular disease described herein.

In some embodiments, the level of GDF11 polypeptide is the level of GDF11 in the circulation of a subject. In some embodiments, the level of GDF11 polypeptide is the level of GDF11 in the skeletal muscle tissue of a subject. In some embodiments, the level of GDF11 polypeptide is determined by measuring the level of an mRNA encoding a GDF11 polypeptide. The level of GDF11 in a subject can be determined by obtaining a biological sample from the subject and determining the level of GDF11 in the biological sample. Methods for determining the level of a polypeptide in a subject or a sample obtained from a subject are well known in the art and include, but are not limited to, ELISA, radioimmunoassay, immunohistochemistry, methods involving a labeled antibody specific for GDF11, dot blot analysis, functional bioassays, Northern blot, in-situ hybridization, and RT-PCR, aptamer-based proteomic technology (e.g., SOMAscan™ commercially available from Soma-Logic, Inc.) among others. Antibodies specific for GDF11 are commercially available, (e.g. Cat. No. ab71347 from Abcam: Cambridge, Mass.). In some embodiments, the antibodies are antibodies which do not cross-react with GDF8. In some embodiments, the antibodies are selective GDF11 monoclonal antibodies. In some embodiments, the level of GDF11 can be measured as described in Souza et al., Molecular Endocrinology 2008 22:2689-2702; which is incorporated by reference herein in its entirety.

As animals age, skeletal muscle often atrophies and experiences diminished regenerative potential due to deterioration of skeletal muscle stem cells, which is often accompanied by one or more skeletal muscle conditions (e.g., sarcopenia). Without wishing to be bound by theory, it is believed that deterioration of skeletal muscle stem cells and characteristic attendant reduced skeletal muscle mass results in part from decreased levels of circulating GDF11 polypeptide.

Accordingly, in one aspect, the present invention provides a method of rejuvenating skeletal muscle stem cells in a subject in need thereof, comprising administering to the subject a composition which increases the level of GDF11 polypeptide in the subject. In some embodiments, the composition causes the subject's skeletal muscle stem cells to increase in frequency or number, increases the sizes of regenerating myofibers, increases the efficiency of myogenic colony formation, increases the percentage of intact muscle stem cell nuclei, and decreases the percentage of severely damaged deoxyribonucleic acid (DNA), thereby rejuvenating the skeletal muscle stem cells in the subject.

In another aspect, the present invention provides a method of promoting skeletal muscle regeneration in a subject in need thereof, comprising administering to the subject a composition which increases the level of GDF11 polypeptide in the subject, wherein the composition causes the subject's skeletal muscle stem cells to increase in frequency or number, increases the sizes of regenerating myofibers, increases the efficiency of myogenic colony formation, increases the percentage of intact nuclei, and decreases the percentage of severely damaged DNA, thereby promoting skeletal muscle regeneration in the subject.

In some embodiments the level of GDF11 in the subject is increased by at least 20% over the level of GDF11 in the subject prior to treatment, e.g. 20% or more, 30% or more, 40% or more, 50% or more, 100% or more, 150% or more, 200% or more, 250% or more, 300% or more, or 350% or more. In some embodiments the level of GDF11 in the subject is increased by at least 100% over the level of GDF11 in the subject prior to treatment. In some embodiments the level of GDF11 in the subject is increased by at least 200% over the level of GDF11 in the subject prior to treatment. In some embodiments the level of GDF11 in the subject is increased by about 250% over the level of GDF11 in the subject prior to treatment. In some embodiments, the level of GDF11 in the subject is increased to at least 50% of a healthy reference level, e.g. 50% or more, 60% or more, 70% or more, 80% or more, 90% or more, or 100% or more of a healthy reference level. In some embodiments, the level of GDF11 in the subject is increased to at least 60% of a healthy reference level. In some embodiments, the level of GDF11 in the subject is increased to at least 75% of a healthy reference level. In some embodiments, the level of GDF11 in the subject is increased to at least 90% of a healthy reference level. A healthy reference level can be the average level of GDF11 in a population of human subjects (e.g., young individuals) not exhibiting any signs or symptoms of skeletal muscle stem cell deterioration, or related conditions.

As used herein, "skeletal muscle stem cell deterioration" refers to a decrease in cell number, a decrease in regenerating myofiber size, a decrease in the efficiency of myogenic colony formation, a decrease in the percentage of intact nucleic, and an increase in the percentage of severely damaged DNA as assessed by a Comet assay, in skeletal muscle stem cells.

In some embodiments, a healthy reference level can be the average level of GDF11 in a population of human subjects not exhibiting any signs or symptoms of skeletal muscle stem cell deterioration, or related conditions and who are under the age of 70. In some embodiments, a healthy reference level can be the average level of GDF11 in a population of human subjects not exhibiting any signs or symptoms of skeletal muscle stem cell deterioration, or related conditions and who are under the age of 65. In some embodiments, a healthy reference level can be the average level of GDF11 in a population of human subjects not exhibiting any signs or symptoms of skeletal muscle stem cell deterioration, or related conditions and who are under the age of 60. In some embodiments, a healthy reference level can be the average level of GDF11 in a population of human subjects not exhibiting any signs or symptoms of skeletal muscle stem cell deterioration, or related conditions and who are under the age of 55. In some embodiments, a healthy reference level can be the average level of GDF11 in a population of human subjects not exhibiting any signs or symptoms of skeletal muscle stem cell deterioration, or related conditions and who are under the age of 50. In some embodiments, a healthy reference level can be the average level of GDF11 in a population of human subjects not exhibiting any signs or symptoms of skeletal muscle stem cell deterioration, or related conditions and who are under the age of 45. In some embodiments, a healthy reference level can be the average level of GDF11 in a population of human subjects not exhibiting any signs or symptoms of skeletal muscle stem cell deterioration, or related conditions and who are under the age of 40. In some embodiments, a healthy reference level can be the average level of GDF11 in a population of human subjects not exhibiting any signs or symptoms of skeletal muscle stem cell deterioration, or related conditions and who are under the age of 35. In some embodiments, a healthy reference level can be the average level of GDF11 in a population of human subjects not exhibiting any signs or symptoms of skeletal muscle stem cell deterioration, or related conditions and who are under the age of 30. In some embodiments, a healthy reference level can be the average level of GDF11 in a population of human subjects not exhibiting any signs or symptoms of skeletal muscle stem cell deterioration, or related conditions and who are under the age of 25. In some embodiments, a healthy reference level can be the average level of GDF11 in a population of human subjects not exhibiting any signs or symptoms of skeletal muscle stem cell deterioration, or related conditions and who are under the age of 20.

In some embodiments, the methods described herein can comprise selecting a subject with a level of GDF11 which is lower than a healthy reference level and administering a treatment as described herein.

In some embodiments, the level of GDF11 in a subject is increased in order to treat a skeletal muscle condition (e.g. sarcopenia or a sarcopenia associated condition or symptom as described herein). In some embodiments, the level of GDF11 in a subject is increased in order to prevent a skeletal muscle condition (e.g., sarcopenia or a sarcopenia associated condition or symptom as described herein).

Skeletal muscle conditions related to low or decreased GDF11 polypeptide tend to develop with the decrease in GDF11 levels that occur with increasing age. Thus, it is expected that such conditions can be prevented or, at a minimum, delayed, by maintaining GDF11 polypeptide levels at or near the level found in normal, healthy young adults (e.g., by administering a GDF11 polypeptide or a nucleic acid encoding a GDF11 polypeptide with advancing age, but prior to the onset of a skeletal muscle condition).

In another aspect, the present invention provides a method of treating or preventing a skeletal muscle condition in a subject in need thereof, comprising administering to the subject an effective amount of a composition which increases the level of GDF11 polypeptide in the subject, wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing the skeletal muscle condition. In some embodiments, the skeletal muscle condition is selected from the group consisting of atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness.

Class I sarcopenia has been defined as an appendicular lean body mass index (ALBMI) <or=6.44 kg·m(−2) (appendicular lean body mass/height) (Messier V, Karelis A D, Lavoie M E, Brochu M, Faraj M, Strychar I, Rabasa-Lhoret R. Metabolic profile and quality of life in class I sarcopenic overweight and obese postmenopausal women: a MONET study. Appl Physiol Nutr Metab. 2009 February; 34(1): 18-24.) This definition requires scanning of the legs and/or arms to determine muscle bulk. It has also been argued that these scans may not be necessary and that sarcopenia can be defined by measuring anthropometric measurements like arm muscle circumference and calf circumference to determine a below normal amount of limb skeletal muscle (Bauer J M, Kaiser M J, Sieber C C. Sarcopenia in nursing home residents. J Am Med Dir Assoc. 2008 October; 9(8):545-51). A working definition has been given which identifies sarcopenia when skeletal muscle mass in an older subject is more than 2 standard deviations below the mean for healthy younger adults (Baumgartner R N, Koehler K M, Gallagher D, et al (April 1998). "Epidemiology of sarcopenia among the elderly in New Mexico". Am. J. Epidemiol. 147 (8): 755-63).

The compositions and methods described herein are useful for treating or preventing sarcopenia or a condition or symptom associated with sarcopenia (e.g., loss of skeletal muscle mass associated with sarcopenia; fatigue associated with sarcopenia; disability associated with sarcopenia; morbidity associated with sarcopenia; muscle weakness associated with sarcopenia) or to increase the strength of skeletal muscle in sarcopenia or to reduce the risk of bony fractures in a patient with sarcopenia; or for the prevention or treatment of muscle wasting associated with aging; muscle weakness associated with muscle wasting associated with aging; disuse atrophy; muscle weakness associated with disuse atrophy; or for the prevention or secondary prevention of bony fractures associated with muscle wasting or weakness associated with aging or sarcopenia.

Accordingly, in still another aspect, the present invention provides a method of treating or preventing sarcopenia in a subject in need thereof, comprising administering to the subject an effective amount of a composition which increases the level of GDF11 polypeptide in the subject, wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing sarcopenia in the subject.

Aspects of the technology described herein relate to compositions comprising a GDF11 variant as described herein. In some embodiments, the composition is a pharmaceutical composition. As used herein, the term "pharmaceutical composition" refers to the active agent in combination with a pharmaceutically acceptable carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some aspects, a composition described herein comprising a GDF11 variant can be used for rejuvenating skeletal muscle stem cells in a subject in need thereof, wherein increased levels of GDF11 protein in the subject rejuvenate skeletal muscle stem cells in the subject. In some embodiments, the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby rejuvenating the skeletal muscle stem cells in the subject.

In some aspects, a composition described herein comprising a GDF11 variant can be used for promoting skeletal muscle regeneration in a subject in need thereof, wherein increased levels of GDF11 protein in the subject cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby promoting skeletal muscle regeneration in the subject.

In some aspects, a composition described herein comprising a GDF11 variant can be used for treating or preventing a skeletal muscle condition in a subject in need thereof, wherein increased levels of GDF11 protein cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing the skeletal muscle condition in the subject. In some embodiments, the skeletal muscle condition is selected from the group consisting of atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness.

In some aspects, a composition comprising a GDF11 variant can be used for treating or preventing sarcopenia in a subject in need thereof, wherein increased levels of GDF11 protein cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing sarcopenia in the subject.

In some embodiments of this and other aspects described herein, the subject has been diagnosed with a skeletal muscle condition due to aging.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or prior publication, or for any other reason. All statements as to the date or representation as to the contents of these documents is based on the information available to the applicants and does not constitute any admission as to the correctness of the dates or contents of these documents.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Declining muscle function and loss of muscle regenerative potential are nearly universal characteristics of aging in humans (1) and strong predictors of human mortality in both older (2) and middle aged (3) adults. Degenerative changes in aging muscle impede normal activities, leading to loss of independence and secondary impacts on bone and metabolic function that further reduce overall health. Indeed, it has been estimated that ~$18.5 billion in U.S. healthcare expenditures in the year 2000 were attributable to age-related muscle wasting (sarcopenia) (4), and since then, the number of elderly Americans has increased by nearly 50% (with an expected doubling by the year 2030 (5)). Thus, it is extremely likely that, without new therapeutic opportunities, the already substantial burden that muscle dysfunction places on the health care system will very soon exceed available resources. Adding further urgency to the need for new muscle-targeted treatments, there are currently no approved pharmacological interventions that can slow, much less reverse, the inexorable deterioration of skeletal muscle that occurs with advancing age. Thus far, the only widely-accepted intervention that has shown impact in reducing sarcopenia and preserving muscle repair potential in aging humans is exercise (6-8); however, the mechanisms underlying exercise effects remain obscure, and problems with access, compliance and substantial individual-to-individual variability of response limit the therapeutic potential of this lifestyle intervention.

Motivated by the significance and urgency of muscle-related health concerns in our aging population, it is necessary to identify muscle cell intrinsic, local and systemic regulators that can be targeted to improve muscle health in older individuals. While various studies have identified multiple important pathways within each of these regulatory nodes as important, from a therapeutics perspective, the effects of blood-circulating factors are perhaps most captivating, given the ease with which such factors can be measured and introduced into the bloodstream in live, alert humans, and the capacity of systemically supplied agents to access each and every cell within the muscle tissue despite its large size (30-40% of total body mass) and broad distribution throughout the body. Moreover, heterochronic parabiosis and blood transfusion studies (9-13), clearly indicate that much of the deterioration of cell function that normally accompanies aging can be slowed or even reversed through mechanisms controlled by blood-borne factors (reviewed in (14)).

Molecular identification of these regulators has been a focus of intense research, and recent papers suggest that the small circulating protein GDF11 is likely to be a critical contributor (9-11, 15). In particular, it has been reported that GDF11 expression declines with age in mice (9, 16) and that supplementing levels of native GDF11 protein systemically can reverse age-related deficits in multiple major organ systems, including the heart, skeletal muscle and brain. Indeed, these effects of GDF11 recapitulate many of the effects seen with heterochronic parabiosis. Importantly, independent studies in fly, rodent and human systems have corroborated the notion that higher levels of GDF11 are associated with delayed onset of neuromuscular decline (17), extended lifespan among 16 mammalian species (18) and 22 inbred mouse strains (19), increased muscle performance in physically active older men (20), and protection from declining muscle strength in rGDF11-supplemented aged rats (see FIG. 1).

Figure 2:
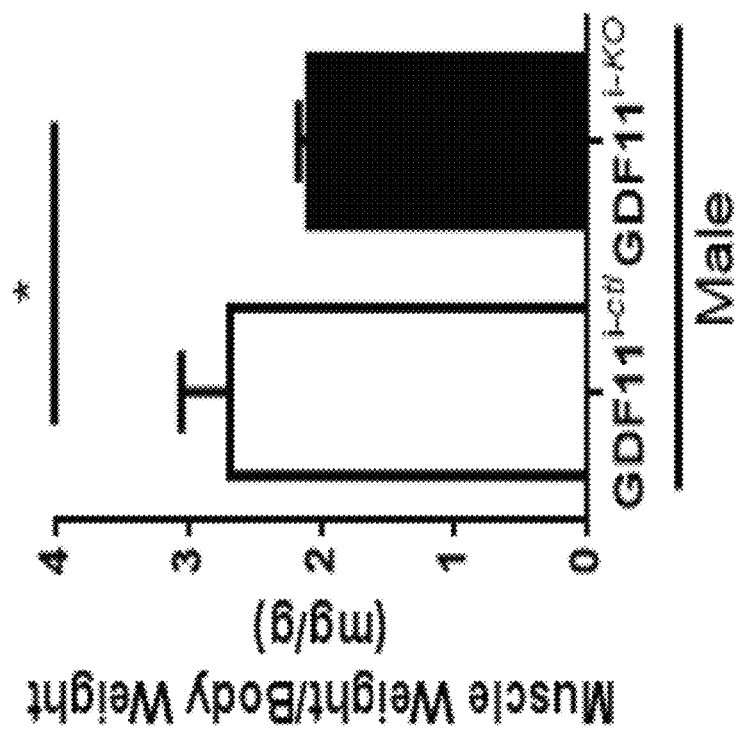
FIG. 2 shows loss of GDF11 impairs skeletal muscle maintenance. TA and EDL skeletal muscle weight are collected and normalized to body weight 15 days after tamoxifen (tam) injection to induce deletion of GDF11 (GDF11$^{i-KO}$ mice). Analysis showed that skeletal muscle mass is significantly reduced in GDF11$^{i-KO}$ mice, compared to tam-injected controls with intact GDF11 (GDF11$^{i-ctl}$ mice).
Figure 3:
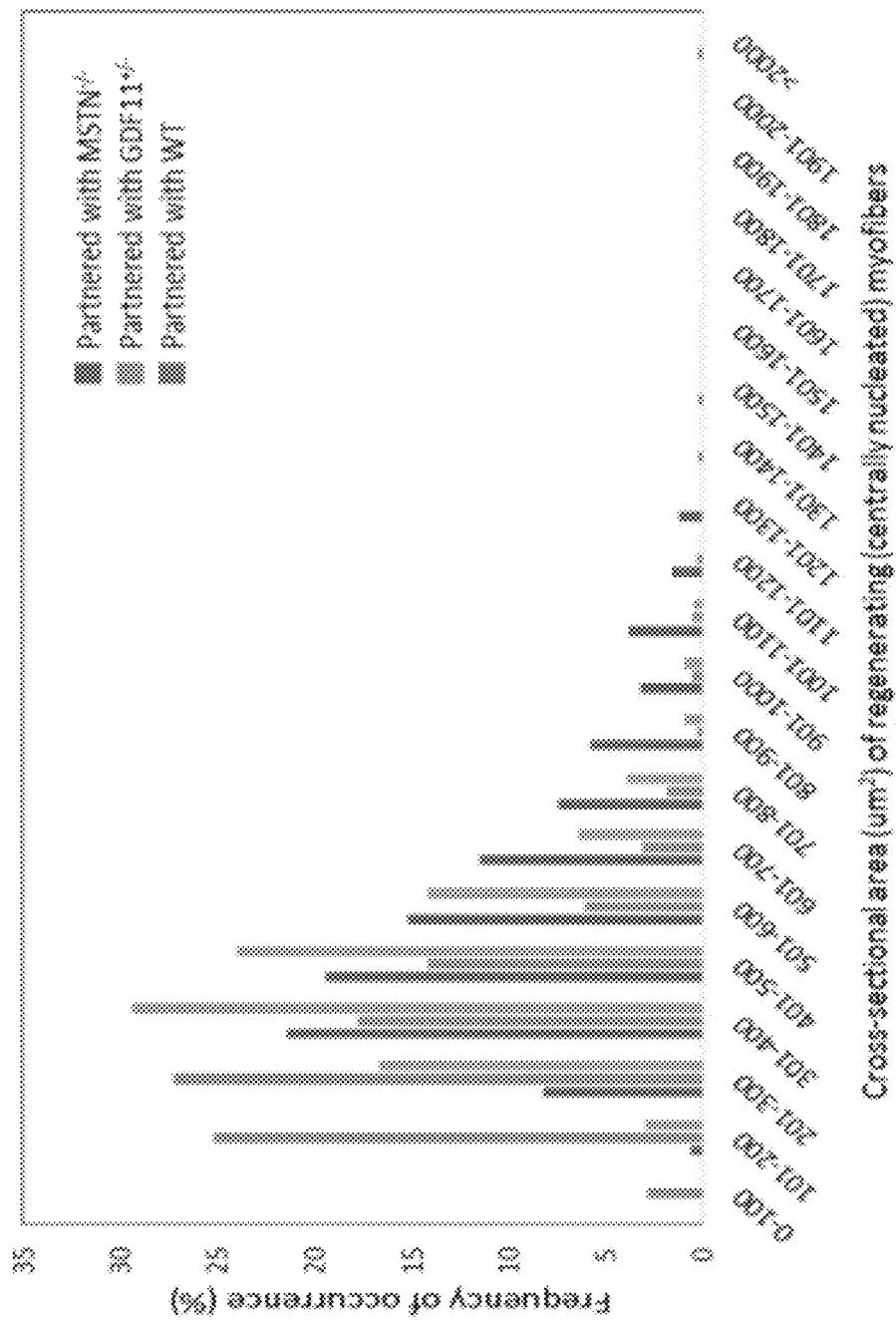
FIG. 3 shows effects of circulating GDF11 and MSTN on muscle repair in aged mice. Young MSTN KO, GDF11$^{+/-}$ (HET), or WT mice (8 weeks old) were joined in heterochronic parabiosis to aged WT mice (21 months old) (n=3-4 pairs per group). After 8 days, the outer hindlimbs of the aged WT partners were cryoinjured. 7 days after injury, muscles were analyzed to determine the size of regenerating (centrally nucleated, CN) fibers. Aged WT mice joined to GDF11 HET partners showed decreased CSA and those joined to MSTN KO partners had increased fiber CSA as compared to WT (p<0.05).

Finally, preliminary data recently generated indicates that induced loss of GDF11, by tamoxifen injection in adult male RosaCreER; GDF11fl/fl mice, leads to reduced muscle mass (FIG. 2) and that a reduction in systemic GDF11 in young mice joined to aged partners in heterochronic parabiosis impedes their ability to promote muscle repair in aged partners (FIG. 3). These data are consistent with the notion that GDF11 functions as an anti-geronic regulator of skeletal muscle aging and suggest that strategies to increase GDF11 levels may hold promise for preventing or reversing age-related loss of muscle mass and disruption of muscle regenerative potential.

A novel (non-native or non-wildtype) variant of GDF11 ("GDF11var") was generated. The GDF11var allele modifies the coding sequence of the native protein by inclusion of 2 additional amino acids (tryptophan and glutamic acid) at the ligand's C-terminus. While studies to date have predicted that modification of either the N- or C-terminus of GDF11's mature ligand domain would be incompatible with preservation of protein function, the novel modification surprisingly preserves protein function, as demonstrated by the fact that animals homozygous for a knockin of the GDF11var allele at the endogenous GDF11 locus are born alive and do not exhibit any obvious developmental defects (in contrast to the perinatal lethality characteristic of GDF11 loss-of-function alleles (23)).

Figure 4:
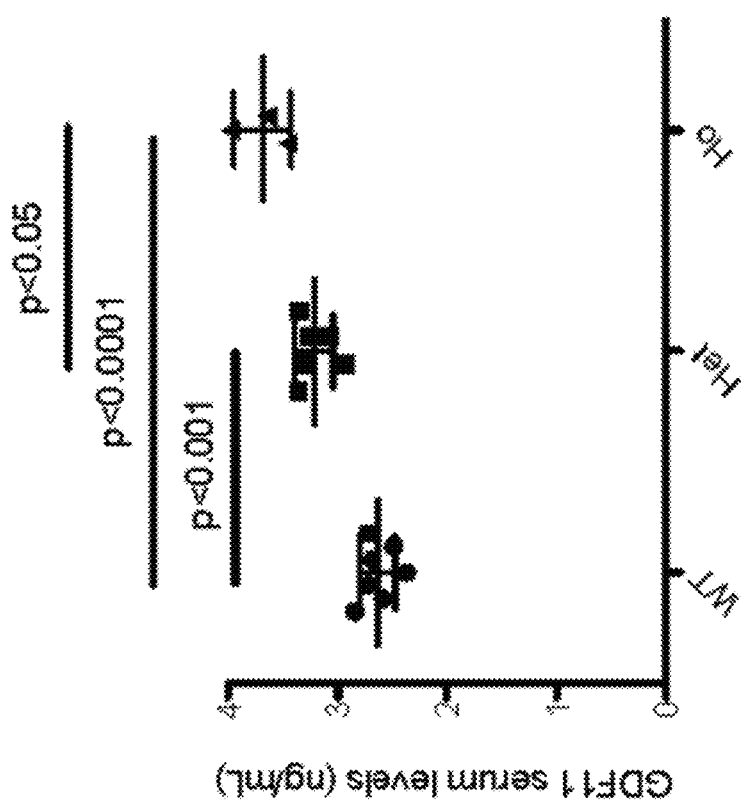
FIG. 4 shows GDF11var mice (carrying 2 GDF11var alleles in the endogenous GDF11 locus) have increased levels of circulating GDF11 protein. Sera collected from young WT mice (2 months of age, males and females combined) or age-matched GDF11var mice heterozygous (HET) or homozygous (HO) for the GDF11var allele was analyzed by LC-MS/MS. P values calculated by one-way ANOVA with Bonferonni post-test.
Figure 5A:
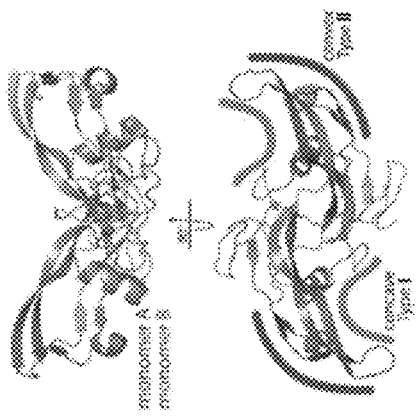
FIGS. 5A-5D shows an overview of GDF11/myostatin structure and signaling.
Figure 5B:
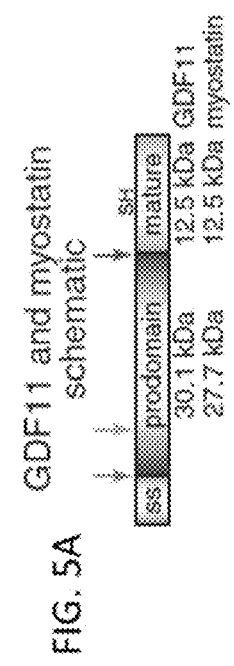
Figure 5C:
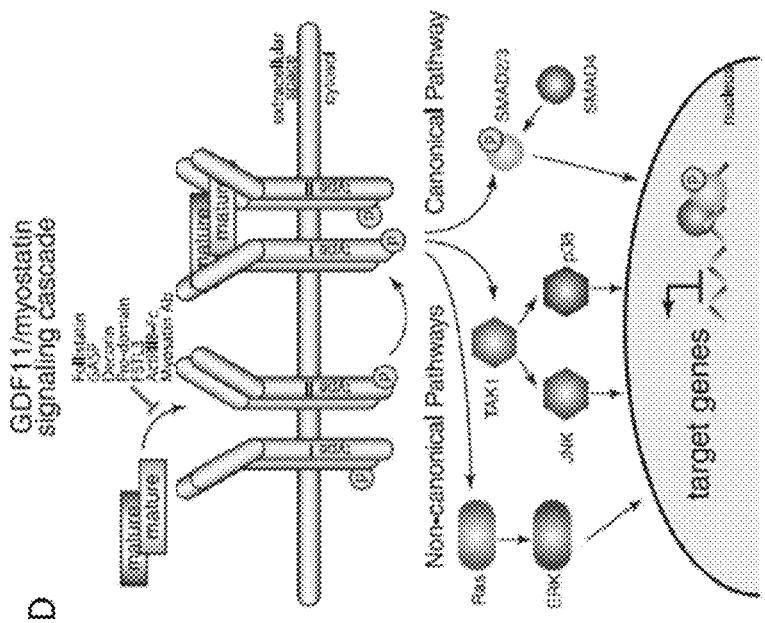
Figure 5D:
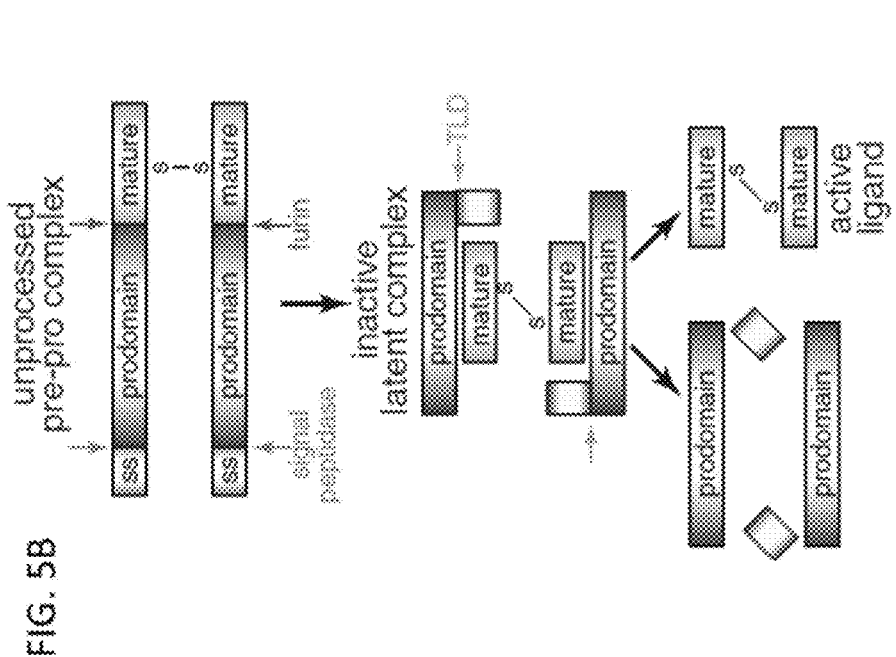

Interestingly, preliminary studies indicate that GDF11var knockin mice also show increased levels of circulating GDF11 protein (FIG. 4), suggesting that this C-terminal modification may increase GDF11 protein stability. Thus, as a potentially more stable, non-native functional form of GDF11, the GDF11var protein presents important advantages over native GDF11.

Additional experiments will be performed to establish additional biological properties of the GDF11 variant, particularly with respect to its effect on baseline physiological parameters and muscle regenerative function. The proposed studies will be performed in young (aged 2-4 months) and aging (6-8 and 12-14 months) mice (n=5-8 male and 5-8 female animals per age group), with comparison to age- and sex-matched wild-type controls (carrying wild-type GDF11 alleles). Systemic protein concentrations will be evaluated using LC-MS/MS (FIG. 4) and ELISA, muscle mass assessed by weighing (FIG. 2) and ultrastructure by electron microscopy, muscle regenerative potential will be determined histologically after cryoinjury or cardiotoxin injection (FIG. 3), neuromuscular junction integrity and NMJ size will be measured by immunofluorescence analysis, and muscle function will be evaluated by grip strength (FIG. 1) and exercise endurance testing. These analyses will provide baseline parameters for muscle mass and function in the presence of elevated levels of GDF11, specifically GDF11var, and clarify the potential for this variant protein to be used therapeutically.

The various experiments will result in obtaining baseline data on levels in sera of GDF11, GDF8 and various GDF11/8 antagonists in young and aging homozygous and heterozygous GDF11var mice. (1-2 months); obtaining baseline data on body, muscle and heart weight in young and aging GDF11var mice (1-2 months); analyzing muscle structure, NMJ integrity and muscle function in young and aging GDF11var mice (3-4 months); evaluating muscle regeneration potential in young and aging GDF11var mice (2-3 months); assessing the capacity of homozygous GDF11var animals to rescue muscle phenotypes in aged wild-type mice when joined in heterochronic parabiosis (4 mo.); and comparing the half-life and activity of GDF11var to native GDF11 protein using plasma transfusion studies and SMAD reporter assays. (2 mo.)

Example 2

The Transforming Growth Factor-Beta (TGF-β) superfamily, a group of secreted proteins that bind to cell surface receptors and induce intracellular signaling cascades, are important in both embryonic development and mature animal tissue homeostasis. The importance of the group is highlighted by its deep conservation across animals, being found in both vertebrates and invertebrates (Nakashima, Toyono, Akamine, & Joyner, 1999; Rochette, Zeller, Cottin, & Vergely, 2015). The search for undiscovered members of the TGF-β superfamily at the turn of the century uncovered two new molecules in the activin family Growth Differentiation Factor 8 (GDF8), also known as myostatin, and Growth Differentiation Factor 11 (GDF11) (McPherron, Lawler, & Lee, 1997; A. C. McPherron, A. M. Lawler, & S.-J. Lee, 1999; Nakashima et al., 1999). With a burst of recent research on GDF11 revealing surprising and contradictory insights into the molecule, further inquiry into the exact nature of GDF11 remains a pertinent topic in the fields of aging research and developmental biology.

The structure and pathway by which GDF8 and GDF11 functions have been well studied: both are first translated into a pre-processed complex that has an N-terminal prodomain attached to a C-terminal mature signaling portion of the protein (Walker et al., 2016). Following cleavage by furin-like proteases, the prodomain remains non-covalently bound to the mature protein, holding it in a latent state and preventing binding to receptors (Walker et al., 2016). For the protein to become active, an additional cleavage event must occur, mediated by a tolloid-like metalloproteinase (Walker et al., 2016). The function of GDF11 is further regulated by the presence of numerous extracellular binding proteins, including GASP1, GASP2, decorin, follistatin, and follistatin-like 3 (FSTL3), which act as antagonists to GDF11, binding the molecule and inhibiting its function (Walker et al., 2016). The various activity states of GDF11 have complicated experiments that attempt to quantify GDF11 levels in different tissues, as the abundance of the molecule may not directly correlate with its level of activity. Thus, further work needs to be done to create accurate assays that differentiate active and latent GDF11.

Like other members of the activin family, GDF11 binds to specific serine/threonine kinase type I and type II receptor complexes, which have a considerable amount of diversity (Rochette et al., 2015). GDF11 has been shown to bind to the type I receptors, ALK4, ALK5, and ALK7 and the activin receptor kinase II-A and II-B, which then go on to activate an intracellular signaling cascade (Walker et al. 2016). Canonically, this kinase activation leads to SMAD2/3 phosphorylation in the cell cytoplasm and the regulation of downstream gene expression. However, a well-defined pathway does not mean that the downstream effects of GDF11 are well known. The cellular response to SMAD activation is complex and dependent on context, such as the presence of transcription factors and chromatin modifiers (Walker et al., 2016). Additionally, members of the TGF-β family function through both Smad-dependent and Smad-independent pathways and GDF11 affects numerous non-canonical pathways, including ERK, JNK, and p38 MAPK (Derynck & Zhang, 2003; Walker et al., 2016). The numerous transcriptional effectors downstream of GDF11 highlight the need for research that characterizes the transcriptional profile GDF11 induces in a variety of tissues.

A confounding factor in detecting GDF11 in adult animals is the similarity between the mature myostatin and GDF11 proteins. GDF11 and myostatin share nearly 90% of their sequence identity within their C-terminal mature domains and nearly 52% sequence identity in their cleaved prodomains (Walker et al., 2016). Recent research has shown that, despite this extensive sequence overlap, GDF11 and GDF8 have distinct differences in both potency and structure. In a HEK293 pSMAD luciferase reporter assay, treating cells with rGDF11 resulted in a certain level of signal that was not detected when the same cells were treated with similar levels of rGDF8, perhaps indicating differences in potency between the two ligands (Walker et al., 2017). Additionally, GDF11 was found to be more effective in signaling through the type I receptors commonly associated with the TGF-β family, such as ALK4 and ALK5, generating more reporter activity across all receptors tested (Walker et al., 2017). These findings support the notion that despite the homology between GDF8 and GDF11, the slight amino acid divergence could drive profound and fundamental differences in the function of these molecules. Due to the conserved nature of GDF8 and GDF11's protein sequence and structure, reflecting on the differences between the two molecules is important in shifting notions that similar structure and sequence implies similar function.

While the role of Mstn in negatively regulating skeletal muscle has been clearly demonstrated in knockout mice, with homozygous Mstn knockout mutants that were 30% larger than wild-type controls due to an increase in muscle mass, the role of GDF11 is more complex (McPherron et al., 1997). Early in situ hybridization experiments revealed widespread expression of Gdf11 during mouse embryogenesis, with expression in the developing tail bud, the mesenchyme between skeletal elements, early tooth structures, digit tips, and the developing brain (Nakashima et al., 1999). Additional experiments on a frog model, Xenopus laevis, with an animal cap assay that takes ectoderm from the developing frog blastula and introduces protein, showed that GDF11 induced conversion of ectoderm tissue into mesoderm and, in high concentrations, neural tissue (Gamer et al., 1999). Additionally, full-body GDF11 knockout mice show perinatal lethality, kidney agenesis, spleen deformation, retinal development alterations, and pancreas deformation (Harmon et al., 2004; A. C. McPherron, A. M. Lawler, & S. J. Lee, 1999; Santos et al., 2012). The deletion of one GDF11 allele in mice results in mild skeletal abnormalities, while homozygous null animals exhibit anteriorly directed homeotic transformations with 4-5 ectopic ribs and truncated tails, showing the importance of GDF11 in regulating body patterning (McPherron et al., 1999). These early experiments introduced GDF11 as an important regulatory agent responsible for body patterning and tissue differentiation upstream of Hox genes. Clearly important to the developing embryo, the function of GDF11 in adult tissue homoeostasis has been more difficult to determine due to the perinatal lethality of the full-body GDF11 knockout mice.

One important area in which GDF11 has been heavily implicated is physiological aging. Heterochronic parabiosis experiments, which join the circulatory systems of old and young mice together, showed that exposure to a youthful systemic environment reversed many markers of aging in a variety of tissues in mice (Conboy et al., 2005). These experiments demonstrated 'young blood' could restore muscle satellite cell genomic integrity, improve injury-induced muscle regenerative potential, induce the remodeling of aged cerebral vasculature, and reduce age-related cardiac hypertrophy (Katsimpardi et al., 2014; Loffredo et al., 2013; Sinha et al., 2014). The beneficial effect of 'young blood' was further supported by additional experiments that described human umbilical cord plasma as revitalizing hippocampal function, reversing age-related cognitive decline (Castellano et al., 2017). Not associated with the change in behavior and blood pressure that comes along with the parabiosis method, these results were attributed to systemic factors present in the young mouse blood and serum (Loffredo et al., 2013). Through an aptamer-based metabolomic, lipidomic, and a proteomic screen, GDF11 was identified as showing differential abundance in the blood plasma of unpaired young and aged mice (Loffredo et al., 2013). Both in vitro and in vivo assays that introduced recombinant GDF11 through an intraperitoneal injection to an aged environment led to results that mirrored the rescue of phenotypes seen with the heterochronic mouse experiments (Katsimpardi et al., 2014; Loffredo et al., 2013; Sinha et al., 2014). Specific examples include a significant decrease in the heart weight-to-tibia length ratio in old mice injected with recombinant GDF11, signifying a reduction in cardiac hypertrophy, and a 50% increase in the volume of cerebral blood vessels, indicating positive remodeling of the cerebral vasculature (Katsimpardi et al., 2014; Loffredo et al., 2013). These experiments portray a decrease in GDF11 as an integral component to systemic aging in mice, with addition of the molecule reversing multiple aging-related phenotypes across organ systems.

However, the intricacies of GDF11 pose a challenge to any researcher looking to make definite causal statements and conflicting studies have associated GDF11 as driving age-related dysfunction. Additional screens of extracellular proteins on aged muscle skeletal satellite cells did not identify GDF11 as a potential factor that reverses age-related dysfunction and the in vivo addition of recombinant GDF11 decreased young satellite cell numbers (Egerman et al., 2015; Hinken et al., 2016). Claims have also been made that the reagents used to measure GDF11 in the research done by Loffredo et al., Sinha et al., and Katsimpardi et al. were not specific and also detected myostatin (Egerman et al., 2015). This means that while Loffredo et al. confirmed that the overall pool of GDF8 and GDF11 increased with age, conclusions about GDF11-specific levels could not be made (Egerman et al., 2015). Furthermore, high levels of exogenous GDF11 has also been reported to induce skeletal and cardiac muscle wasting (Hammers et al., 2017; Jones et al., 2018). Conflictingly, the addition of recombinant GDF11 into murine cardiac tissue found no change in cardiac function or size (Smith et al., 2015). One experiment conducted by Zimmers et al. showed the continuous, elevated presence of GDF11 levels, achieved through the introduction of Chinese hamster ovary (CHO) cell lines that produced GDF11 being injected into muscle, showed supraphysiological GDF11 levels as driving a decrease in skeletal muscle mass, reducing cardiac size and function, and decreasing overall body weight (Zimmers et al., 2017). These contradictory experiments indicate that more work needs to be done to develop systematic and accurate ways to assay GDF11 function and levels in adult animals.

Further studies support other characterizations of circulating GDF11 levels in aging Immunoplexed liquid chromatography mass spectromic assessment of GDF11 and myostatin, a highly specific assay that uses unique amino acid sequence features of both molecules, concluded that circulating GDF11 levels do not change with age (Schafer et al., 2016). However, following a cohort of individual humans post-aortic valve replacement surgery revealed that those who reported having at least a subset of the clinical measurements of frailty—weak grip strength, low endurance, slow gait, and slow activity levels—had higher circulating GDF11 levels (Schafer et al., 2016). Because GDF11 has many forms—free, latent, and complexed with extracellular antagonists, such as GASP-1 or GASP-2—any causal statements linking overall GDF11 levels to a phenotype must be qualified (Harper et al., 2016). Despite not finding trends in GDF11 levels throughout human lifespan, Schafer et al. did associate the molecule with negative post-operative outcomes. This finding contrasts past research that proposed GDF11 as a novel predictor of mammalian life span (Zhou et al., 2016). Zhou et al. found that mice with higher GDF11 levels at middle age time points, as quantified through a purported GDF11-specific ELISA kit, were more likely to have longer lifespans, possibly indicating some protective effect (Zhou et al., 2016). Despite controversy, it is clear that GDF11 remains important in tissue homeostasis, with either too much or too little protein driving complex physiological changes. GDF11 could be a promising therapeutic target and biomarker of disease risk, and so better characterization of the molecule in aging, and in tissues across the body, remains a very important topic.

Aside from potential implications within the aging field, understanding the function of GDF11 remains important in many other contexts. Research has shown that GDF11 plays an important role in erythropoiesis, inhibiting erythropoiesis in mouse models of beta thalassemia (Dussiot et al., 2014; Suragani et al., 2014). Additionally, GDF11 could also play a role in cancer biology. An examination of colorectal cancer patients found that tumors that expressed high levels of GDF11 were more likely to metastasize, leading to poor rates of patient survival (Zhang et al., 2017). Conflictingly, there has also been research that suggests GDF11 as having a tumor suppressive function in triple negative breast cancer, with the molecule promoting an anti-invasive, epithelial form (Bajikar et al., 2017). Overall, GDF11 is fundamentally important across a wide range of systems and better understanding the exact nature of this molecule gives valuable insights into disease and development.

Figure 6:
FIG. 6 provides an overview of GDF11 indel lines. The Wild-Type GDF11 and the 4 sequenced deletions, excluding Indel 13 that was sequenced separately, and their predicted protein product are schematically displayed. (Gels displaying respective deletion sizes in respect to WT can be seen in FIG. 16).

Although full knockout mice have been available since the turn of the century, recent advances in CRISPR-Cas9 technology have allowed for the emergence of transgenic mice that contain specific deletions or insertions of genetic constructs. CRISPR recognizes sequences based on the introduction of a guide RNA strand and causes a double strand break that is then repaired, either through non-homologous end joining (NHEJ) or homologous recombination (HR)(Doudna & Charpentier, 2014). During the repair, if the genetic construct is not integrated properly into the genome an insertion or deletion frequently referred to as an "indel" mutation occurs (Doudna & Charpentier, 2014). Recently, multiple strains of GDF11 Indel mice were created as a byproduct of inserting an IRES-GFP reporter into the GDF11 locus after the stop codon to better understand the regulatory mechanisms of the molecule. Some cells that underwent the more error-prone mechanism of NHEJ to repair the break, as opposed to HDR with the template strand, led to multiple viable mice that have a deletion in the 3rd exon and the 3'-UTR of GDF11. These mice present a unique opportunity to characterize a novel mutation in the GDF11 gene and its phenotypic effects. Overall, five distinct deletions were created from our four founder animals, existing in various genotypes across the mouse lines. One founder produced two unique deletions—4A and 4B—exemplifying how CRISPR-CAs9 can give rise to unique deletions across different germ cells. Four of the Indel lines were previously sequenced and the predicted protein sequence determined (FIG. 6). The remaining Indel, Line 13, was identified and characterized as part of this project (FIG. 7). The full characterization of these unique deletions could provide further insight into the function of GDF11.

If these mice are viable and present a perturbation of GDF11, these animals could reveal novel information about the functional importance of GDF11 across multiple organ systems. However, if the mice exhibit a wild type, or knockout phenotype, information about the importance of the end of the 3rd exon and the 3'-UTR of GDF11 can also be obtained. A change in GDF11 function could arise from two places—the change in protein structure due to the frame shift nature of the mutation, as well as a possible deletion of regulatory sequences in the 3'-UTR, which could contain MicroRNA Response Elements or other regulatory regions that could prevent proper protein expression.

Results

Figure 7A:
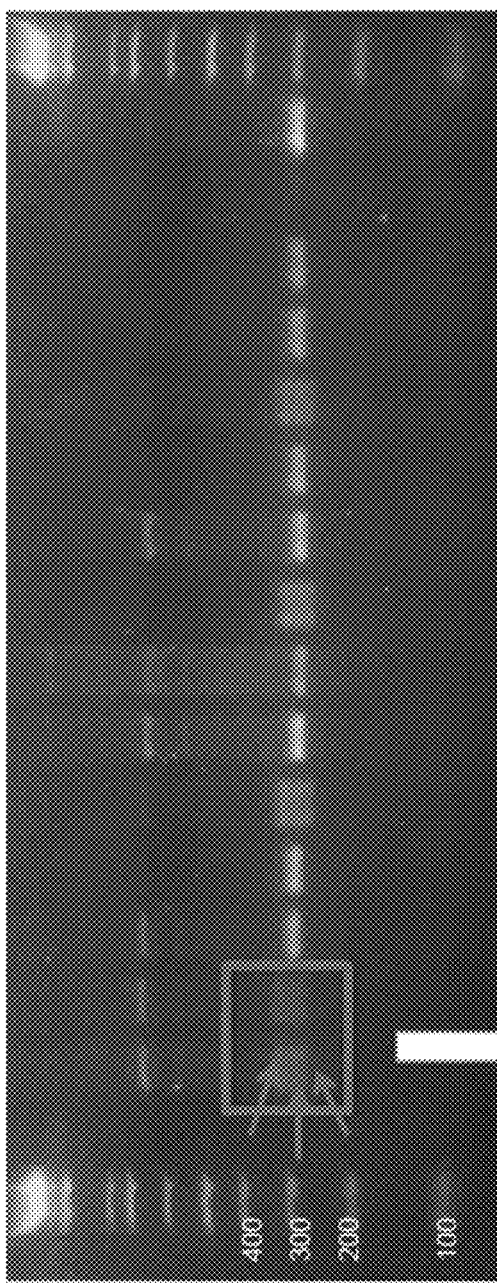
FIGS. 7A-7B demonstrate identification of the indel 13 indel mutation.

Novel mutations to the GDF11 Indel protein were identified and characterized. First, the remaining Indel 13 mutation was identified through DNA sequencing. Although done separately from the other lines, the process of genotyping, purifying DNA from the gel, TOPO® cloning, checking for proper vector incorporation with Colony PCR, and sequencing was the same for all the lines (see Materials and Methods). An overview of this process enables a complete picture of the experimental process for the analysis of the Indel lines—from identification to characterization (FIG. 7A). The Indel 13 mutation was found to be an 18 bp deletion at the end of the 3'UTR, the smallest deletion among the lines. The predicted protein sequence added 22 additional amino acids, placing it between the 4B and 11 deletions in terms of new protein size.

Figure 8A:
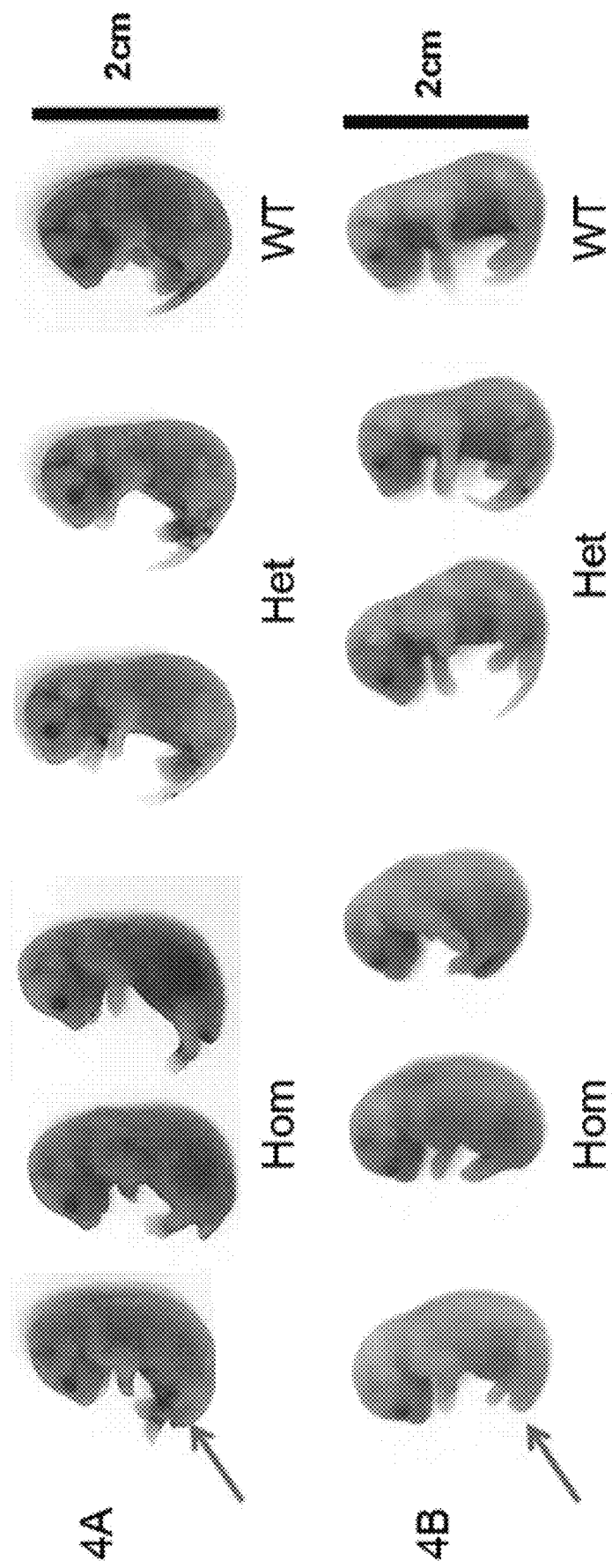
FIGS. 8A-8D demonstrate skeletal analysis of the GDF11 Indel 4A/4B lines.

Following identification, the GDF11 Indel Lines were systematically characterized to check the physiological effect of the different mutant alleles. Breeding pairs between previously genotyped heterozygote animals from the 4A, 4B, and 7 lines were set up to see if viable homozygote animals could be generated. Based on the large deletion present in the 4A and 4B lines, and the ensuing frame-shift mutation that causes an extensive addition of amino acids to the carboxy terminal domain of the protein, it was hypothesized that the animals would phenocopy the GDF11 Knockout phenotype, exhibiting skeletal defects such as anteriorly directed homeotic transformations. To compare the embryos to similar time points as in published full body GDF11 knockout studies, and to avoid the loss of 4A and 4B pups to cannibalism, timed dissections at approximately E18.5 and E17.5, for the 4A and 4B lines respectively, were performed. The embryos were photographed directly after dissection (FIG. 8A).

Figure 8B:
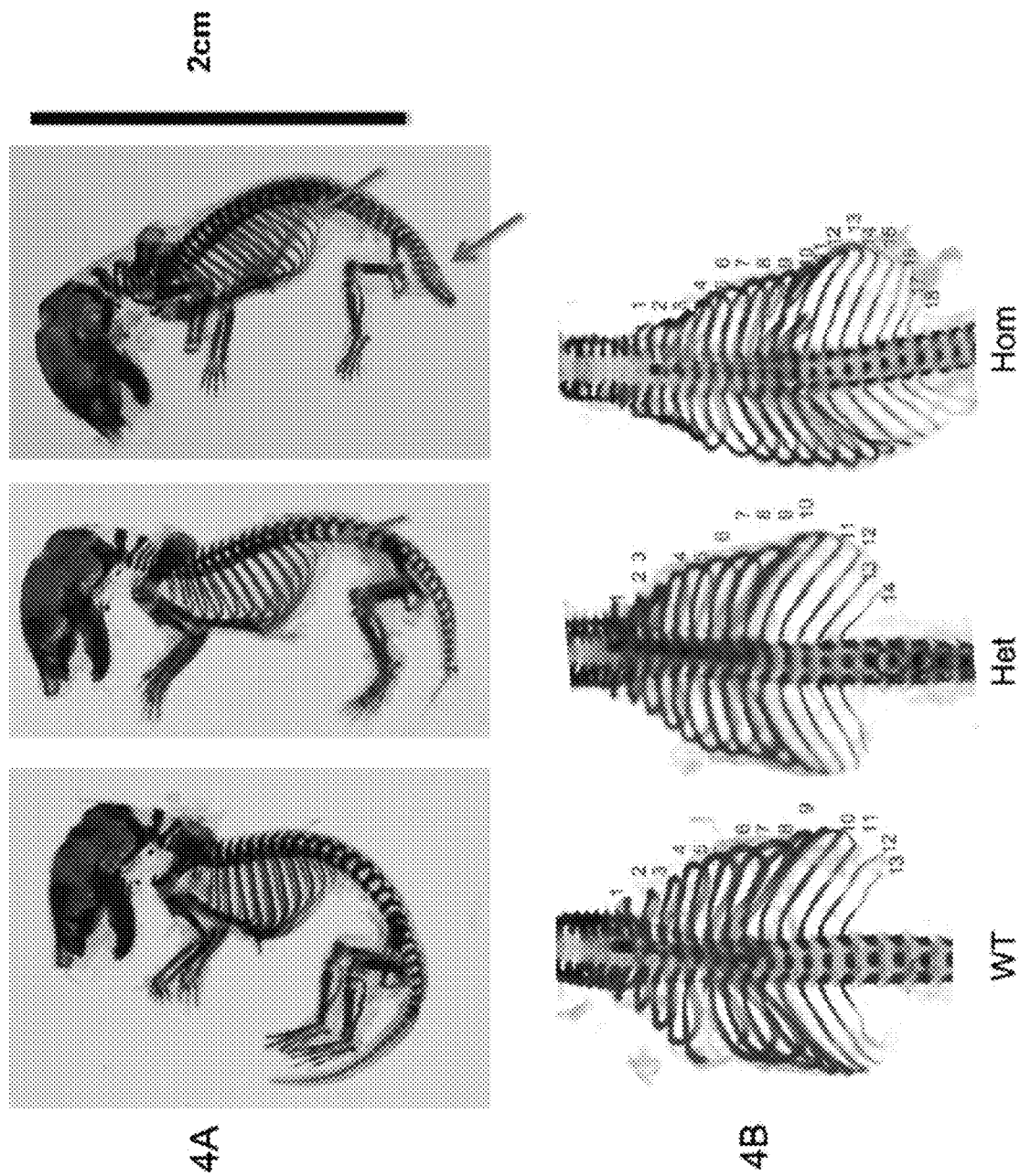
Figure 8C:
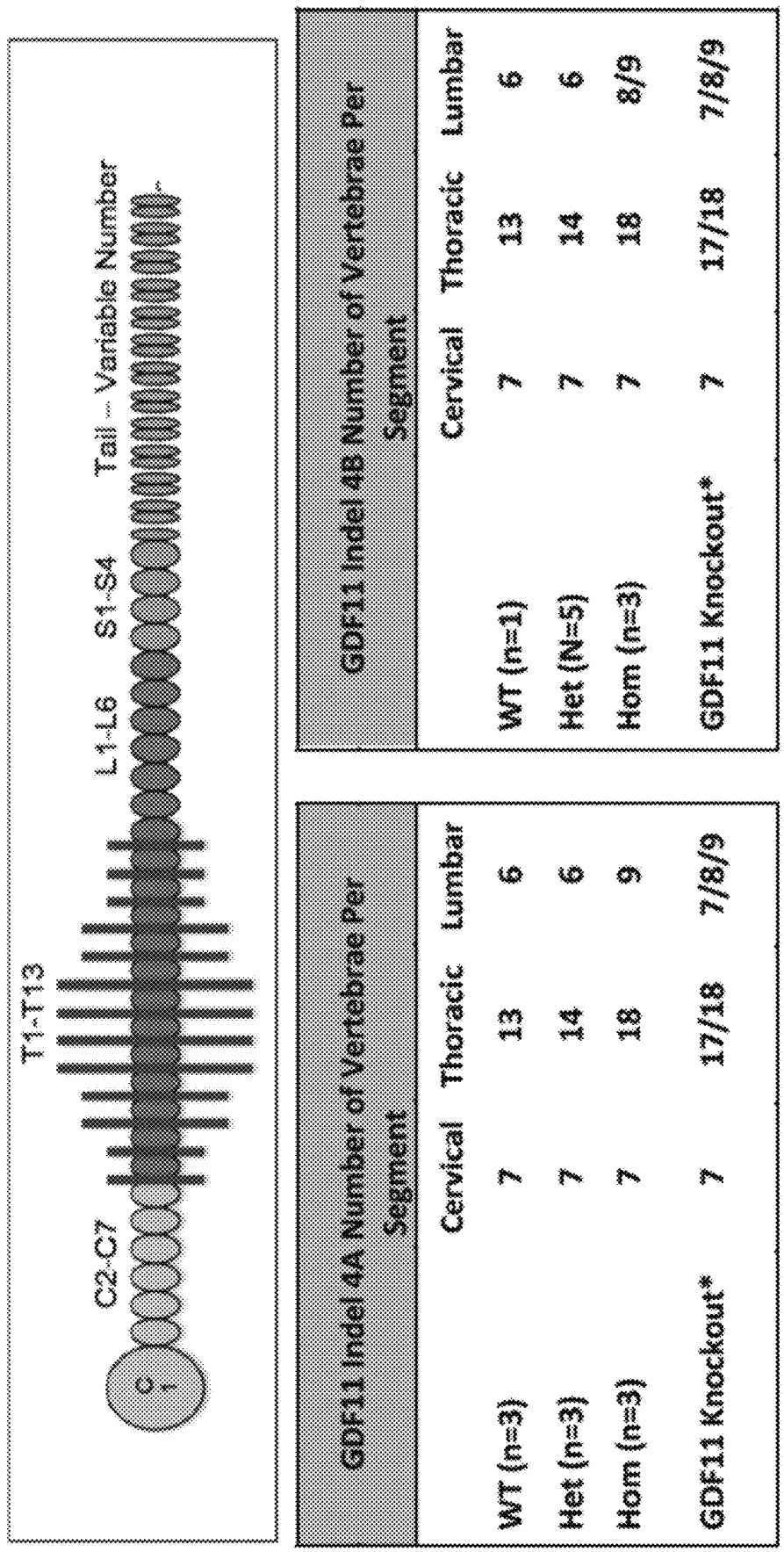
Figure 8D:
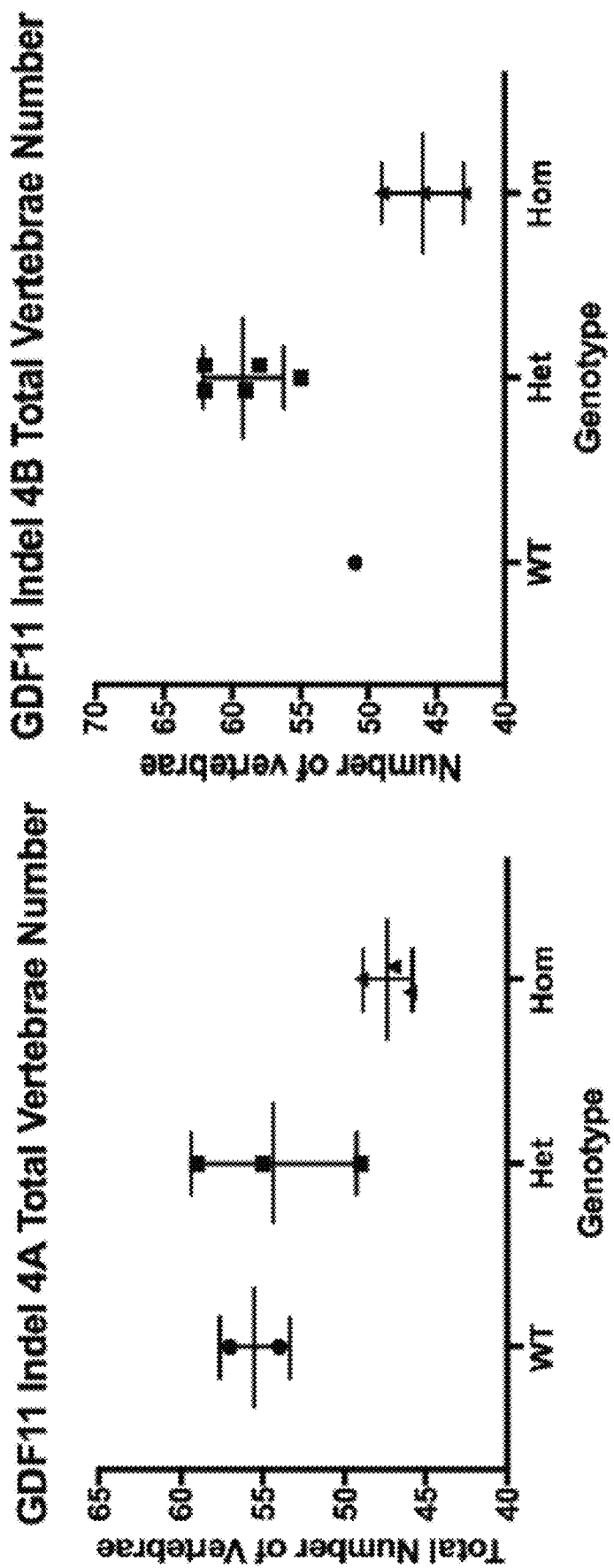

The skeletons were examined by staining with Alcian Blue and Alizarin Red in order to visualize cartilage and ossified bond. (FIGS. 8B-8D). Quantification of the vertebrae revealed a very similar pattern to the GDF11 Knockout skeletal analysis performed by McPherron et al. (1999). These results are consistent with the hypothesis that the 4A and 4B lines phenocopy the full body GDF11 Knockout.

Figure 9A:
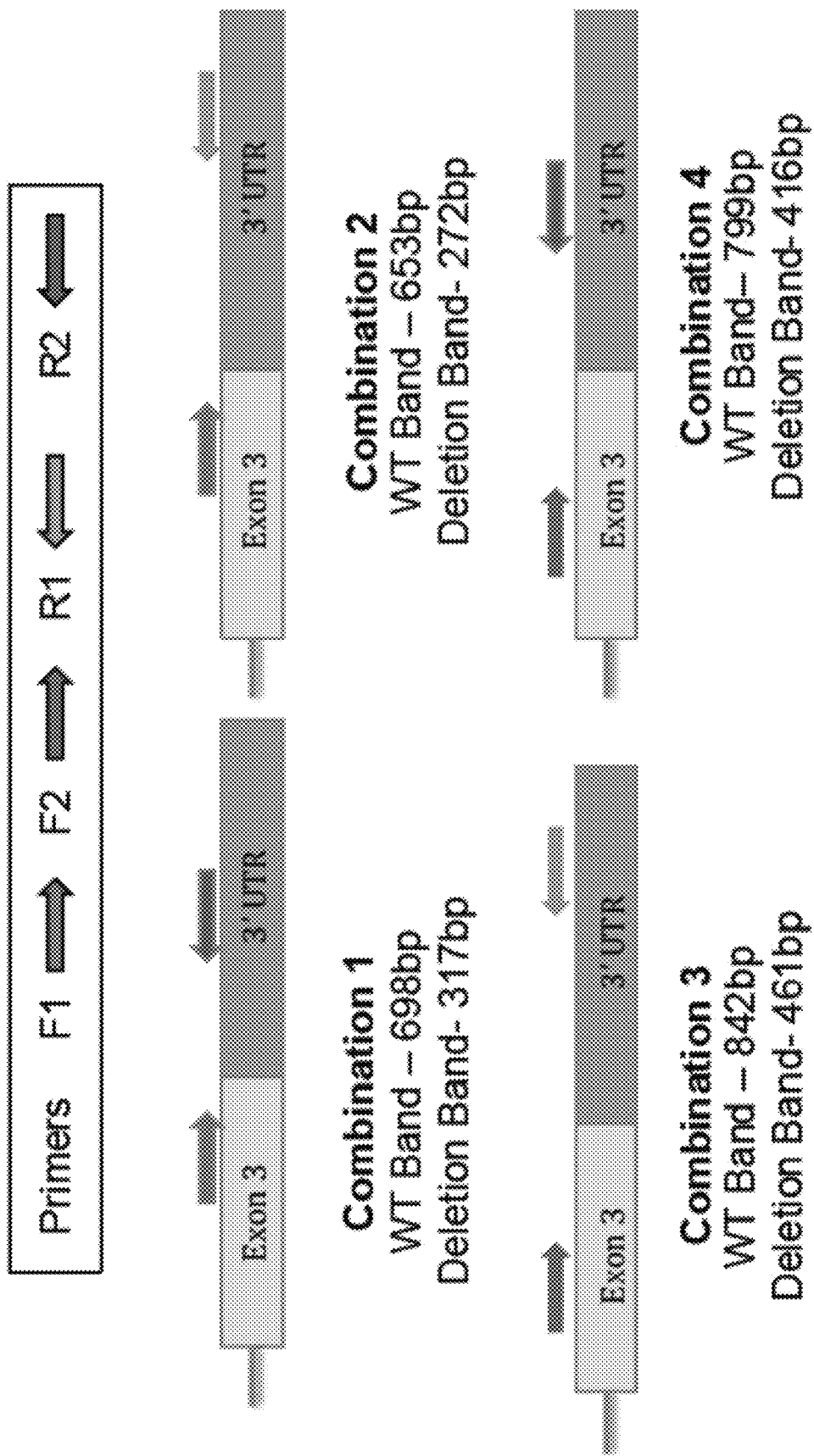
FIGS. 9A-9B demonstrate verification of viable GDF11 Indel 7 individuals.
Figure 9B:
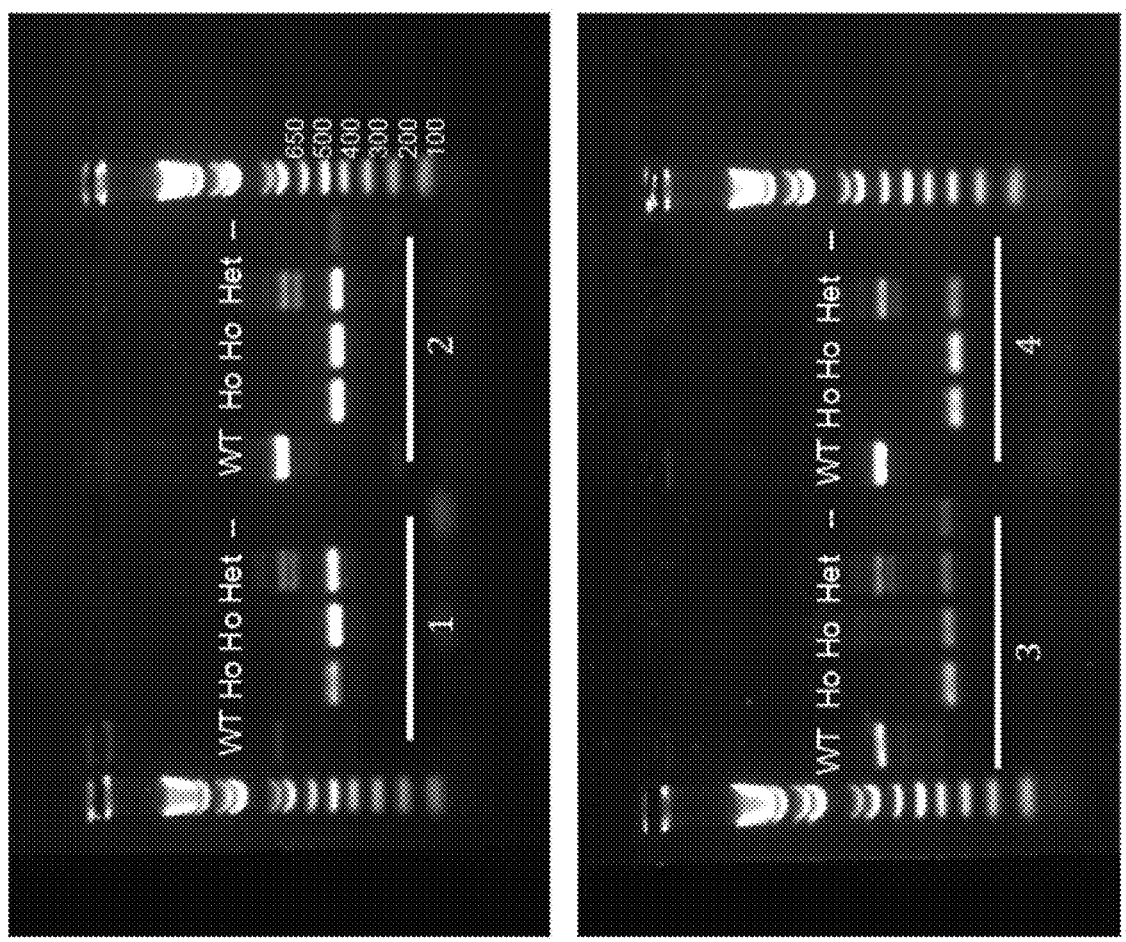

After skeletal analysis of the 4A/4B lines was complete, breeding pairs were set up for the heterozygous Indel 7 mice. It was hypothesized that this line would not phenocopy the full body GDF11 knock out mice as the deletion only leads to the addition of 2 amino acids to the end of the protein and may not be sufficient to disrupt the function of the protein. Subsequent genotyping of the pups produced showed that these pairings produced viable mice with all allele combinations, including homozygous mice, none of which displayed the classic GDF11 knockout features seen in the 4A and 4B lines, such as perinatal lethality and stunted tails. Given the integral nature of GDF11 in development and homeostasis, the presence of a GDF11 mutant that allowed for the existence of viable homozygous mice was surprising. To validate this finding, four primer combinations were used that spanned the 3rd exon and the 3' UTR of GDF11 at different sites (FIG. 9A). The resulting gel showed bands for each genotype—wild type, homozygous, and heterozygous—that matched the expected size given the different primer combinations (FIG. 9B). This experiment allows for confirmation of the genotype of these animals and confirms the existence of viable Indel 7 homozygotes. This unique and novel deletion presents the first opportunity to study the consequence of a GDF11 perturbation that still allows the molecule to function.

Figure 10A:
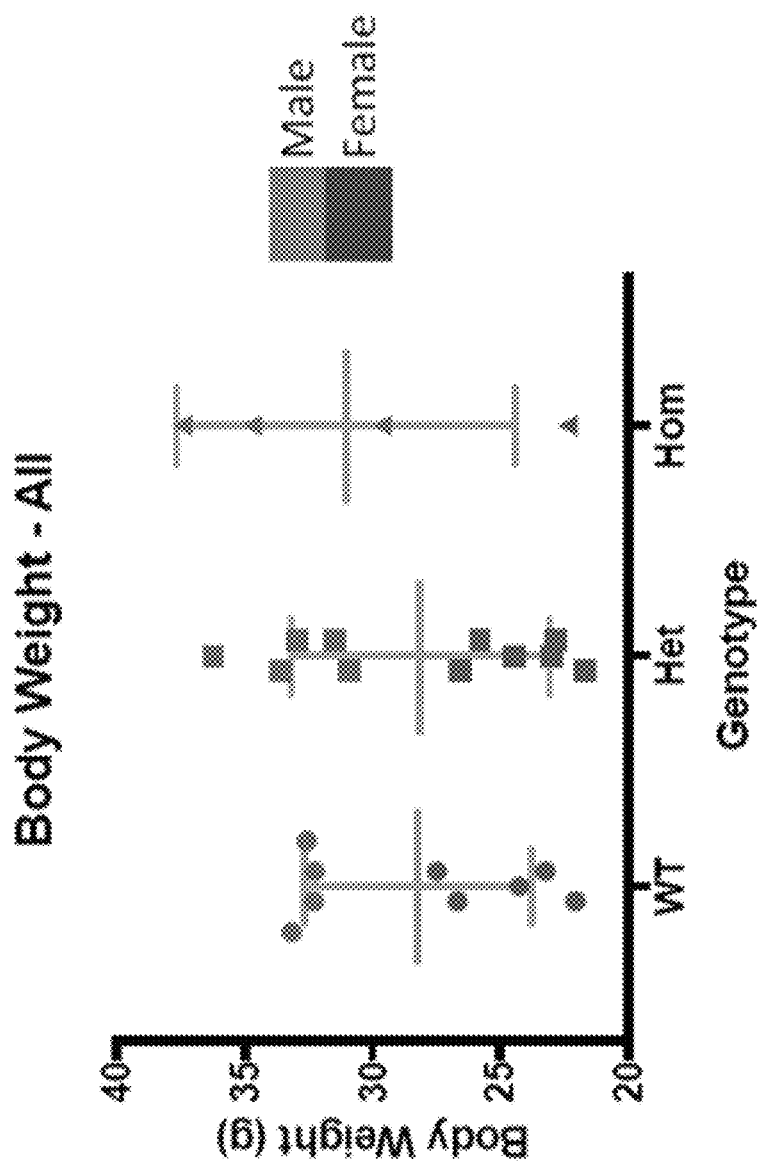
Figure 11A:
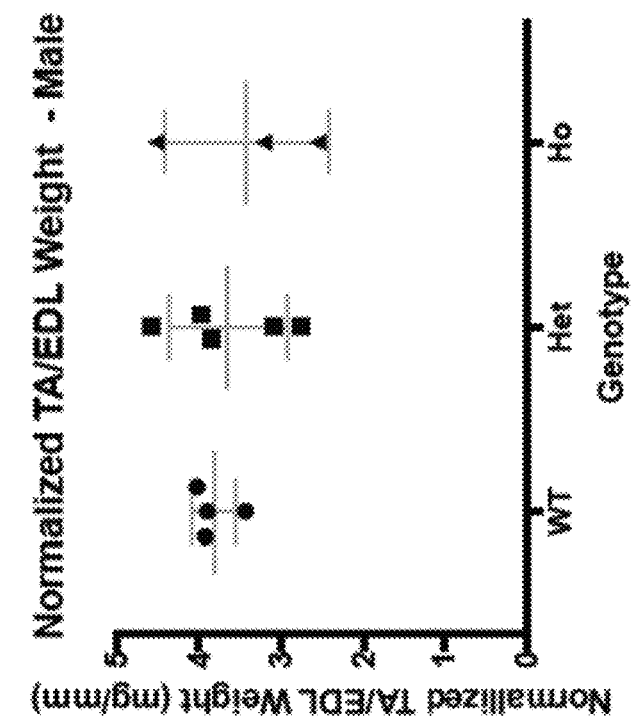
FIGS. 11A-11C demonstrate GDF11 Indel 7 cohort muscle weight and grip strength analysis.
Figure 11A:
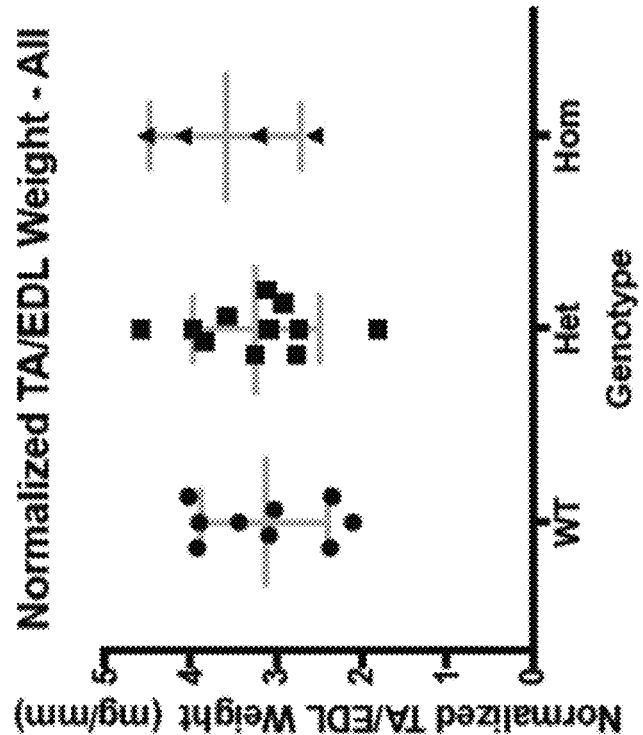
Figure 11B:
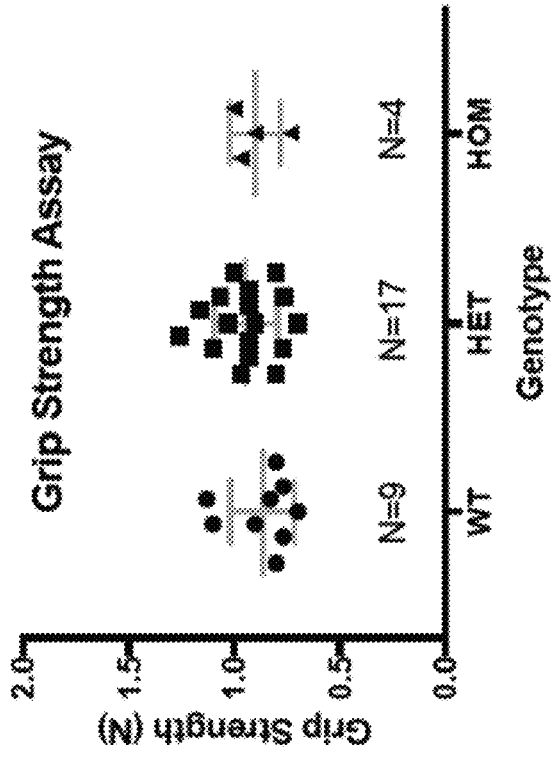
Figure 11C:
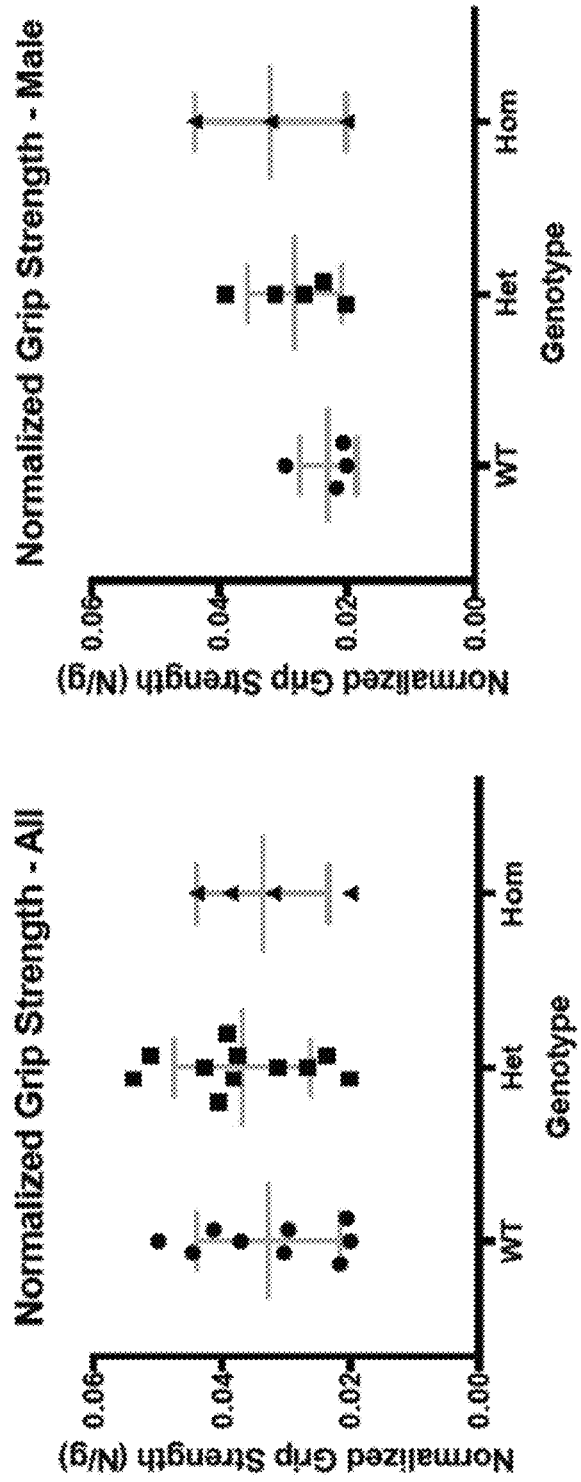

Approaching the analysis of the Indel 7 mice systematically, from organism-level to molecular-level assays, the Indel 7 mutation was examined to determine if it led to any large-scale morphological changes in the mice. Body weight measurements were taken in a cohort of 24 mice aged 5-7 months (FIG. 10A). Additionally, based on the spleen deficiencies in GDF11 Knockout mice and previous research that ties GDF11 to skeletal muscle homeostasis and heart size, the weight of the heart and spleen were analyzed to see if there were any significant changes in weight between genotypes (McPherron et al., 1999; Egerman et al. 2015; Sinha et al. 2014; Loffredo et al. 2013). These values were normalized to both the tibia length and body weight to allow for meaningful comparison (FIGS. 10B-10C). Two pools of data were used for analysis, one that used both sexes and one that only used males. The pooled female data is not shown due to the limited number of female homozygotes that were available, which prevents comparisons to that group from being interpreted. For all these values—spleen weight, heart weight, and body weight—ANOVA one-way analysis revealed no significant difference between the genotypes.

Figure 17:
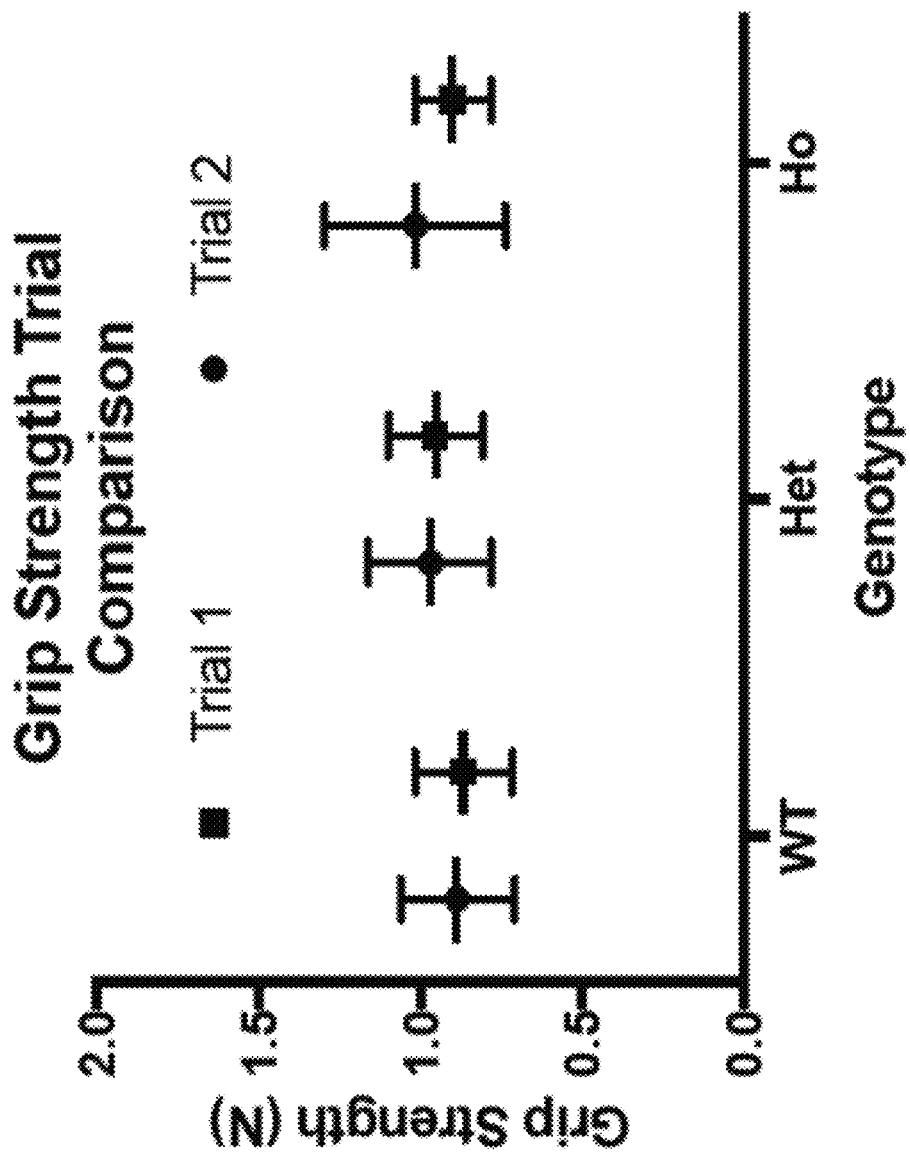
FIG. 17 demonstrates grip strength trial comparison. The average strength (Newtons) for each genotype is compared across the two grip strength trials. Similar numbers show the consistency of the assay.

Given the extensive research that links GDF11 to muscle phenotype a comprehensive analysis of the GDF11 Indel 7 mice cohort's muscle function and composition was completed (Egerman et al. 2015; Sinha et al. 2014). First, muscle at the organismal level was analyzed with a measurement of TA/EDL muscle mass and a grip strength assay meant to assess muscle strength. The grip strength was repeated twice to ensure consistent results among trials; both trials resulted in similar data points, confirming accuracy (FIG. 17). In both assays, there were no statistically significant differences between the different genotypes (FIGS. 10A-10C).

Figure 12A:
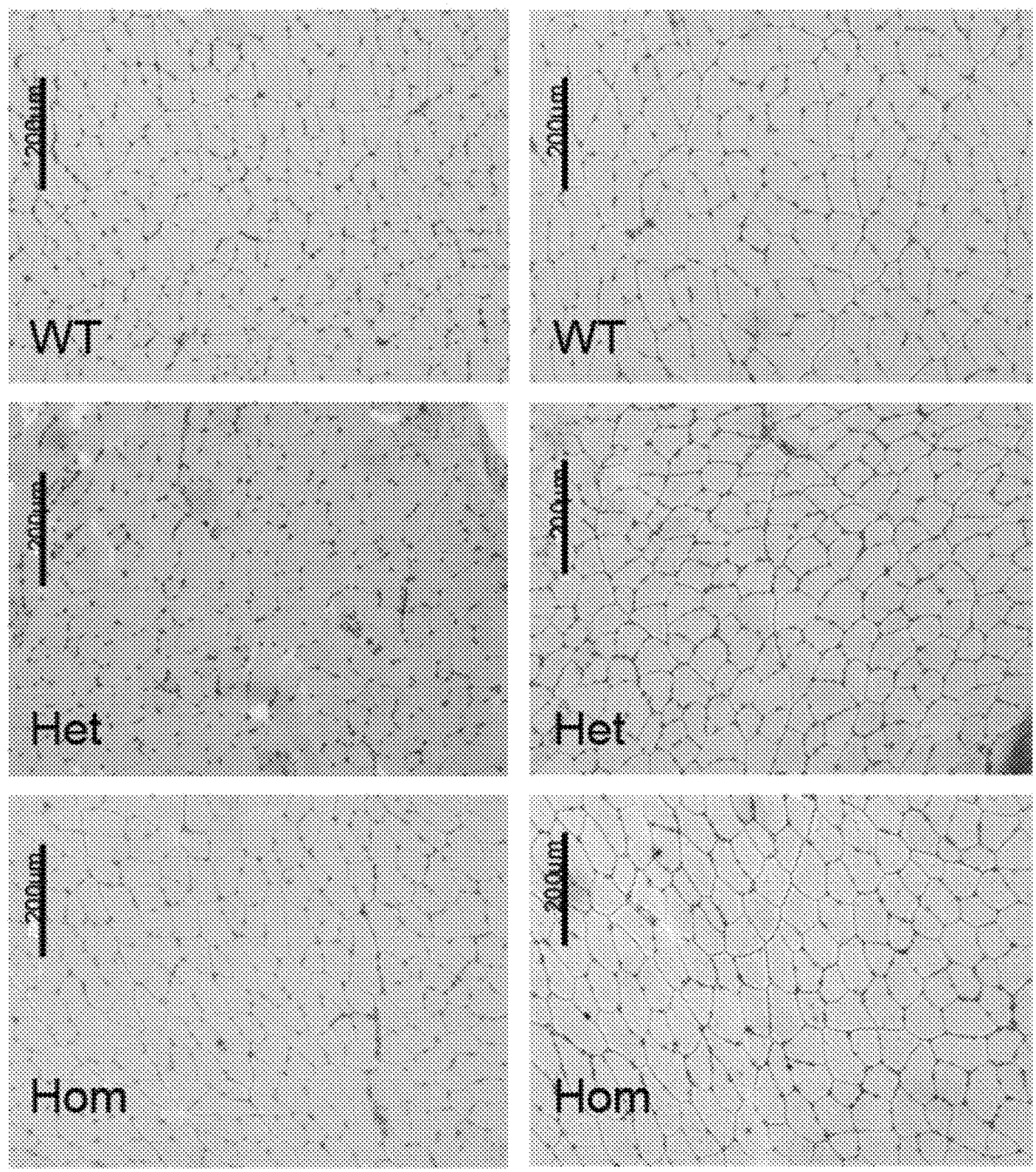
FIGS. 12A-12C demonstrate analysis of muscle fiber cross-sectional areas in the GDF11 Indel 7 cohort.
Figure 12C:
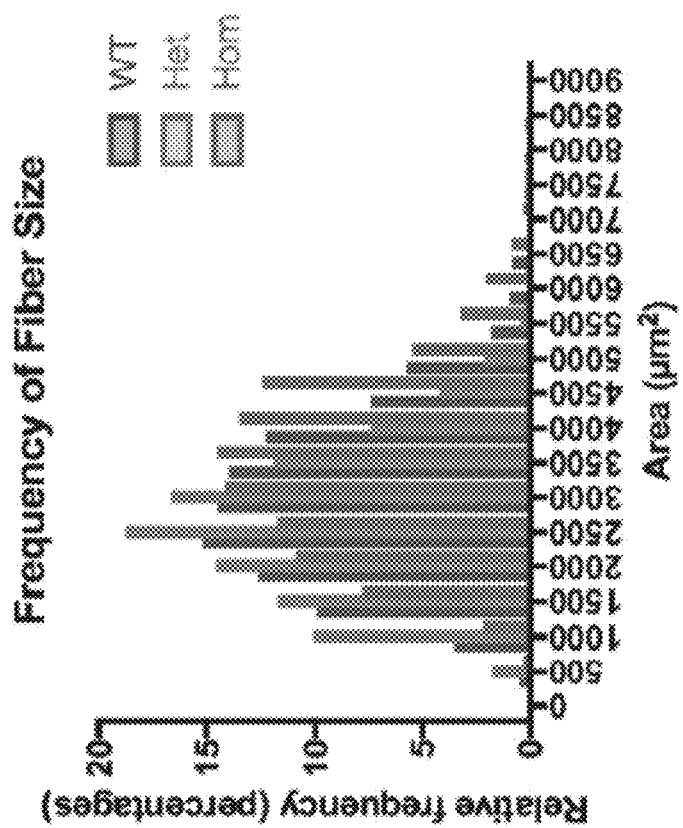
Figure 12B:
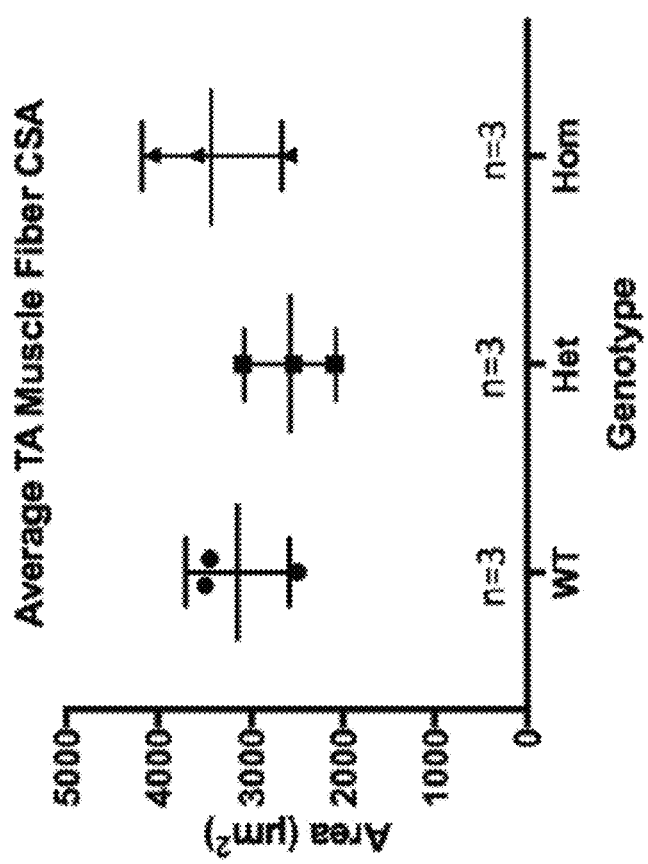

These findings were consistent at the cellular level with an analysis of sectioned TA/EDL muscle fibers, stained to allow for proper analysis, that revealed no significant differences among the average fiber cross-sectional areas across the genotypes (FIGS. 12A-12B). Further analysis looked at the relative frequencies of muscle fibers of certain sizes, generating a histogram of each genotype that could be used for comparison (FIG. 12C). Overall the frequencies were similar across genotypes and no significant difference could be found.

Continuing to the molecular assays, liquid chromatography/tandem mass spectroscopy (LC/MS/MS) was used as a way to quantify the levels of GDF8 and GDF11 in the serum of the GDF11 Indel 7 cohort. This assay provides a specific measurement of the circulating levels of GDF11 in the serum, relying on a sequence of the digested protein unique to GDF11. The mutant nature of the Indel 7 GDF11 protein, with its two amino acid addition, should not affect the results based on the amino acid sequences used for the GDF11 detection, as seen with the provided schematic (FIG. 13A). Despite the range of phenotypes that seemed unchanged—muscle strength, spleen weight, body weight—this assay shows that there are significant differences of GDF11 at the protein level, at least in the serum, a ANOVA one-way test revealed heterozygous mice had a significantly higher level of serum GDF11 (FIG. 13B). This also stood true for a cohort that used only male mice, in an effort to control for any possible variation that might occur in serum GDF11 levels between males and females. The male cohort did reveal an interesting trend: there was a significant increase in circulating GDF8 levels in the homozygous mice, however this could be due to statistical variation driven by the low sample numbers in that cohort (FIG. 13C).

Figure 14A:
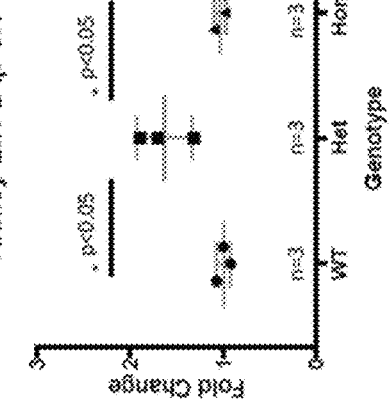
FIGS. 14A-14B demonstrate real time quantitative PCR analysis of spleen and kidney tissue from the GDF11 Indel 7 cohort.
Figure 14A:
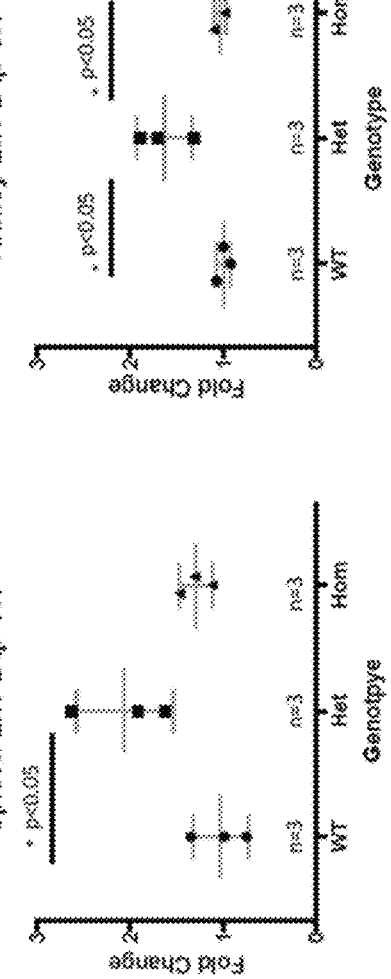
Figure 14B:
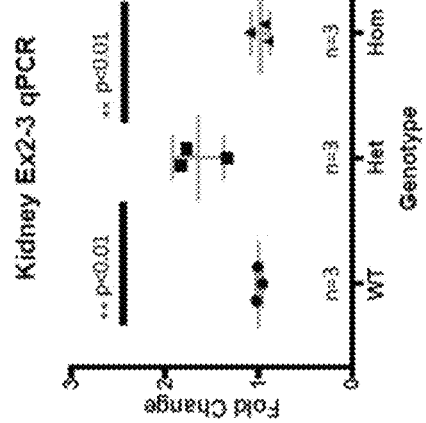
Figure 14B:
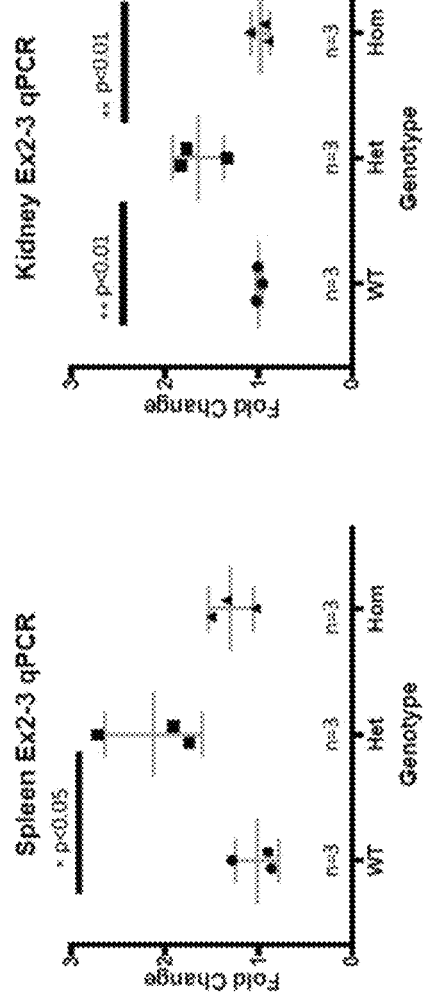

Moving forward with molecular assays, mRNA expression differences in the spleen and kidney were looked at using Real-Time quantitative PCR. These tissues were chosen because of their usually high levels of GDF11 mRNA expression in young animals (Loffredo et al., 2013). Following the trend seen in the LC-MS/MS assay, the heterozygous mice showed an increase in GDF11 mRNA expression across both tissues with an average fold change of 2.06 in spleen and 1.63 in kidney. However, between WT mice and the homozygous mice there is no significant change, with average fold changes of only 1.30 and 1.04 in the kidney and spleen respectively (FIGS. 14A-14B).

Figure 15A:
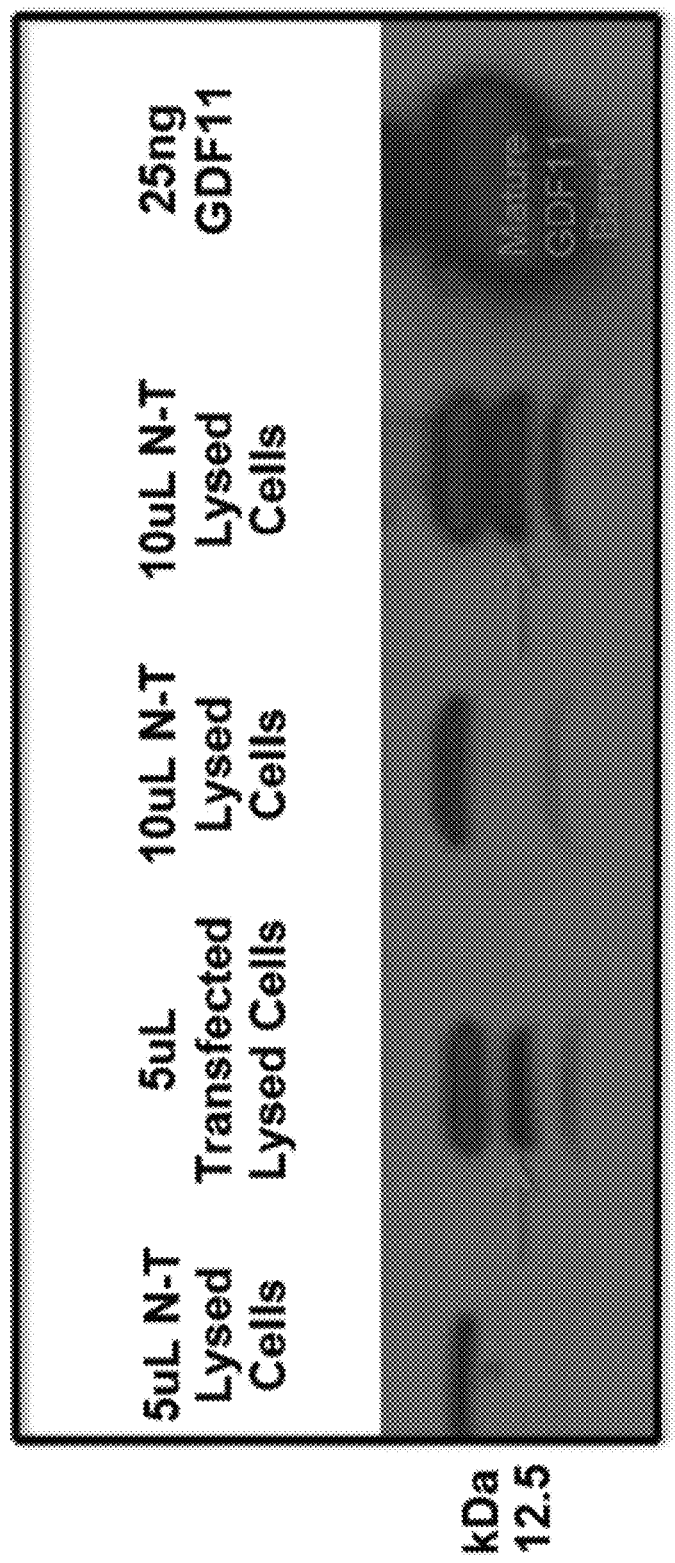
FIGS. 15A-15D demonstrate western blot and CagA luciferase assay of the mutant Indel 7 GDF11 protein.
Figure 15B:
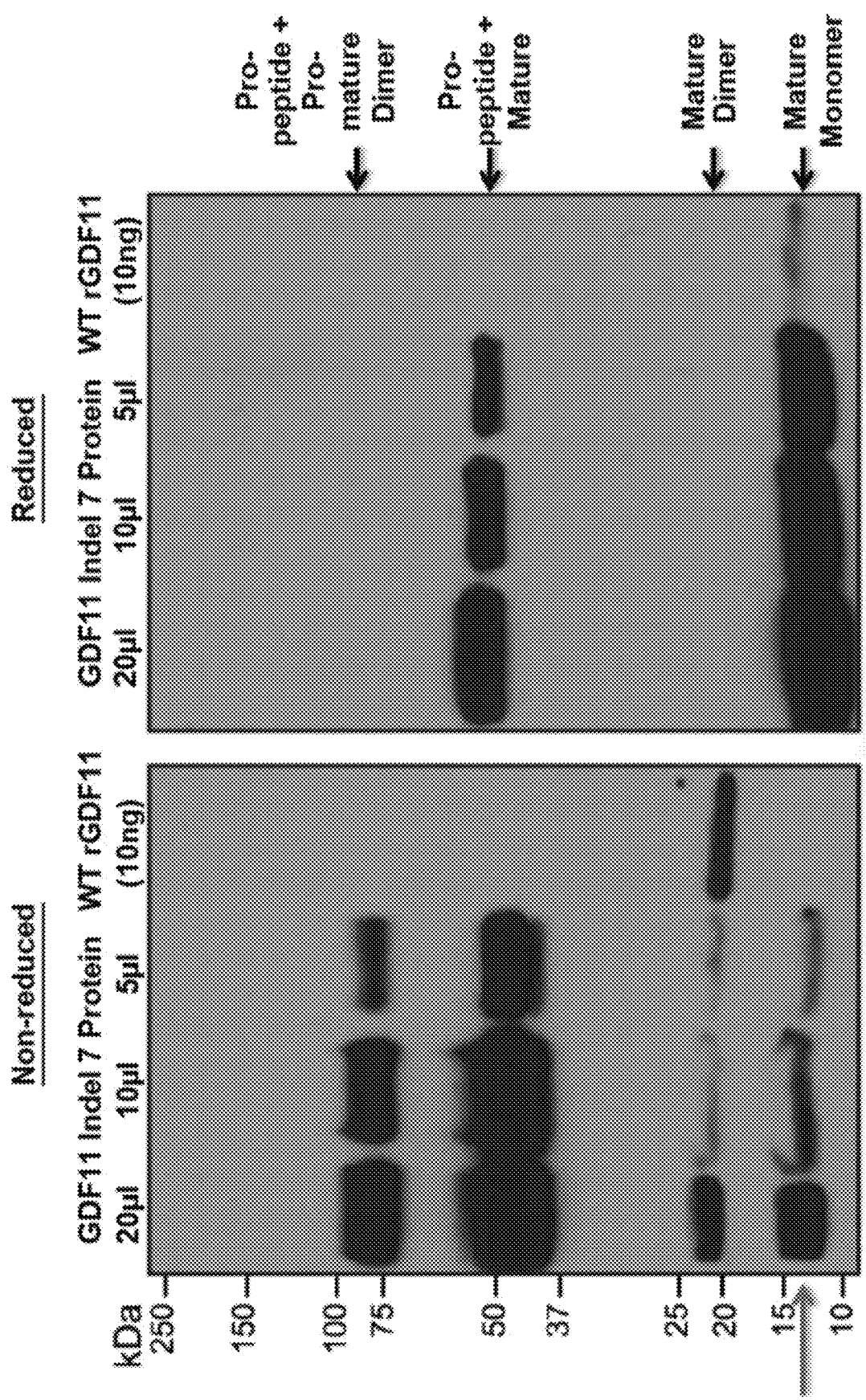

Finally, moving down to the level of the mutant protein itself, an assay was planned to see if the mutant Indel 7 protein—with a tryptophan and a glutamic acid attached to the C-terminus—has a differential potency when compared with wild-type recombinant GDF11. The mutant GDF11 was successfully created using quick-change mutagenesis and transformed into competent E. Coli cells. The resulting cells were confirmed to be producing GDF11 through western blot (FIG. 15A). When comparing reduced and non-reduced western blots of the GDF11 Indel 7 mutant protein it became apparent that the GDF11 monomer was present in a non-reduced blot, indicating that the mutant protein was present in the serum and lacks the covalently bonded disulfide bridge (FIG. 15B). When looking at the structure of the protein, the predicted addition adds the amino acids at the end of the c-terminus, near the site of the disulfide bridge between the two monomers, and likely disrupts the formation of the mature dimer (FIG. 5).

Figure 15C:
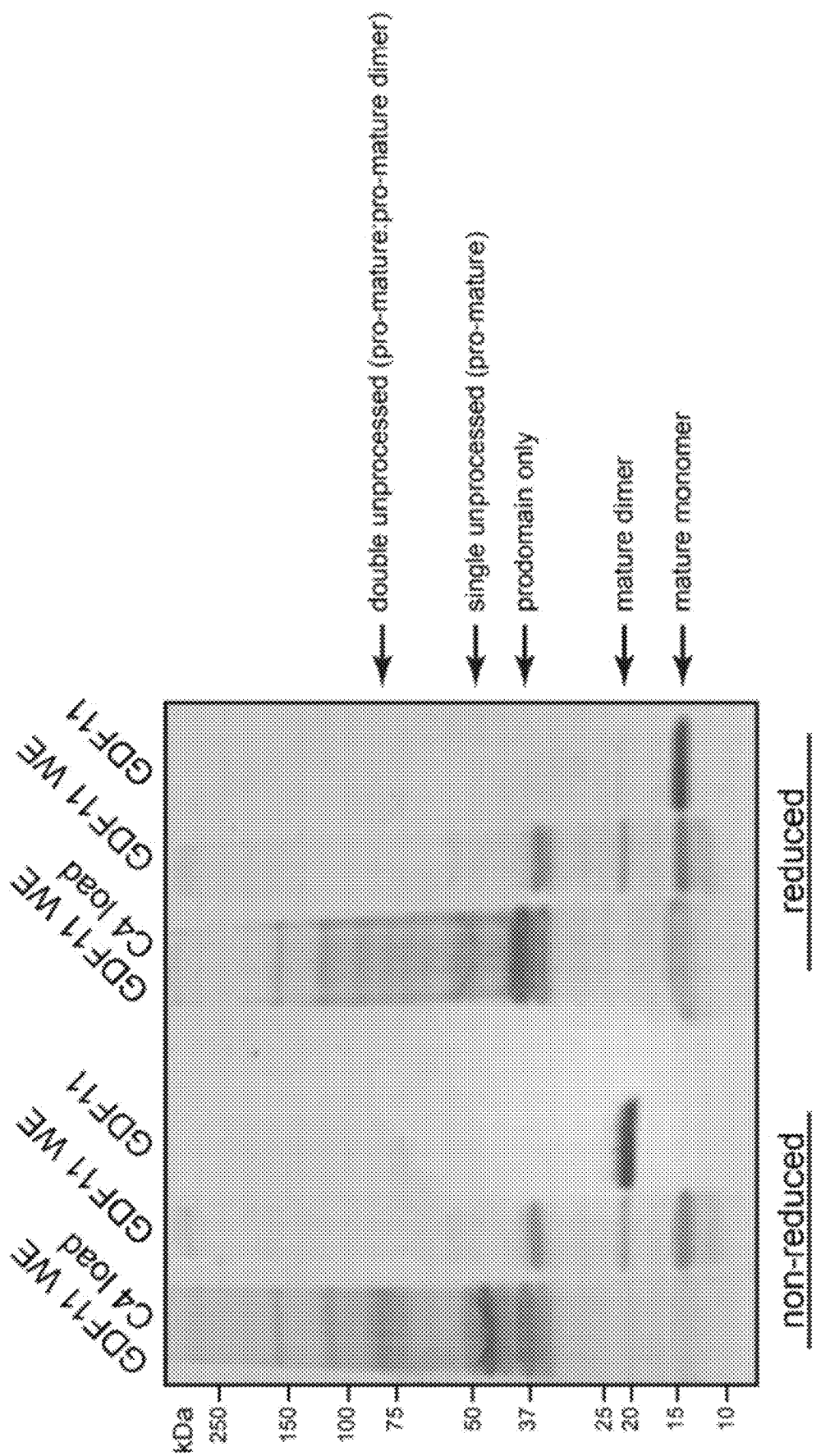
Figure 15D:
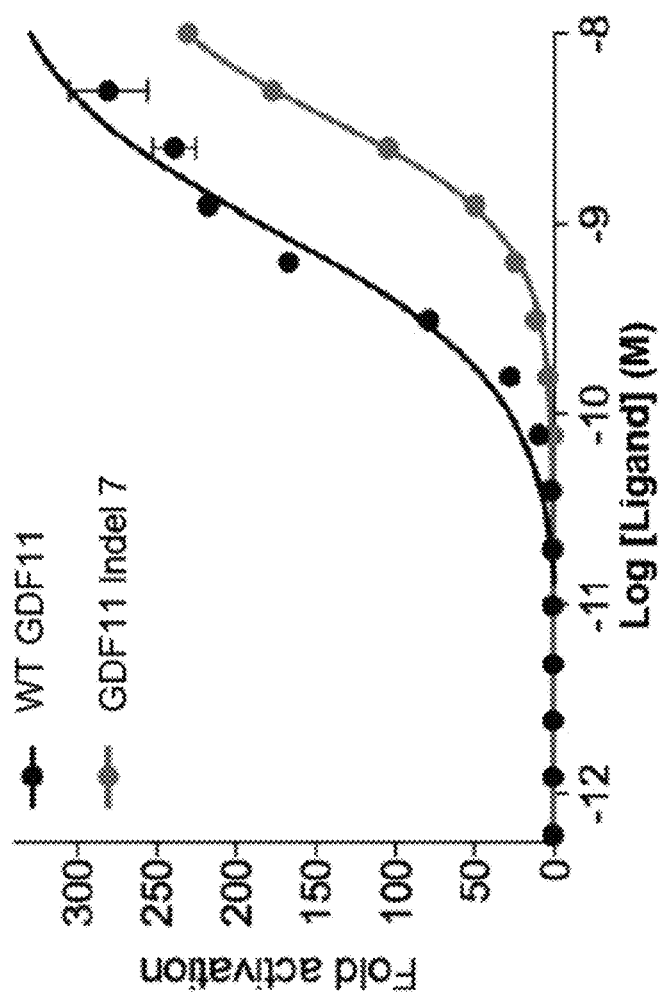
Figure 16:
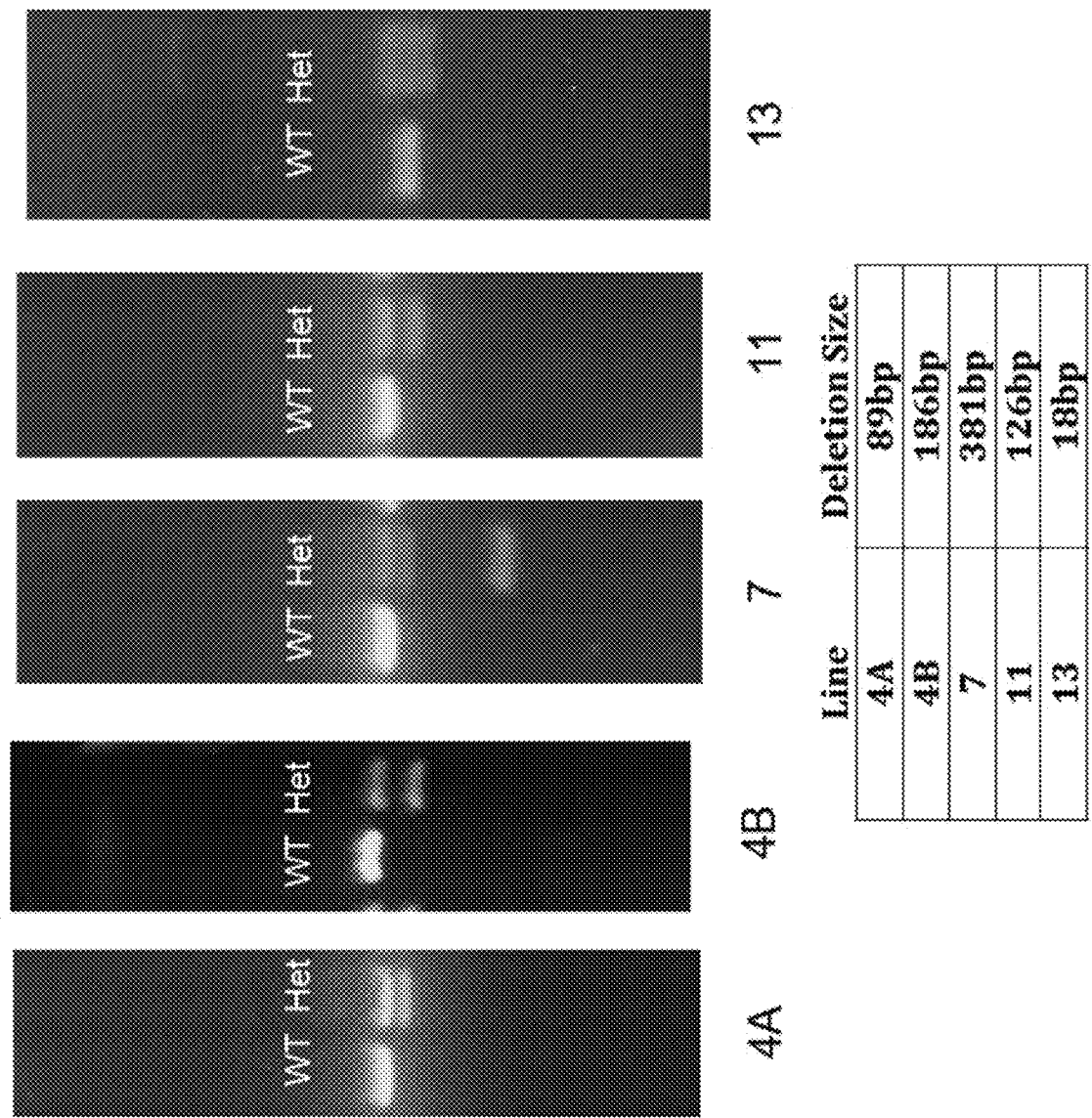
FIG. 16 provides a gel showing relative GDF11 Indel deletion sizes. Images of genotyping done for the Indel lines, each showing a WT band followed by a Het band, to illustrate the relative sizes of the bands throughout the lines. Each gel was run for approximately 30 minutes on a 1% gel.

With the protein created, a HEK-(CAGA) luciferase assay was used to create a dose response curve and assess the potency of the molecule. The EC50 value, the concentration of a molecule needed to activate a halfway response and a common tool to assess potency, differs between the WT and mutant proteins, with EC50 values of −9.035 and −8.441 respectively (FIG. 15C). This indicates it takes 3.93 times the concentration of the mutant protein to create the same response. Future assays will include controls such as HEK293-produced WT GDF11 instead of rGDF11 from PeproTech®; however, these results strongly suggest that this molecule lacks the characteristic covalent bond found in mature members of the activin family and might have unique binding properties and differential potency.

Figure 7B:

Moving forward, two lines remain to be characterized, Indel 11 and Indel 13. For Indel 11, there were an insufficient number of mice to perform timed mating and undergo the subsequent dissection protocols alongside the 4A/4B mice so this line was backcrossed with C57Bl/6 mice to expand the colony for future study. Based on their mutation, an addition of 32 amino acids—a similar addition as the 4B line, it was hypothesized that this deletion likely phenocopies the GDF11 knockout mice as well (FIG. 6). The Indel 13 line was sequenced in preparation for future studies and should also be analyzed due to the unique nature of the deletion in comparison to the others, with minimal perturbation of the 3' UTR (FIG. 7B). However, it is hypothesized that the Indel 13 mutant protein phenocopies the GDF11 Knockout mice, with a predicted 22 amino acid addition to the end of the protein.

Discussion

The systematic characterization of the GF11 Indel mice was begun with a skeletal analysis of the 4A/4B lines. Given the consistency of the results with the McPherron et al. skeletal analysis of GDF11 knockout mice, the data indicates that the 4A and 4B mouse lines lack functional GDF11 and are perinatal lethal (1999). Mice heterozygous for this deletion showed a minor elongation of the thoracic vertebrae and homozygous mice showed more severe, anteriorly directed homeotic transformations with 18 ribs and shortened, stunted tails (FIG. 8B). This supports our hypothesis that the lengthy addition of amino acids in these mutant proteins led to a nonfunctional variant. This skeletal characterization revealed that an addition of only 13 amino acids to GDF11, as seen with the 4B Indel mutation, created a skeletal phenotype that mirrored that of a GDF11 knockout mouse (FIG. 8C). These results depict a novel instance whereby the addition of multiple amino acids to the C terminus of the GDF11 protein results in a nonfunctional protein.

Moving forward, when characterizing the Indel 7 line it became clear that the 381 bp deletion in the 3' UTR, and the corresponding two amino acid addition to the protein, yielded a functional variant of GDF11, despite possible changes in structure and potency (FIG. 9, FIG. 15). Multiple assays meant to characterize organism-level phenotype, properties such as muscle strength, muscle weight, body weight, and organ weight, revealed no significant differences between the different genotypes—WT, Het, Hom—in young animals (FIGS. 10-11). Refocusing to the cellular level, looking at muscle fiber CSA, there was also no significant difference in the average fiber size and relative frequencies of different fiber sizes (FIG. 12). The lack of obvious phenotypic differences, and the known importance of GDF11 in development and homoeostasis, shows that this protein is functional.

However, there still seems to be variation with the Indel 7 mutant mice when examined at the level of molecules—mRNA and protein (FIGS. 13-14). In the tissues examined, spleen and kidney, the heterozygous Indel 7 mice displayed a modest increase in GDF11 mRNA expression. Correspondingly, the LC-MS/MS assay did reveal that heterozygous individuals have increased levels of GDF11 in the serum, followed with a trend that failed to reach statistical significance that also shows an increase in homozygous mice. These increases are interesting and might be linked to mechanisms that upregulate the WT allele to compensate for the presence of the mutant allele. This would mean however that there are molecular mechanisms in place that could detect the differences in the way the two molecules look or behave, perhaps through differential binding to antagonists or receptors. Additionally, the possibility exists that regulatory regions in the 3'UTR of GDF11 were deleted with the Indel 7 mutation and the lack of regulation led to the increased expression seen; however, the lack of increased mRNA expression in the homozygote animals, which have two alleles that would lack the supposed regulatory region does not support this hypothesis.

Interestingly, when limiting the analysis of LC-MS/MS data to only male mice, the homozygous GDF11 Indel 7 mice showed an increase in serum GDF8 levels—this might be seen as a connection of the two molecules to correct deficiencies among the similar looking proteins (FIG. 13C). Due to the limited number of individual animals available when the data is analyzed for males only, there is also the likelihood that this result is due to random variation, especially since this significance drops to be only a trend in the mixed male and female pool. If verified with larger numbers of mice, this result could point to a possible compensatory relationship between the GDF8 and GDF11 protein—where one is up regulated in response to the mutation of the other. An analysis of GDF8 mRNA expression in the selected tissues—Kidney and Spleen—would be an interesting way to verify these findings. If the Indel 7 homozygous mice show an increase in GDF8 mRNA expression, this could support the significance of the mass spec data, and suggest a compensatory relationship between members of the TGF-β superfamily.

The lack of large-scale phenotypes is interesting given the results of the protein analysis assays: the non-reduced western suggests that the addition of the proteins tryptophan and glutamic acid to the end of the C-terminus prevent the disulfide bridge from forming, leading to an active protein that is mostly non-disulfide linked and mature monomers to be excreted (FIG. 15B). The addition of the large, hydrophobic tryptophan could possibly help the molecule stay bound by hydrophobic interactions. This structural change could affect the binding of the molecule to antagonists, receptors, and affect the overall stability of the protein. Additionally, the preliminary results from the HEK293-(CAGA) luciferase assay, with the EC50 value showing the mutant protein as needing an increased concentration of the molecule to achieve the same response as the WT protein, support that this unstable structure affects the ability of the ligand to induce a response (FIG. 15C). These analyses are preliminary, and utilize rGDF11 from PeproTech® rather than purified GDF11 produced from HEK293 cells like the mutant GDF11 Indel 7 protein, which could possibly affect the results of the western blot. However, the current data suggests an unstable, unique protein that could prove to be useful in understanding how the structure of GDF11 affects its function (FIG. 15C). More research needs to be done to confirm the actual structure of the molecule and analyze the possible changes in binding affinity, and any more corresponding phenotypic changes that could occur from this change in structure.

Additionally, the many forms of GDF11—free, latent, and complexed with extracellular antagonists, such as GASP-1 or GASP-2—challenge an interpretation of the LC/MS/MS results (Harper et al., 2016). The state of the increased amount of GDF11 in the Indel 7 heterozygous mice is unknown at the present. It could be possible that increased binding of the extra protein by antagonists, or a lack of protelytic enzymes needed to create the active state of GDF11, prevents the increased production of mRNA and protein from leading to any detectable large-scale phenotypes. A follow-up experiment might be able to use an assay with the mutant GDF11 protein created to put this to the test, looking for differential binding of the Indel 7 mutant GDF11_WE_Stop to antagonists such as GASP-1.

The GDF11 Indel mice also test some preconceived notions of GDF11 function. Specifically, previous attempts to attach tags to the end or side of the molecule with marker proteins, such as GFP, resulted in dysfunctional proteins and perinatal lethal mice (R. Walker, personal communication, September 2017). The viability of homozygous GDF11 Indel 7 mice proves that certain small amino acid changes could be made to the GDF11 protein that largely preserve function. This might be useful in the context of creating additional amino acid changes that can be capitalized to make GDF11-specific antibodies, allowing for the development of western blots or ELISA assays that can be used to characterize tissue-specific GDF11 protein levels.

The difficulty of conducting experiments on GDF11—with its incredible diversity of downstream targets, large number of activation states and antagonists, and structural similarities to other proteins—pushes scientists to come up with creative ways to research the molecule. The GDF11 Indel mice bring up larger points about the usefulness of CRISPR-Cas9 in creating a wide variety of mutations around a specific region of a gene. This shotgun approach mirrors genetic screens that use widespread mutagenesis to find areas of interest throughout the genome, with the added benefit that a specific region can be targeted. Important regulatory regions could be discovered with Indel lines that remove the 3'UTR while keeping the expressed sequence intact. Alternatively, small amino acid additions can be made to test the functional limits of a protein, informing researchers curious about the possibility of adding reporter sequences tags to proteins. The upper limit of addition that a protein can handle could be determined by looking at when nonfunctional variants start to occur within a series of additions. This series of characterizations presents another example of how CRISPR-Cas9 technology can be creatively used to analyze genes of interest around the mammalian genome. With its ties to aging, GDF11 research, and all its controversy, conflict, and tremendous potential, remains important and the use of exciting new techniques to further characterize the molecule will continue to lead to new insights.

Materials and Methods

Animals

C57Bl/6 mice (Jax Laboratory Stock Number 000664) were obtained from Jackson Laboratories. Maintenance of mouse colonies and all experiments were conducted in accordance with the Guide for the Use and Care of Laboratory Animals and approved by the Harvard University Institutional Animal Care and Use Committee (IACUC).

Genotyping Protocol

DNA was extracted from tissue using 50 μl of DNA QuickExtract™ according to manufacturer protocol. All genotyping was done using 25 μl reactions consisting of 12.5 μl 2×Q5 Master Mix, 8 μl of nuclease free water, 1.25 μl of GDF11 primers (See GDF11insitu_F, GDF11T7E1_F2, GDF11insitu_R, GDF11sUTR_R) kept at 10 μm concentration, and 2 μl of sample. The samples were run in a 1% agarose gel for approximately 40 minutes to 1 hour.

Sequencing the Deletions

To sequence the GDF11 Indel deletions, mice containing the deletion were genotyped using the protocol outlined above and the bands containing the WT GDF11 sequence and the Indel deletion were excised. The DNA was extracted from these bands using a QIAGEN QIAquick® Gel Extraction Kit according to manufacturer protocol. In order to amplify the DNA obtained, a TOPO® cloning reaction was done according to manufacturer protocol: The purified DNA was cloned into the Zero Blunt TOPO® Vector (ThermoFisher). The colonies were plated and grown overnight at 37° C. A colony PCR reaction was set up to determine colonies to be sent for sequencing using 25 μL reactions consisting of 1 μl 10 μM primers, 10.7 μl of nuclease free water, 2.5 μl of 10× Buffer, 1.5 μl of $MgCl_2$, 1.25 μl of DMSO, 6.25 μl of 5M betaine, 0.5 ml of 10 mM dNTPs, and 0.25 μL of taq polymerase. Colony samples were run on a 2% Agarose gel. Colonies that showed an incorporated product were sent for sequencing through Genewiz using the T7_F and M13_R primers (See T7_F, M13_R). The DNA sequence of the Indel 13 deletion was inferred through alignment to the WT GDF11 sequence using the GENEIOUS platform.

Timed Breeding and Embryo Dissection

Heterozygous GDF11 Indel 4A mice were set up for breeding, followed by separate timed breeding for the 4B deletion, and examined for plugs the following morning. Successful plugs were labeled as 0.5 days with the planned harvest of mice embryos at late stages of gestation. The embryos shown for FIG. 7 were harvested at E18.5 and E17.5 for the 4A and 4B deletions respectively. Mice were taken from the uterine horns, photographed, and frozen dry at −20° C. before being processed with the skeletal preparation protocol.

Skeletal Preparation Protocol

From timed breeding set-ups, day 17.5 and day 18.5 old embryos were eviscerated, with skin, major organs, and fat being removed by forceps. The embryos were then fixed in 100% ethanol for 24 hours and dehydrated in 100% acetone for 24 hours. The skeletons were then stained with 5% acetic acid in 70% ethanol containing 0.3% Alizarin red and 0.1% Alcian blue for approximately 72 hours. After staining, skeletons were cleared in a 1% potassium hydroxide and glycerol solution, increasing the percentage of glycerol, from 20% to 50% to 80%, after every 24-hour period. Embryos were imaged and stored in the final 80% glycerol, 1% KOH solution.

Grip Strength Protocol

For measurement of in vivo muscle force, a mixed sex cohort of GDF11 Indel 7 mice, aged 5-7 months were allowed to grasp onto the horizontal metal grid of the grip strength meter (Columbus Instruments, Columbus, Ohio) with only their forelimbs and then were pulled backwards 3 times. The force applied to the grid each time before the animal lost its grips was recorded in Newton. The average of the three pulls was used to calculate a value that was then pooled into the separate genotypes. Both calculations that normalized the average pull force to body weight and calculations that did not normalize were analyzed.

Mass Spec Serum Analysis

Whole blood from GDF11 Indel 7 cohort was collected from the tail vein into BD Microtainer® Tube with Serum Separator Additive and left to incubate for approximately 30 minutes. BD tubes were spun at 2000 RPM for 10 minutes in a 4° C. micro centrifuge and stored at −80° C. Collected serum was sent for liquid chromatography/tandem mass spectrometry (LC/MS/MS) assay for GDF11 quantification developed by the Brigham Research Assay Core Laboratory at Brigham and Women's Hospital.

Organ Dissection

A cohort of 24 mixed sex (12 male/12 female) GDF11 Indel 7 mice were killed through $CO_2$ asphyxiation and their spleen, TA/EDL muscle, kidney, and heart were harvested for analysis. The heart was dissected, placed in PBS to be cleaned, and palpated on paper towel to release any blood clots before being weighed. The spleen and kidney were dissected, weighed, and snap-frozen in liquid nitrogen for later mRNA analysis with RT qPCR. The TA/EDL muscle was weighed, placed in a container of chilled methyl butane resting in liquid nitrogen for 30 seconds, and placed in liquid nitrogen for 30 seconds, before being stored at −80° C. for later sectioning and staining. The tibia bone was cleaned and measured using calipers.

Muscle Staining/Histology

Muscles were dissected and cryopreserved in liquid nitrogen-cooled methylbutane. All Muscle Fiber CSA analysis was done with male mice aged 5-7 months. TA/EDL muscle was dissected, weighed, and cryopreserved. Muscles were sectioned at regular intervals throughout the length of the muscle, collecting slides every 200 μm. Selected slides were put though H&E staining with Harris Hematoxlyn (3 minutes) and Scott's Bluing (3 minutes). One stained section from each mouse was chosen for analysis. The cross sections are at differing depths and were chosen for analysis based on the size and completeness of the tissue collected. 3 photos were taken across the chosen section. 50-100 fibers were randomly chosen for CSA measurement using the Axio Vision® measuring tool from each photo. The average CSA for each mouse was calculated using the pooled fiber size measurements (n=178-246 for each mouse). Those results were then pooled based on genotype giving 3 mice per genotype (n=3).

Quantitative PCR Analysis

Spleen and Kidney from the Indel 7 cohort were dissected and snap-frozen in Liquid Nitrogen. The tissue was later homogenized with 1 ml of TRIzol™ Reagent and an IKA® T10 basic ultra-turrax homogenizer. Invitrogen TRIzol™ Reagent was then used to isolate RNA from the tissues per the manufacturer protocol. RNA was quantified using Nanodrop and equal amounts of RNA were added to cDNA reactions. cDNA Synthesis was carried out using Qiagen SuperScript™ III First-Strand Synthesis SuperMix for qRT-PCR per the manufacturers protocol. Obtained cDNA was then used for quantitative PCR using an ABI Prism 7900HT sequence detection system in combination with SYBR® Green Real-Time PCR Master Mix (ThermoFisher) per manufacturer protocol. 2 primers sets were used: one that spanned GDF11 Exon 1-2 and one for GDF11 Exon 2-3 (See GDF11 Ext-2 F, GDF11 Ext-2 R, Ex2-3 F, GDF11 Ex2-3 R, Beta-Actin F, Beta-Actin R). The PCR conditions consisted of one cycle of denaturation at 95° C. for 20 sec and 40 cycles of amplification consisting of a denaturation step at 95° C. for 1 sec and annealing/elongation step at 60° C. for 20 sec. Transcript levels were normalized to the housekeeping gene Beta-Actin in the same preparation, and the fold change relative to young samples was calculated as 2(−ΔΔCT).

Quick Change Mutagenesis

Primers (See Forward Primer and Reverse Primer) were designed that would incorporate a tryptophan and glutamic acid into the end of the template that consisted of a GDF8 prodomain attached to the mature GDF11 protein sequence to ensure proper expression in transfected cells. A temperature gradient from 55-65 degrees, as well as different levels of DMSO, both 4% and 8% for each sample, were used to optimize the chance that transformation in chemically competent E. Coli would occur. Two different clones were created—one with the GDF8 prodomain/GDF11 Mature and one with the GDF8 prodomain/GDF11 Mature followed by a His tag after the signal sequence. Positive colonies were allowed to incubate at 37° C. for 24 hours and then DNA was purified with a Qiagen® Spin Miniprep Kit, used according to manufacturer protocol, and sent for sequencing. Confirmed colonies that contained the desired mutation were allowed to incubate further and then DNA was isolated using a Qiagen® Maxiprep kit, used according to manufacturer protocol. The collected DNA was transfected into a Thermo Fisher Scientific Expi293 expression system in 30 mL test cultures. The cells were then co-transfected with hFurin to process the protein and allow for the mature GDF11 dimer to form. A total of 30 μg of DNA (1 μg per mL of cells) was used 25.5 ug (85%) of the mutant GDF11 DNA and 4.5 μg (15%) of hFurin with the transfection reagent PEI in a 1:3 ratio of DNA:PEI. For a control, a 30 mL test expression was done using the PRK5 Vector.

Western Blot Protein Analysis

The mutant protein GDF11_WE_Stop was transfected into Thermo Fisher Scientific Expi293 expression system cells, which were lysed for analysis after 4 days. The cells were spun down and 30 mL of conditioned media were run on an SDS Gel with reduced loading dye. To lyse the cells, 1 mL of cells expressing the protein of interest (GDF11) were centrifuged and resuspended in 200 uL PBS and 200 uL of Loading Dye. For the reduced run, the loading dye was reduced with beta mercaptoethanol. This sample was boiled for 15 minutes to lyse the cells, spun down, and the supernatant was loaded on the gel. The SDS gel was run at 200V for 30 minutes. For the non-reduced run, the beta mercaptoethanol was used to reduce the samples after it had already been run through the SDS gel. The protein was then transferred to a PVDF membrane using the Bio Rad Trans-Blot® Turbo™ Transfer System. The membrane was blocked with 5% milk diluted in TBST for 10 minutes on a shaking platform. The primary antibody (Rabbit Anti BMP11/GDF8 Abcam Cat #EPR4567) was diluted 1:1000 in 5 mL of 1.5% milk in TBST. The membrane was incubated in the primary antibody on the shaking platform for 2 hours. Then the membrane was washed with TBST 5 times for 5 minutes a wash. The secondary antibody (Anti Rabbit R&D antibody Cat #HAF008) was diluted 1:3000 in 10 mL of 1.5% milk in TBST and the membrane was incubated in the secondary antibody for 1 hour. The membrane was washed again 5 times for 5 minutes per wash and developed using Pierce ECL Plus Western Blotting Substrate. The positive control for mature, WT GDF11 was done through the addition of rGDF11 produced by PeproTech®.

HEK293—(CAGA) Luciferase Reporter Assay

This assay was done using HEK293-(CAGA) luciferase reporter cells, grown overnight on 96-well plates. Next, a 2-fold serial dilution series was prepared for 15 dilutions, starting at 10 nM. After removing the growth media from the CagA Luciferase Reporter cells, 100 µL of the diluted protein—WT GDF11 from PeproTech and the purified GDF11 Indel 7 mutant—was placed into each well, with triplicates for each concentration. The cells were incubated overnight and lysed 16 hours post treatment with 20 µL 1× cell lysis buffer and shook at 900 rpm for 20 minutes. The lysed cells were transferred to a black and white plate and 40 µL of luciferase assay reagent were added to each well in order to read the luminescence. Luminescence was recorded using a BioTek® Synergy H1 Hybrid plate reader. For the analysis the triplicates were averaged and each average was normalized to the negative control-cells only treated with serum free media. The activity data was imported into GraphPad Prism and fit using a non-linear regression with a variable slope to calculate the EC50 value.

Statistical Methods

All analysis was done using ANOVA one-way statistical methods on the GraphPad PRISM 7 software. Post-test analysis was done with Tukey's multiple comparison test.

```
Primer Sequences for Genotyping
GDF11insitu_F:
                                         (SEQ ID NO: 5)
CATGCAAAAGTATCCACACACC GDF11T7E1_F2:
                                         (SEQ ID NO: 6)
CCTGGACTGCGATGAACACT GDF11insitu_R:
                                         (SEQ ID NO: 7)
CCTACTGAGTTGTCAGGGGAAC GDF11sUTR_R:
                                         (SEQ ID NO: 8)
CTGGAAGGAGAGAGGGAAAAA Primer Sequences for qPCR
GDF11 Ex1-2 F:
                                         (SEQ ID NO: 9)
CTGCGCCTAGAGAGCATCAAG GDF11 Ex1-2 R:
                                         (SEQ ID NO: 10)
TTGGAAGTCGTGCAGATCCAG GDF11 Ex2-3 F:
                                         (SEQ ID NO: 11)
ACAGAGCAACTGGGGAATCG GDF11 Ex2-3 R:
                                         (SEQ ID NO: 12)
AGTGTTCATCGCAGTCCAGG Beta-Actin F:
                                         (SEQ ID NO: 13)
ATCAAGATCATTGCTCCTCCTGAG Beta-Actin R:
                                         (SEQ ID NO: 14)
CTGCTTGCTGATCCACATCTG Primer Sequences for Quick Change Mutagenesis
Forward Primer:
                                         (SEQ ID NO: 15)
TGGGTGCTCATGGGAGTAAGACCTGCAGAAGCTTGGC Reverse Primer:
                                         (SEQ ID NO: 16)
CTTCTGCAGGTCTTACTCCCATGAGCACCCACAGCGG Primer Sequences Used for Colony PCR
T7_F:
                                         (SEQ ID NO: 17)
AATACGACTCACTATAGGG M13_R:
                                         (SEQ ID NO: 18)
CAGGAAACAGCTATGAC
```

REFERENCES

1. Faulkner J A, Larkin L M, Claflin D R, Brooks S V. Age-related changes in the structure and function of skeletal muscles. Clin Exp Pharmacol Physiol. 2007; 34(11):1091-6. Epub 2007/09/21. doi: 10.1111/j.1440-1681.2007.04752.x. PubMed PMID: 17880359.
2. Newman A B, Kupelian V, Visser M, Simonsick E M, Goodpaster B H, Kritchevsky S B, Tylaysky F A, Rubin S M, Harris T B. Strength, but not muscle mass, is associated with mortality in the health, aging and body composition study cohort. J Gerontol A Biol Sci Med Sci. 2006; 61(1):72-7. PubMed PMID: 16456196.
3. Rantanen T, Guralnik J M, Foley D, Masaki K, Leveille S, Curb J D, White L. Midlife hand grip strength as a predictor of old age disability. JAMA. 1999; 281(6):558-60. PubMed PMID: 10022113.
4. Janssen I, Shepard D S, Katzmarzyk P T, Roubenoff R. The healthcare costs of sarcopenia in the United States. Journal of the American Geriatrics Society. 2004; 52(1): 80-5. PubMed PMID: 14687319.
5. Aging Ao. "A Profile of Older Americans 2010" 28 Sep. 2011 [cited 2014]. Available from: www.aoa.gov/aoaroot/aging_statistics/Profile/2010/4.aspx.
6. White T A, LeBrasseur N K. Myostatin and sarcopenia: opportunities and challenges—a mini-review. Gerontology. 2014; 60(4):289-93. Epub 2014/01/25. doi: 10.1159/000356740. PubMed PMID: 24457615.
7. Cruz-Jentoft A J, Landi F, Schneider S M, Zuniga C, Arai H, Boirie Y, Chen L K, Fielding R A, Martin F C, Michel J P, Sieber C, Stout J R, Studenski S A, Vellas B, Woo J, Zamboni M, Cederholm T. Prevalence of and interventions for sarcopenia in ageing adults: a systematic review. Report of the International Sarcopenia Initiative (EWGSOP and IWGS). Age and ageing. 2014; 43(6):748-59. doi: 10.1093/ageing/afu115. PubMed PMID: 25241753; PMCID: 4204661.
8. Glass D, Roubenoff R. Recent advances in the biology and therapy of muscle wasting. Ann N Y Acad Sci. 2010; 1211:25-36. doi: 10.1111/j.1749-6632.2010.05809.x. PubMed PMID: 21062293.
9. Loffredo F S, Steinhauser M L, Jay S M, Gannon J, Pancoast J R, Yalamanchi P, Sinha M, Dall'Osso C, Khong D, Shadrach J L, Miller C M, Singer B S, Stewart A, Psychogios N, Gerszten R E, Hartigan A J, Kim M J, Serwold T, Wagers A J, Lee R T. Growth differentiation factor 11 is a circulating factor that reverses age-related cardiac hypertrophy. Cell. 2013; 153(4):828-39. Epub 2013/05/15. doi: 10.1016/j.cell.2013.04.015. PubMed PMID: 23663781; PMCID: 3677132.
10. Katsimpardi L, Litterman N K, Schein P A, Miller C M, Loffredo F S, Wojtkiewicz G R, Chen J W, Lee R T, Wagers A J, Rubin L L. Vascular and neurogenic rejuvenation of the aging mouse brain by young systemic factors. Science. 2014; 344(6184):630-4. doi: 10.1126/science.1251141. PubMed PMID: 24797482; PMCID: 4123747.
11. Sinha M, Jang Y C, Oh J, Khong D, Wu E Y, Manohar R, Miller C, Regalado S G, Loffredo F S, Pancoast J R, Hirshman M F, Lebowitz J, Shadrach J L, Cerletti M, Kim M J, Serwold T, Goodyear U, Rosner B, Lee R T, Wagers A J. Restoring systemic GDF11 levels reverses age-related dysfunction in mouse skeletal muscle. Science. 2014; 344(6184):649-52. doi: 10.1126/science.1251152. PubMed PMID: 24797481; PMCID: 4104429.
12. Ruckh J M, Zhao J W, Shadrach J L, van Wijngaarden P, Rao T N, Wagers A J, Franklin R J. Rejuvenation of regeneration in the aging central nervous system. Cell Stem Cell. 2012; 10(1):96-103. Epub 2012/01/10. doi: 10.1016/j.stem.2011.11.019. PubMed PMID: 22226359; PMCID: 3714794.
13. Sinha I, Sinha-Hikim A P, Wagers A J, Sinha-Hikim I. Testosterone is essential for skeletal muscle growth in aged mice in a heterochronic parabiosis model. Cell Tissue Res. 2014; 357(3):815-21. doi: 10.1007/s00441-014-1900-2. PubMed PMID: 24859218; PMCID: 4149819.
14. Oh J, Lee Y D, Wagers A J. Stem cell aging: mechanisms, regulators and therapeutic opportunities. Nat Med. 2014; 20(8):870-80. doi: 10.1038/nm.3651. PubMed PMID: 25100532; PMCID: 4160113.
15. Poggioli T, Vujic A, Yang P, Macias-Trevino C, A. U, Loffredo F S, Pancoast J R, Cho M, Goldstein J, Tandias R M, E. G, Walker R G, Thompson T B, Wagers A J, Fong Y W, Lee R T. Circulating growth differentiation factor 11/8 levels decline with age. Circ Res. 2015; October 21 [Epub ahead of print].
16. Poggioli T, Vujic A, Yang P, Macias-Trevino C, Uygur A, Loffredo F S, Pancoast J R, Cho M, Goldstein J, Tandias R M, Gonzalez E, Walker R G, Thompson T B, Wagers A J, Fong Y W, Lee R T. Circulating Growth Differentiation Factor 11/8 Levels Decline With Age. Circ Res. 2016; 118(1):29-37. doi: 10.1161/CIRCRESAHA.115.307521. PubMed PMID: 26489925; PMCID: 4748736.
17. Demontis F, Patel V K, Swindell W R, Perrimon N. Intertissue control of the nucleolus via a myokine-dependent longevity pathway. Cell reports. 2014; 7(5):1481-94. doi: 10.1016/j.celrep.2014.05.001. PubMed PMID: 24882005; PMCID: 4125979.
18. Ma S, Upneja A, Galecki A, Tsai Y M, Burant C F, Raskind S, Zhang Q, Zhang Z D, Seluanov A, Gorbunova V, Clish C B, Miller R A, Gladyshev V N. Cell culture-based profiling across mammals reveals DNA repair and metabolism as determinants of species longevity. eLife. 2016; 5. doi: 10.7554/eLife.19130. PubMed PMID: 27874830; PMCID: PMC5148604.
19. Zhou Y, Jiang Z, Harris E C, Reeves J, Chen X, Pazdro R. Circulating Concentrations of Growth Differentiation Factor 11 Are Heritable and Correlate With Life Span. J Gerontol A Biol Sci Med Sci. 2016. doi: 10.1093/gerona/glv308. PubMed PMID: 26774117.
20. Elliott B T, Herbert P, Sculthorpe N, Grace F M, Stratton D, Hayes L D. Lifelong exercise, but not short-term high-intensity interval training, increases GDF11, a marker of successful aging: a preliminary investigation. Physiol Rep. 2017; 5(13). doi: 10.14814/phy2.13343. PubMed PMID: 28701523; PMCID: PMC5506528.
21. Heidecker B, Olson K, Beatty A, Dubin R, Kato S, Lawn R, Murthy A, Regan M, Sterling D, Whooley M, Ganz P. Low levels of growth differentiation factor 11 and high levels of its inhibitor follitatin-like 3 are associated with adverse cardiovascular outcomes in humans Journal of the American College of Cardiology. 2015; 65:10_S.
22. Olson K A, Beatty A L, Heidecker B, Regan M C, Brody E N, Foreman T, Kato S, Mehler R E, Singer B S, Hveem K, Dalen H, Sterling D G, Lawn R M, Schiller N B, Williams S A, Whooley M A, Ganz P. Association of growth differentiation factor 11/8, putative anti-ageing factor, with cardiovascular outcomes and overall mortality in humans: analysis of the Heart and Soul and HUNTS cohorts. European heart journal. 2015. doi: 10.1093/eurheartj/ehv385. PubMed PMID: 26294790.
23. McPherron A C, Lawler A M, Lee S J. Regulation of anterior/posterior patterning of the axial skeleton by growth/differentiation factor 11. Nat Genet. 1999; 22(3): 260-4. Epub 1999/07/03. doi: 10.1038/10320. PubMed PMID: 10391213.
24. Bajikar, S. S., Wang, C. C., Borten, M. A., Pereira, E. J., Atkins, K. A., & Janes, K. A. (2017). Tumor-Suppressor Inactivation of GDF11 Occurs by Precursor Sequestration in Triple-Negative Breast Cancer. Dev Cell, 43(4), 418-435 e413. doi:10.1016/j.devcel.2017.10.027.
25. Castellano, J. M., Mosher, K. I., Abbey, R. J., McBride, A. A., James, M. L., Berdnik, D., . . . Wyss-Coray, T. (2017). Human umbilical cord plasma proteins revitalize hippocampal function in aged mice. nature, 544(7651), 488-492. doi:10.1038/nature22067.
26. Conboy, I. M., Conboy, M. J., Wagers, A. J., Girma, E. R., Weissman, I. L., & Rando, T. A. (2005). Rejuvenation of aged progenitor cells by exposure to a young systemic environment. nature, 433(7027), 760-764. doi:10.1038/nature03260.
27. Derynck, R., & Zhang, Y. E. (2003). Smad-dependent and Smad-independent pathways in TGF-beta family signalling. nature, 425(6958), 577-584. doi:10.1038/nature02006.
28. Doudna, J. A., & Charpentier, E. (2014). Genome editing. The new frontier of genome engineering with CRISPR-Cas9. Science, 346(6213), 1258096. doi: 10.1126/science.1258096.
29. Dussiot, M., Maciel, T. T., Fricot, A., Chartier, C., Negre, O., Veiga, J., . . . Moura, I. C. (2014). An activin receptor IIA ligand trap corrects ineffective erythropoiesis in beta-thalassemia. Nat Med, 20(4), 398-407. doi:10.1038/nm.3468.
30. Egerman, M. A., Cadena, S. M., Gilbert, J. A., Meyer, A., Nelson, H. N., Swalley, S. E., . . . Glass, D. J. (2015). GDF11 Increases with Age and Inhibits Skeletal Muscle Regeneration. Cell Metab, 22(1), 164-174. doi:10.1016/j.cmet.2015.05.010.
31. Gamer, L. W., Wolfman, N. M., Celeste, A. J., Hattersley, G., Hewick, R., & Rosen, V. (1999). A novel BMP expressed in developing mouse limb, spinal cord, and tail bud is a potent mesoderm inducer in Xenopus embryos. Dev Biol, 208(1), 222-232. doi:10.1006/dbio.1998.9191.
32. Hammers, D. W., Merscham-Banda, M., Hsiao, J. Y., Engst, S., Hartman, J. J., & Sweeney, H. L. (2017). Supraphysiological levels of GDF11 induce striated muscle atrophy. *EMBO Mol Med,* 9(4), 531-544. doi: 10.15252/emmm.201607231.

33. Harmon, E. B., Apelqvist, A. A., Smart, N. G., Gu, X., Osborne, D. H., & Kim, S. K. (2004). GDF11 modulates NGN3+ islet progenitor cell number and promotes beta-cell differentiation in pancreas development. *Development,* 131(24), 6163-6174. doi:10.1242/dev.01535.

34. Harper, S. C., Brack, A., MacDonnell, S., Franti, M., Olwin, B. B., Bailey, B. A., . . . Houser, S. R. (2016). Is Growth Differentiation Factor 11 a Realistic Therapeutic for Aging—Dependent Muscle Defects? *Circ Res,* 118(7), 1143-1150; discussion 1150. doi:10.1161/CIRCRESAHA.116.307962.

35. Hinken, A. C., Powers, J. M., Luo, G., Holt, J. A., Billin, A. N., & Russell, A. J. (2016). Lack of evidence for GDF11 as a rejuvenator of aged skeletal muscle satellite cells. *Aging Cell,* 15(3), 582-584. doi:10.1111/acel.12475.

36. Jones, J. E., Cadena, S. M., Gong, C., Wang, X., Chen, Z., Wang, S. X., . . . Glass, D. J. (2018). Supraphysiologic Administration of GDF11 Induces Cachexia in Part by Upregulating GDF15. *Cell Rep,* 22(6), 1522-1530. doi: 10.1016/j.celrep.2018.01.044.

37. McPherron, A. C., Lawler, A. M., & Lee, S.-J. (1997). Regulation of skeletal muscle mass in mice by a new TGF-beta superfamily member. *nature,* 387(6628), 83.

38. McPherron, A. C., Lawler, A. M., & Lee, S. J. (1999). Regulation of anterior/posterior patterning of the axial skeleton by growth/differentiation factor 11. *Nat Genet,* 22(3), 260-264. doi:10.1038/10320.

39. Nakashima, M., Toyono, T., Akamine, A., & Joyner, A. (1999). Expression of growth/differentiation factor 11, a new member of the BMP/TGFbeta superfamily during mouse embryogenesis. *Mech Dev,* 80(2), 185-189.

40. Rochette, L., Zeller, M., Cottin, Y., & Vergely, C. (2015). Growth and differentiation factor 11 (GDF11): Functions in the regulation of erythropoiesis and cardiac regeneration. *Pharmacol Ther,* 156, 26-33. doi:10.1016/j.pharmthera.2015.10.006.

41. Santos, R., Wu, J., Hamilton, J. A., Pinter, R., Hindges, R., & Calof, A. L. (2012). Restoration of retinal development in Vsx2 deficient mice by reduction of Gdf11 levels. *Adv Exp Med Biol,* 723, 671-677. doi:10.1007/978-1-4614-0631-0_85.

42. Schafer, M. J., Atkinson, E. J., Vanderboom, P. M., Kotajarvi, B., White, T. A., Moore, M. M., . . . LeBrasseur, N. K. (2016). Quantification of GDF11 and Myostatin in Human Aging and Cardiovascular Disease. *Cell Metab,* 23(6), 1207-1215. doi:10.1016/j.cmet.2016.05.023.

43. Smith, S. C., Zhang, X., Zhang, X., Gross, P., Starosta, T., Mohsin, S., . . . Houser, S. R. (2015). GDF11 does not rescue aging-related pathological hypertrophy. *Circ Res,* 117(11), 926-932. doi:10.1161/CIRCRESAHA.115.307527.

44. Suragani, R. N., Cadena, S. M., Cawley, S. M., Sako, D., Mitchell, D., Li, R., . . . Kumar, R. (2014). Transforming growth factor-beta superfamily ligand trap ACE-536 corrects anemia by promoting late-stage erythropoiesis. *Nat Med,* 20(4), 408-414. doi:10.1038/nm.3512.

45. Walker, R. G., Czepnik, M., Goebel, E. J., McCoy, J. C., Vujic, A., Cho, M., . . . Thompson, T. B. (2017). Structural basis for potency differences between GDF8 and GDF11. *BMC Biol,* 15(1), 19. doi:10.1186/s12915-017-0350-1.

46. Walker, R. G., Poggioli, T., Katsimpardi, L., Buchanan, S. M., Oh, J., Wattrus, S., . . . Lee, R. T. (2016). Biochemistry and Biology of GDF11 and Myostatin: Similarities, Differences, and Questions for Future Investigation. *Circ Res,* 118(7), 1125-1141; discussion 1142. doi:10.1161/CIRCRESAHA.116.308391.

47. Zhang, Y., Wei, Y., Liu, D., Liu, F., Li, X., Pan, L., . . . Chen, D. (2017). Role of growth differentiation factor 11 in development, physiology and disease. *Oncotarget,* 8(46), 81604-81616. doi:10.18632/oncotarget.20258.

48. Zimmers, T. A., Jiang, Y., Wang, M., Liang, T. W., Rupert, J. E., Au, E. D., . . . Koniaris, L. G. (2017). Exogenous GDF11 induces cardiac and skeletal muscle dysfunction and wasting. *Basic Res Cardiol,* 112(4), 48. doi:10.1007/s00395-017-0639-9.

```
SEQUENCES
SEQ ID NO: 1
Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160
```

```
Cys Cys His Phe His Phe Ser Pro Lys Val Met Phe Thr Lys Val Leu
            165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
            195                 200                 205

Ala Gly Gly Gly Gly Gly Arg His Ile Arg Ile Arg Ser Leu
            210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
            245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
            275                 280                 285

Val Leu Glu Asn Thr Lys Arg Ser Arg Arg Asn Leu Gly Leu Asp Cys
            290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
            325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
            355                 360                 365

Gly Pro Cys Cys Thr Pro Thr Lys Met Ser Pro Ile Asn Met Leu Tyr
370                 375                 380

Phe Asn Asp Lys Gln Gln Ile Ile Tyr Gly Lys Ile Pro Gly Met Val
            385                 390                 395                 400

Val Asp Arg Cys Gly Cys Ser
            405

SEQ ID NO: 2
Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
            20                  25                  30

Pro Glu Pro Asp Gly Cys Pro Val Cys Val Trp Arg Gln His Ser Arg
            35                  40                  45

Glu Leu Arg Leu Glu Ser Ile Lys Ser Gln Ile Leu Ser Lys Leu Arg
50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
            85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
        115                 120                 125

Val Gln Thr Asp Gly Ser Pro Leu Cys Cys His Phe His Phe Ser Pro
        130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
```

-continued

```
                165                 170                 175
Lys Pro Leu Thr Gly Glu Gly Thr Ala Gly Gly Gly Gly Gly Arg
    180                 185                 190

Arg His Ile Arg Ile Arg Ser Leu Lys Ile Glu Leu His Ser Arg Ser
    195                 200                 205

Gly His Trp Gln Ser Ile Asp Phe Lys Gln Val Leu His Ser Trp Phe
    210                 215                 220

Arg Gln Pro Gln Ser Asn Trp Gly Ile Glu Ile Asn Ala Phe Asp Pro
225                 230                 235                 240

Ser Gly Thr Asp Leu Ala Val Thr Ser Leu Gly Pro Gly Ala Glu Gly
            245                 250                 255

Leu His Pro Phe Met Glu Leu Arg Val Leu Glu Asn Thr Lys Arg Ser
        260                 265                 270

Arg Arg Asn Leu Gly Leu Asp Cys Asp Glu His Ser Ser Glu Ser Arg
    275                 280                 285

Cys Cys Arg Tyr Pro Leu Thr Val Asp Phe Glu Ala Phe Gly Trp Asp
    290                 295                 300

Trp Ile Ile Ala Pro Lys Arg Tyr Lys Ala Asn Tyr Cys Ser Gly Gln
305                 310                 315                 320

Cys Glu Tyr Met Phe Met Gln Lys Tyr Pro His Thr His Leu Val Gln
            325                 330                 335

Gln Ala Asn Pro Arg Gly Ser Ala Gly Pro Cys Cys Thr Pro Thr Lys
        340                 345                 350

Met Ser Pro Ile Asn Met Leu Tyr Phe Asn Asp Lys Gln Gln Ile Ile
    355                 360                 365

Tyr Gly Lys Ile Pro Gly Met Val Val Asp Arg Cys Gly Cys Ser
    370                 375                 380

SEQ ID NO: 3
Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
            85                  90                  95

Lys Ile Pro Gly Met Val Val Asp Arg Cys Gly Cys Ser
        100                 105

SEQ ID NO: 4
Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
            20                  25                  30

Pro Glu Pro Asp Gly Cys Pro Val Cys Val Trp Arg Gln His Ser Arg
        35                  40                  45

Glu Leu Arg Leu Glu Ser Ile Lys Ser Gln Ile Leu Ser Lys Leu Arg
    50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
            85                  90                  95
```

```
Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
        115                 120                 125

Val Gln Thr Asp Gly Ser Pro Leu Cys Cys His Phe His Phe Ser Pro
    130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175

Lys Pro Leu Thr Gly Glu Gly Thr Ala Gly Gly Gly Gly Gly Gly Arg
            180                 185                 190

Arg His Ile Arg Ile Arg Ser Leu Lys Ile Glu Leu His Ser Arg Ser
        195                 200                 205

Gly His Trp Gln Ser Ile Asp Phe Lys Gln Val Leu His Ser Trp Phe
    210                 215                 220

Arg Gln Pro Gln Ser Asn Trp Gly Ile Glu Ile Asn Ala Phe Asp Pro
225                 230                 235                 240

Ser Gly Thr Asp Leu Ala Val Thr Ser Leu Gly Pro Gly Ala Glu Gly
                245                 250                 255

Leu His Pro Phe Met Glu Leu Arg Val Leu Glu Asn Thr Lys Arg Ser
            260                 265                 270

Arg Arg
```

---

What is claimed is:

1. A GDF11 variant comprising a modification to the C-terminus of a native GDF11 protein, wherein the modification comprises inclusion of at least two additional amino acids at the C-terminus, wherein the at least two additional amino acids comprise tryptophan and glutamic acid, or conservative amino acid substitutions therefor, and wherein the tryptophan, or a conservative amino acid substitution therefor, is directly attached to the last amino acid of the C-terminus of the native GDF11 protein.

2. The GDF11 variant of claim 1, wherein the inclusion of at least two additional amino acids comprises inclusion of at least six additional amino acids at the C-terminus.

3. The GDF11 variant of claim 2, wherein the two amino acids included are tryptophan and glutamic acid.

4. The GDF11 variant of claim 1, wherein the native GDF11 protein is at least 90% identical to SEQ ID NO: 2 or SEQ ID NO: 3.

5. The GDF11 variant of claim 1, wherein the GDF11 variant has a reduced number of disulfide bridges as compared to the native GDF11 protein and/or has increased protein stability as compared to the native GDF11 protein.

6. The GDF11 variant of claim 1, wherein the GDF11 variant comprises the amino acid sequence of SEQ ID NO: 20.

7. A pharmaceutical composition comprising the GDF11 variant of claim 1 and a pharmaceutically acceptable carrier.

8. The pharmaceutical composition of claim 7, wherein the pharmaceutical composition is formulated for administration by a mode selected from the group consisting of: topically, by injection, by intravenous injection, by inhalation, continuous release by depot or pump, and a combination thereof.

9. A method for increasing angiogenesis, increasing neurogenesis, rejuvenating skeletal muscle stem cells, or increasing strength or exercise endurance capacity in a subject in need thereof, comprising administering to the subject a GDF11 variant polypeptide comprising a modification to the C-terminus of a native GDF11 protein, wherein the modification comprises inclusion of at least two additional amino acids at the C-terminus, wherein the at least two additional amino acids comprise tryptophan and glutamic acid, or conservative amino acid substitutions therefor, and wherein the tryptophan, or a conservative amino acid substitution therefor, is directly attached to the last amino acid of the C-terminus of the native GDF11 protein, thereby increasing angiogenesis, increasing neurogenesis, rejuvenating skeletal muscle stem cells, or increasing strength or exercise endurance capacity in the subject.

10. The method of claim 9, wherein increasing angiogenesis comprises increasing cerebrovascular architecture, increasing capillary density, increasing cerebral blood flow, and increasing cerebral vessel sprouting branch points.

11. The method of claim 9, wherein increasing neurogenesis is associated with increased neural cell proliferation, increased neural cell differentiation, increased number or proliferation rate of neural stem cells, increased number or proliferation rate of neural progenitor cells, increased number or proliferation rate of neural precursor cells, increased expression of at least one synaptic plasticity gene, at least one neuroprotective gene, or at least one neuronal specification gene, or increased number of new neurons.

12. The method of claim 9, wherein the administration of GDF11 variant polypeptide to the subject increases GDF11 protein in the subject.

13. The method of claim 12, wherein the level of GDF11 protein is increased in at least one of the subject's systemic circulation, cerebral vasculature, cerebral tissue, cerebrospinal fluid, lateral ventricles, neurovasculature, and subventricular zone neurovascular niche.

14. The method of claim 12, wherein the level of GDF11 protein is increased by at least 100% or increased to at least 75% of a healthy reference level.

15. The method of claim 9, wherein the GDF11 variant causes the subject's skeletal muscle stem cells to increase in frequency or number, increase the sizes of regenerating myofibers, increase the efficiency of myogenic colony formation, increase the percentage of intact nuclei, and decrease the percentage of severely damaged deoxyribonucleic acid (DNA), thereby rejuvenating the skeletal muscle stem cells in the subject.

16. The method of claim 9, wherein the subject has been diagnosed with a skeletal muscle condition due to aging.

17. The method of claim 9, wherein the GDF11 variant comprises inclusion of at least two amino acids at the C-terminus as compared to a native GDF11 protein.

18. The method of claim 17, wherein the two amino acids included are tryptophan and glutamic acid.

19. The method of claim 17, wherein the native GDF11 protein is at least 90% identical to SEQ ID NO: 2 or SEQ ID NO: 3.

20. A method for treating a neurovascular disorder or neurodegenerative disorder in a subject, comprising administering to the subject a GDF11 variant polypeptide of claim 1 which increases the level of GDF11 protein in the subject, thereby treating or preventing the neurovascular or neurodegenerative disorder in the subject.

* * * * *